US012414950B1

(12) United States Patent
Rothbaum et al.

(10) Patent No.: US 12,414,950 B1
(45) Date of Patent: *Sep. 16, 2025

(54) METHODS OF TREATING INDOLENT SYSTEMIC MASTOCYTOSIS

(71) Applicant: Telios Pharma Inc., Redwood City, CA (US)

(72) Inventors: Wayne Rothbaum, Delray Beach, FL (US); Reg Myers, Redwood City, CA (US)

(73) Assignee: TELIOS PHARMA INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/961,657

(22) Filed: Nov. 27, 2024

Related U.S. Application Data

(60) Provisional application No. 63/650,348, filed on May 21, 2024.

(51) Int. Cl.
*A61K 31/506* (2006.01)
*A61P 7/00* (2006.01)

(52) U.S. Cl.
CPC .............. *A61K 31/506* (2013.01); *A61P 7/00* (2018.01)

(58) Field of Classification Search
CPC ............................... A61K 31/506; A61P 7/00
See application file for complete search history.

(56) References Cited

U.S. PATENT DOCUMENTS

| | | |
|---|---|---|
| 8,227,433 B2 | 7/2012 | Auclair et al. |
| 9,073,947 B2 | 7/2015 | Hodous et al. |
| 9,580,449 B2 | 2/2017 | Hodous et al. |
| 10,016,448 B2 | 7/2018 | Hodous et al. |
| 10,413,562 B2 | 9/2019 | Hodous et al. |
| 11,878,967 B2 | 1/2024 | Lange et al. |
| 2014/0155385 A1 | 6/2014 | Barf et al. |
| 2015/0283142 A1 | 10/2015 | Stern et al. |
| 2016/0279135 A1 | 9/2016 | Lannutti et al. |
| 2017/0037145 A1 | 2/2017 | Geuijen et al. |
| 2017/0157251 A1 | 6/2017 | Bonvini et al. |
| 2017/0224688 A1 | 8/2017 | Krejsa |
| 2020/0352920 A1 | 11/2020 | Flynn et al. |
| 2020/0377953 A1 | 12/2020 | Choy et al. |
| 2022/0048909 A1 | 2/2022 | Bushaboina et al. |
| 2022/0313819 A1 | 10/2022 | Donio et al. |
| 2022/0395509 A1 | 12/2022 | Treon et al. |
| 2023/0058545 A1 | 2/2023 | Treon et al. |
| 2023/0339865 A1 | 10/2023 | Gray et al. |
| 2024/0175086 A1 | 5/2024 | Choy et al. |
| 2024/0282425 A1 | 8/2024 | Low |
| 2024/0293403 A1 * | 9/2024 | Rothbaum ............ A61K 31/506 |

FOREIGN PATENT DOCUMENTS

| | | |
|---|---|---|
| CN | 106478633 A | 3/2017 |
| EP | 1473039 A1 | 11/2004 |
| WO | 2015/151006 A1 | 10/2015 |
| WO | 2015/170266 A1 | 11/2015 |
| WO | 2017/025814 A1 | 2/2017 |
| WO | 2020/176868 A1 | 9/2020 |
| WO | 2022/034529 A1 | 2/2022 |
| WO | WO-2022266285 A1 * | 12/2022 ......... A61K 31/4545 |
| WO | 2023/183652 A1 | 9/2023 |
| WO | 2023/220192 A1 | 11/2023 |
| WO | 2024/039883 A2 | 2/2024 |

OTHER PUBLICATIONS

Gilfillan et al., "The tyrosine kinase network regulating mast cell activation," Immunological Reviews, 228 (1): 149-169 (2009).
Jensen et al., "Concurrent inhibition of Kit- and FceRI-mediated signaling," Journal of Pharmacology and Experimental Therapeutics, 324 (1): 128-138 (2008).
Chifotides et al., "SOHO State of the Art Update and Next Questions: Current and Emerging Therapies for Systemic Mastocytosis," Clinical Lymphoma, Myeloma and Leukemia (2024).
Gotlib et al., "Proceedings from the Inaugural American Initiative in Mast Cell Disease (AIM) Investigator Conference," Journal of Allergy and Clinical Immunology, 147: 2043-2052 (2021).
Munoz-Gonzalez et al., "Frequency and prognostic impact of KIT and other genetic variants in indolent systemic mastocytosis," Blood, 134 (5): 456-468 (2019).
Greiner et al., "Molecular quantification of tissue disease burden is a new biomarker and independent predictor of survival in mastocytosis," Haematologica, 105 (2): 366-374 (2020).
Valent et al., "Mastocytosis: 2016 updated WHO classification and novel emerging treatment concepts," Blood, 129 (11): 1420-1427 (2017).
Gotlib et al., "Systemic Mastocytosis, Version 3.2024: Featured Updates to the NCCN Guidelines," Journal of the National Comprehensive Cancer Network, 22 (2D): e240030 (2024).
Gotlib et al., "Avapritinib versus Placebo in Indolent Systemic Mastocytosis," NEJM Evidence, 2 (6) (2023).
Mukherjee et al., "Decreased Survival Among Patients with Indolent Systemic Mastocytosis: A Population-Level Retrospective Cohort Analysis Using Healthcare Claims Dataset," Blood, 142 (Supplement 1), 75-77 (2023).
Costa et al., "Systemic mastocytosis: 2023 update on diagnosis and management in adults," Expert Opinion on Emerging Drugs (2023).
Veitch et al., "Mastocytosis demystified," Hematology, 396-406 (2023).

(Continued)

*Primary Examiner* — James H Alstrum-Acevedo
*Assistant Examiner* — Carolyn L. Ladd
(74) *Attorney, Agent, or Firm* — Morgan, Lewis & Bockius LLP

(57) ABSTRACT

Therapeutic methods and pharmaceutical compositions for treating indolent systemic mastocytosis (ISM) in a human subject are described. In certain embodiments, the disclosure includes therapeutic methods of treating ISM using a BTK inhibitor. The disclosure also includes therapeutic methods of reducing or alleviating symptoms of ISM in a human subject.

26 Claims, 36 Drawing Sheets

(56) References Cited

OTHER PUBLICATIONS

Gonzalez-Lopez et al., "Comprehensive Analysis of Acquired Genetic Variants and Their Prognostic Impact in Systemic Mastocytosis," Cancers, 14: 2487 (2022).

Gleixner et al., "KIT-D816V-independent oncogenic signaling in neoplastic cells in systemic mastocytosis: role of Lyn and Btk activation and disruption by dasatinib and bosutinib," Blood, 118 (7): 1885-1898 (2011).

Pieri et al., "Clinical presentation and management practice of systemic mastocytosis. A survey on 460 Italian pateints," American Journal of Hematology, 91 (7): 692-699 (2016).

Jawhar et al., "Molecular profiling of myeloid progenitor cells in multi-mutated advanced systemic mastocytosis identifies Kit D816V as a distinct and late event," Leukemia, 29: 1115-1122 (2015).

Leguit et al., "The Spectrum of Aggressive Mastocytosis; A Workshop Report and Literature Review," Pathobiology, 87: 2-19 (2020).

Greiner et al., "Tumor necrosis factor alpha promotes clonal dominance of KIT D816V+ cells in mastocytosis: role of survivin and impact on prognosis," Blood, 143 (11): 1006-1015 (2024).

Gamperl et al., "Effects of ibrutinib on proliferation and histamine release in canine neoplastic mast cells," Verterinary and Comparative Oncology, 14: 553-561 (2019).

Randall et al., "Bosutinib, a Lyn/Btk inhibiting tyrosine kinase inhibitor, is ineffective in advanced systemic mastocytosis," American Journal of Hematology, 90 (4): E74 (2015).

Gilfillan et al., "The tyrosine kinase network regulating mast cell activation," Immunological Reviews, 228: 149-169 (2009).

Zorn et al., "Stimulus strength determines the BTK-dependence of the SHIP1-deficient phenotype in IgE/antigen-triggered mast cells," Scientific Reports, 8: 15467 (2018).

Kneidinger et al., "The effects of dasatinib on IgE receptor-dependent activation and histamine release in human basophils," Blood, 111 (6): 3097-3107 (2008).

Verstovsek et al., "Phase II Study of Dasatinib in Philadelphia Chromosome-Negative Acute and Chronic Myeloid Diseases, Including Systemic Mastocytosis," Clinical Cancer Research, 14 (12): 3906-3915 (2008).

Smiljkovic et al., "BTK inhibition is a potent approach to block IgE-mediated histamine release in human basophils," Allergy, 72: 1666-1676 (2017).

Villanueva et al., "Functional human skin explants as tools for assessing mast cell activation and inhibition," Frontiers in Allergy, 5: 1373511 (2024).

Kuehn et al., "Btk-dependent Rac activation and actin rearrangement following FcERI aggregation promotes enhanced chemotactic responses of mast cells," Journal of Cell Science, 123: 2576-2585 (2010).

Valent et al., "Drug-induced mast cell eradication: A novel approach to treat mast cell activation disorders?" Journal of Allergy and Clinical Immunology, 149: 1866-1874 (2022).

Gotlib, "Update on Systemic Mastocytosis," MPN-MDS US Focus Meeting (2024).

Peter et al., "Drug-induced inhibition of phosphorylation of STAT5 overrides drug resistance in neoplastic mast cells," Leukemia, 32 (4): 1016-1022 (2018).

Sabato et al., "Mast Cell-Targeting Therapies in Mast Cell Activation Syndromes," Current Allergy and Asthma Reports, 24 (2): 63-71 (2024) (see abstract).

Stevens et al., "Recent insights into the mechanisms of anaphylaxis," Current Opinion in Immunology, 81: 102288 (2023) (see abstract).

Jacobs et al., "Kinase inhibitors developed for treatment of hematologic malignancies: Implications for immune modulation in COVID-19," Blood Advances, 5 (3): 913-924 (2021).

Telios Pharma, Inc. "Study of TL-895 in Subjects with Myelofibrosis or Indolent Systemic Mastocytosis," ClinicalTrials NCT04655118 (2024).

Butterfield et al., "Establishment of an Immature Mast Cell Line from a Patient with Mast Cell Leukemia," Leukemia Research, 12 (4): 345-355 (1988).

Goodstal et al., "Preclinical evidence for the effective use of TL-895, a highly selective and potent second-generation BTK inhibitor for the treatment of B-cell malignancies," Scientific Reports, 13: 20412 (2023).

Arber et al., "The Updated WHO Classification of Hematological Malignancies: The 2016 revision to the World Health Organization Classification of myeloid neoplasms and acute leukemia," Blood, 127 (20): 2391-2405 (2016).

Valent et al., "Standards and standardization in mastocytosis: Consensus Statements on Diagnostics, Treatment Recommendations and Response Criteria," European Journal of Clinical Investigation, 37: 435-453 (2007).

Valent et al., "World Health Organization Classification and Diagnosis of Mastocytosis: Update 2023 and Future Perspectives," Immunology and Allergy Clinics, 43: 627-649 (2023).

Khoury et al., "The 5th edition of the World Health Organization Classification of Haematolymphoid Tumours: Myeloid and Histiocytic/Dendritic Neoplasms," Leukemia, 36: 1703-1719 (2022).

Pardanani, "Systemic mastocytosis in adults: 2021 Update on diagnosis, risk stratification and management," American Journal of Hematology, 96: 508-525 (2021).

Rix et al., "Global target profile of the kinase inhibitor bosutinib in primary chronic myeloid leukemia cells," Leukemia, 23: 477-485 (2009).

Valent et al., "Definitions, Criteria and Global Classification of Mast Cell Disorders with Special Reference to Mast Cell Activation Syndromes: A Consensus Proposal," International Archives of Allergy and Immunology, 157: 215-225 (2012).

* cited by examiner

| Donor | EC$_{50}$ (μM) | | | EC$_{90}$ (μM) | | |
|---|---|---|---|---|---|---|
| | 2 hr | 24 hr | 48 hr | 2 hr | 24 hr | 48 hr |
| A | 0.49 | - | - | 1.39 | - | - |
| B | 0.42 | 0.11 | 0.1 | 0.72 | 0.18 | 0.12 |
| C | 0.44 | 0.13 | 0.12 | 0.81 | 0.19 | 0.17 |
| D | 0.51 | 0.11 | 0.1 | 0.97 | 0.18 | 0.14 |
| E | 0.52 | 0.12 | 0.11 | 1.01 | 0.19 | 0.14 |
| F | 0.55 | 0.13 | 0.1 | 1.12 | 0.19 | * |
| Median | 0.5 | 0.12 | 0.1 | 0.99 | 0.19 | 0.14 |

* Could not calculate EC$_{90}$ due to unstable hill slope in curve fit

METHODS OF TREATING INDOLENT SYSTEMIC MASTOCYTOSIS

FIELD OF THE DISCLOSURE

Methods of treating indolent systemic mastocytosis (ISM) using a Bruton's Tyrosine Kinase (BTK) inhibitor are disclosed herein.

BACKGROUND

Mastocytosis is a group of heterogeneous hematologic neoplasms characterized by an abnormally active mast cell population that exhibits stimulus-independent proliferative capacity, and by abnormal expansion and accumulation of mast cells in different tissues including cutaneous or extracutaneous organs such as bone marrow, liver, spleen, lymph nodes, lung or gastrointestinal system. The World Health Organization (WHO) subclassified mastocytosis as cutaneous mastocytosis (CM), systemic mastocytosis (SM), and mast cell sarcoma (MCS). SM is further subclassified as non-advanced mastocytosis with an ICD-O code of 9741/1 and advanced systemic mastocytosis (AdvSM) with a different ICD-O code (9741/3). Non-advanced mastocytosis includes indolent systemic mastocytosis (ISM), bone marrow mastocytosis (BMM), and smoldering systemic mastocytosis (SSM). AdvSM includes aggressive systemic mastocytosis (ASM), and systemic mastocytosis with an associated hematologic neoplasm (SM-AHN). Within Non-advanced mastocytosis, based on the 5th edition of the World Health Organization (WHO) Classification of Hematolymphoid Tumors (WHO5-HEM; 2022), BMM is considered a distinct SM subtype with a favorable prognosis and refers to patients who meet the criteria for SM, have no skin lesions, no B or C findings, and have a serum tryptase level<125 ng/ml. B findings stem from a high burden of MCs without evidence of organ damage, whereas C findings are indicative of SM-induced organ damage caused by infiltration of neoplastic MCs, and cytoreduction is usually required. ISM is the most common SM subtype and is diagnosed when ≤1 B finding is present, and C findings are absent. ISM patients usually have a low MC burden and skin lesions. ISM patients can have a wide range of symptoms, which can be debilitating and affect multiple organ systems, underscoring the heterogeneity of ISM with respect to symptom burden and management. SSM is characterized by a higher burden of neoplastic MCs, i.e., ≥2 B findings, but no C findings (no organ damage attributable to infiltration by the MCs) (Chifotides et al., *Clinical Lymphoma, Myeloma and Leukemia*, doi.org/10.1016/j.clml.2024.06.005).

ISM, the most common disease variant, is a distinct, rare clonal hematologic disorder mediated by activated mast cells that cause a suite of signs and symptoms attributed to constitutive activation of KIT, a receptor tyrosine kinase expressed on mast cells. Activated mast cells release preformed mediators (e.g., histamine, prostaglandins, tryptase, leukotrienes) that exert local action on nerve endings and endothelial cells, affecting vascular permeability and initiating an inflammatory cascade. In ISM patients, episodic or prolonged inflammation in the tissues affected by mast cell infiltration can lead to symptoms related to high cytokine burden (Veitch et al., *Hematology Am Soc Hematol Educ Program* 2023 (1): 396-406; Greiner et al., *Blood*, 2024, 143(11), 1006-1017). Treatment options for ISM patients remain limited, with typical over-the-counter supportive therapy mostly insufficient to control debilitating constitutional symptoms. The key clinical features that differentiate ISM from ASM are less aggressive infiltration/proliferation of tissue mast cells and lack of organ impairment. Patients with ISM have mast cell tissue infiltrates, but do not exhibit organ damage resulting from mast cell infiltration (Chifotides et al., *Clinical Lymphoma, Myeloma and Leukemia*, doi.org/10.1016/j.clml.2024.06.005).

ISM patients may have near-normal life expectancy, only somewhat reduced compared with age- and sex-matched control populations, independent of disease progression (Costa et al., *Expert Opinion on Emerging Drugs* 28.3 (2023): 153-165; Mukherjee et al., *Blood* 142 (2023) 75-77; Chifotides et al., *Clinical Lymphoma, Myeloma and Leukemia*, doi.org/10.1016/j.clml.2024.06.005). In fact, ISM patients very rarely experience disease progression, with only less than 3% developing a more advanced form of SM (Costa et al., *Expert Opinion on Emerging Drugs* 28.3 (2023): 153-165). However, despite having negligible impact on a patient's lifespan, ISM disease symptoms can be quite severe, leading to impaired daily functioning, including inability to leave the home and participate in the workforce, and to significantly decreased quality of life.

Biologically, ISM is a very different disease from the group of AdvSM. In ISM, the KIT D816V or other K/T mutation is limited to mast cells, while in patients with AdvSM, evidence of multilineage carriage of KIT mutations is commonly observed (Leguit et al., *Pathobiology* 87.1 (2020): 2-19; Gonzalez-Lopez et al., *Cancers* 14.10 (2022): 2487). In ISM, patients are very unlikely to carry additional pathogenic mutations (such as myeloid-related high-molecular risk genetic variants), whereas patients with AdvSM acquire KIT mutations in the context of other pathogenic variants that alter the biology of the malignant clones. In AdvSM, KIT mutation may occur earlier in hematopoiesis and affects more cell types, not just mast cells, based on presence of uncommitted hematopoietic precursor cells with KIT mutations, generally higher variant allele frequency (VAF) of KIT mutations in blood or bone marrow, and evidence of other somatic mutations associated with clonal hematopoiesis (Jawhar et al., *Leukemia* 29.5 (2015): 1115-1122; Leguit et al., *Pathobiology* 87.1 (2020): 2-19; Gonzalez-Lopez et al., *Cancers* 14.10 (2022): 2487). By contrast, in ISM patients, the somatic mutation of KIT is a late event in development of clonal mast cells (Jawhar et al., *Leukemia* 29.5 (2015): 1115-1122). Patients with ASM have a significantly high rate of AML transformation (Pieri et al., *American Journal of Hematology* 91.7 (2016): 692-699). Both the presence of multilineage KIT mutations and observation of high-VAF KIT mutations in blood or bone marrow were associated with mutations in other hematologic-risk genes; all of the above factors inform risk stratification in patients with AdvSM, with high-VAF of KIT mutations also prognostic for overall survival (OS) in patients with AdvSM (Greiner et al., *Haematologica* 105.2 (2020): 366; Ganzalez-Lopez et al., *Cancers* 14.10 (2022): 2487; Chifotides et al., *Clinical Lymphoma, Myeloma and Leukemia*, doi.org/10.1016/j.clml.2024.06.005). Very few ISM patients (~7%) carry pathogenic variants other than a KIT mutation, and the presence of additional mutations is associated with other prognostic risk factors, including high VAF of KIT mutation, advanced age at the time of diagnosis and increased $\beta 2$-microglobulin, a marker of systemic inflammation (Pieri et al., *American Journal of Hematology* 91.7 (2016): 692-699; Munoz-Gonzalez et al., *Blood, The Journal of the American Society of Hematology* 134.5 (2019): 456-468).

The vast majority of patients with AdvSM have de novo onset of disease, without prior diagnosis of a non-advanced form of SM. Clinically, in ASM the tissue mast cell burden is greatly increased in one or more compartments, with findings such as bone marrow dysfunction (cytopenias), elevated liver enzymes, osteolytic lesions, and weight loss, that indicate impairment of organ function, and a variety of additional symptoms associated with organomegaly or lymphadenopathy (Leguit et al., *Pathobiology* 87.1 (2020): 2-19, Gotlib et al., *Journal of Allergy and Clinical Immunology* 147.6 (2021): 2043-2052). In mast cell leukemia (MCL), mast cells are present at ≥20% of nucleated cells in bone marrow aspirate smears, with or without presence of leukemic mast cells in the peripheral blood (Chifotides et al., *Clinical Lymphoma, Myeloma and Leukemia*, doi.org/10.1016/j.clml.2024.06.005). Systemic treatment of ASM, SM-AHN, and MCL is directed to reduce the expansion of malignant mast cells, to decrease the tissue burden of malignant cells in affected organs, and to improve organ function.

A study of dasatinib, a $2^{nd}$ generation tyrosine kinase inhibitor (TKI) that inhibits both wild-type and mutated KIT, BTK, ABL1, ABL2, and other targets (Valent et al., *Journal of Allergy and Clinical Immunology* 149.6 (2022): 1866-1874), included 15 subjects with AdvSM and 18 subjects with ISM. Results did not support continuing clinical development in patients with ISM, in part due to toxicities that led to dose reductions (Verstovsek et al., *Clinical Cancer Research* 14.12 (2008): 3906-3915.2008). Overall, 34% of subjects discontinued treatment due to toxicity. Pleural effusion was the most common grade 3 adverse event (10% of patients overall). Dasatinib warnings and precautions include myelosuppression and bleeding events; fluid retention, sometimes severe, including pleural effusions; cardiovascular events; pulmonary arterial hypertension; QT interval prolongation; severe dermatologic reactions; tumor lysis syndrome; embryo-fetal toxicity and effects on growth and development of pediatric patients (SPRYCEL package insert).

Recently, avapritinib, a targeted inhibitor of mutated KIT approved for treatment of patients with AdvSM (at the dose of 200 mg QD) was evaluated at lower doses (due to safety concerns) in patients with ISM (Gotlib et al., *NEJM evidence* 2.6 (2023): EVIDoa2200339). The randomized study led to registration of avapritinib for patients with ISM at the dose of 25 mg QD (Chifotides et al., *Clinical Lymphoma, Myeloma and Leukemia*, doi.org/10.1016/j.clml.2024.06.005). Even at this low dosage, adverse reactions led to dose interruptions in 5% of the ISM patients on avapritinib (AYVAKIT package insert). While avapritinib has shown some control of aberrant mast cell proliferation in patients with ISM, the benefits on symptom response assessment were modest in ISM patients, as approximately half of the treated subjects failed to achieve a mean symptom score reduction of 30%, and only about a third of the subject achieved a 50% reduction within the first 6 months of treatment (Gotlib et al., *NEJM evidence* 2.6 (2023): EVIDoa2200339). The limited ability of this drug to alleviate symptoms in ISM patients highlights the significant unmet need in the field for new therapies.

Current research shows that treating ISM mainly focuses on blocking the growth signals caused by the mutated KIT gene, such as avapritinib, with limited efficacy on symptoms (Valent et al., *Journal of Allergy and Clinical Immunology* 149.6 (2022): 1866-1874; Akin et al., *J Allergy Clin Immunol.* 2022:149(6):1912-1918; Chifotides et al., *Clinical Lymphoma, Myeloma and Leukemia*, doi.org/10.1016/j.clml.2024.06.005). Clearly, such approach does not address the need for symptom control. Therefore, there is a high unmet need in patients with ISM, a distinct disease with debilitating constitutional symptoms that impair their ability to perform daily activities, for a novel treatment option that can directly control the symptoms of ISM and is well-tolerated and suitable for chronic administration. The present invention meets this need.

SUMMARY

In one aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

In another aspect, the disclosure encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period. In some embodiments, the total symptom score reduction is calculated by comparing the total symptom score after the treatment period to the total symptom score at baseline (i.e., prior to the treatment period). In some embodiments, the total symptom score is calculated based on the responses to the eleven questions listed in ISM-TSAF (Table 2). In some embodiments, the total symptom score is calculated based on the responses to the questions 1-8 listed in SISM-TSAF (Table 3).

In another aspect, the disclosure encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject expresses constitutively activated KIT.

In another aspect, the disclosure encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject expresses constitutively activated KIT, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period. In some embodiments, the total symptom score reduction is calculated by comparing the total symptom score after the treatment period to the total symptom score at baseline (i.e., prior to the treatment period). In some embodiments, the total symptom score is calculated based on the responses to the eleven questions listed in ISM-TSAF (Table 2). In some embodiments, the total symptom score is calculated based on the responses to the questions 1-8 listed in SISM-TSAF (Table 3). In another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject expresses constitutively activated KIT on mast cells.

In another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject expresses constitutively activated KIT on mast cells, wherein the human subject expresses constitutively activated KIT, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period. In some embodiments, the total symptom score reduction is calculated by comparing the total symptom score after the treatment period to the total symptom score at baseline (i.e., prior to the treatment period). In some embodiments, the total symptom score is calculated based on the responses to the eleven questions listed in ISM-TSAF (Table 2). In some embodiments, the total symptom score is calculated based on the responses to the questions 1-8 listed in SISM-TSAF (Table 3).

In another aspect, the invention encompasses a method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the peak plasma concentration of the BTK inhibitor in the human subject following administration is at least 125 ng/ml.

In yet another aspect, the invention encompasses a method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the peak plasma concentration of the BTK inhibitor in the human subject following administration is at least 125 ng/ml, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period. In some embodiments, the total symptom score reduction is calculated by comparing the total symptom score after the treatment period to the total symptom score at baseline (i.e., prior to the treatment period). In some embodiments, the total symptom score is calculated based on the responses to the eleven questions listed in ISM-TSAF (Table 2). In some embodiments, the total symptom score is calculated based on the responses to the questions 1-8 listed in SISM-TSAF (Table 3).

In some embodiments, the peak plasma concentration of the BTK inhibitor is at least 150 ng/ml. In some embodiments, the peak plasma concentration of the BTK inhibitor is at least 175 ng/ml. In some embodiments, the peak plasma concentration of the BTK inhibitor is about 200 ng/ml. In some embodiments, the peak plasma concentration of the BTK inhibitor is about 225 ng/ml. In some embodiments, the peak plasma concentration of the BTK inhibitor is about 250 ng/ml. In some embodiments, the peak plasma concentration of the BTK inhibitor is about 275 ng/ml. In some embodiments, the peak plasma concentration of the BTK inhibitor is in a range of 125 to 500 ng/ml, 150 to 475 ng/ml, 175 to 450 ng/ml, 200 to 425 ng/ml, 225 to 400 ng/ml, 250 to 375 ng/ml, 275 to 350 ng/ml, or 300 to 325 ng/ml.

In another aspect, the invention encompasses a method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the BTK inhibitor inhibits at least 90% basophil activation following administration as measured by basophil CD63 expression in the human subject.

In another aspect, the invention encompasses a method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the BTK inhibitor inhibits at least 90% basophil activation following administration as measured by basophil CD63 expression in the human subject, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period. In some embodiments, the total symptom score reduction is calculated by comparing the total symptom score after the treatment period to the total symptom score at baseline (i.e., prior to the treatment period). In some embodiments, the total symptom score is calculated based on the responses to the eleven questions listed in ISM-TSAF (Table 2). In some embodiments, the total symptom score is calculated based on the responses to the questions 1-8 listed in SISM-TSAF (Table 3).

In some embodiments, the basophil activation test is illustrated in Example 1. In some embodiments, the BTK inhibitor inhibits about 95% of basophil activation measured by CD63 expression in the human subject. In some embodiments, the BTK inhibitor inhibits at least 95% of basophil activation measured by CD63 expression in the human subject. In some embodiments, the BTK inhibitor inhibits at least 98% of basophil activation measured by CD63 expression in the human subject. In some embodiments, the BTK inhibitor inhibits at least 99% of basophil activation measured by CD63 expression in the human subject. In some embodiments, the BTK inhibitor inhibits about 80% of basophil activation measured by CD63 expression in the human subject. In some embodiments, the BTK inhibitor inhibits about 85% of basophil activation measured by CD63 expression in the human subject. In some embodiments, the BTK inhibitor inhibits about 90% of basophil activation measured by CD63 expression in the human subject. In some embodiments, the BTK inhibitor inhibits about 95% of basophil activation measured by CD63 expression in the human subject. In some embodiments, the BTK inhibitor inhibits about 99% of basophil activation measured by CD63 expression in the human subject. In some embodiments, the peak plasma concentration (Cmax) of the BTK inhibitor in the human subject following administration is at least 125 ng/ml. In some embodiments, the basophil activation comprises basophil degranulation.

In another aspect, the invention encompasses a method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the peak plasma concentration of the BTK inhibitor in the human subject following administration is at least 125 ng/ml, wherein the BTK inhibitor inhibits at least 90% basophil activation following administration as measured by basophil CD63 expression in the human subject.

In another aspect, the invention encompasses a method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the peak plasma concentration of the BTK inhibitor in the human subject following administration is at least 125 ng/ml, wherein the BTK inhibitor inhibits at least 90% basophil activation following administration as measured by basophil CD63 expression in the human subject, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period. In some embodiments, the total symptom score reduction is calculated by comparing the total symptom score after the treatment period to the total symptom score at baseline (i.e., prior to the treatment period). In some embodiments, the total symptom score is calculated based on the responses to the eleven questions listed in ISM-TSAF (Table 2). In some embodiments, the total symptom score is calculated based on the responses to the questions 1-8 listed in SISM-TSAF (Table 3).

In some embodiments, the BTK inhibitor is administered in combination with best supportive care (BSC).

In some embodiments, mast cells of the human subject have a lower threshold for degranulation compared to normal mast cells.

In some embodiments, the BTK inhibitor inhibits BTK with IC50 less than 5 nM. In some embodiments, the BTK inhibitor inhibits BTK with IC50 less than 4 nM. In some embodiments, the BTK inhibitor inhibits BTK with IC50 less than 3 nM. In some embodiments, the BTK inhibitor inhibits BTK with IC50 less than 2 nM. In some embodiments, the BTK inhibitor inhibits BTK with IC50 less than 1 nM. In some embodiments, the BTK inhibitor inhibits BTK with IC50 about 5 nM. In some embodiments, the BTK inhibitor inhibits BTK with IC50 about 4 nM. In some embodiments, the BTK inhibitor inhibits BTK with IC50 about 3 nM. In some embodiments, the BTK inhibitor inhibits BTK with IC50 about 2 nM. In some embodiments, the BTK inhibitor inhibits BTK with IC50 about 1 nM.

In some embodiments, the BTK inhibitor inhibits BTK with EC50 less than 25 nM. In some embodiments, the BTK inhibitor inhibits BTK with EC50 less than 20 nM. In some embodiments, the BTK inhibitor inhibits BTK with EC50 less than 15 nM. In some embodiments, the BTK inhibitor inhibits BTK with EC50 less than 10 nM. In some embodiments, the BTK inhibitor inhibits BTK with EC50 less than 5 nM. In some embodiments, the BTK inhibitor inhibits BTK with EC50 about 25 nM. In some embodiments, the BTK inhibitor inhibits BTK with EC50 about 20 nM. In some embodiments, the BTK inhibitor inhibits BTK with EC50 about 15 nM. In some embodiments, the BTK inhibitor inhibits BTK with EC50 about 10 nM. In some embodiments, the BTK inhibitor inhibits BTK with EC50 about 5 nM.

In some embodiments, the BTK inhibitor reduces serum tryptase levels by at least 20%, at least 25%, at least 30%, at least 35, at least 40%, at least 45%, at least 50%, at least 55%, at least 60%, at least 65%, at least 70%, at least 75%, at least 80%, at least 85%, at least 90%, or at least 95% in the human subject.

In some embodiments, the BTK inhibitor reduces serum tryptase levels by about 20%, about 25%, about 30%, about 35, about 40%, about 45%, about 50%, about 55%, about 60%, about 65%, about 70%, about 75%, about 80%, about 85%, about 90%, or about 95% in the human subject.

In some embodiments, the BTK inhibitor is selective BTK inhibitor. In some embodiments, the BTK inhibitor is irreversible covalent inhibitor.

In some embodiments, the BTK inhibitor is administered in an amount sufficient to reduce release of histamine and/or cytokines from mast cells and/or basophil cells in the human subject.

In some embodiments, the BTK inhibitor is administered in an amount sufficient to inhibit FcεRI-mediated calcium signaling associated with mast cell degranulation in the human subject.

In some embodiments, the BTK inhibitor is administered in an amount sufficient to inhibit MRGPRX1-mediated cytokine production associated with mast cell degranulation in the human subject.

In some embodiments, the BTK inhibitor is administered in an amount sufficient to inhibit histamine release in the human subject.

In some embodiments, the BTK inhibitor is administered in an amount sufficient to inhibit tryptase release in the human subject.

In some embodiments, the BTK inhibitor is administered in an amount sufficient to inhibit pro-inflammatory cytokine release and/or production by mast cells and basophils in the human subject.

In some embodiments, the BTK inhibitor is administered in an amount sufficient to reduce degranulation of mast cells and/or basophil cells in the human subject.

In some embodiments, the BTK inhibitor is administered in an amount sufficient to reduce release of leukotrienes.

In some embodiments, the BTK inhibitor is administered in an amount sufficient to reduce release of prostaglandins.

In some embodiments, the BTK inhibitor is administered in an amount sufficient to reduce release of kinins, serotonin, heparin and serine proteases.

In some embodiments, the BTK inhibitor is administered in an amount sufficient to reduce release of leukotrienes from mast cells/basophils in the human subject.

In some embodiments, the BTK inhibitor is administered in an amount sufficient to reduce release of prostaglandins from mast cells/basophils in the human subject.

In some embodiments, the BTK inhibitor is administered in an amount sufficient to reduce release of kinins, serotonin, heparin and serine proteases from mast cells/basophils in the human subject.

In some embodiments, the human subject has a KIT D816V mutation. In some embodiments, the human subject does not have additional pathogenic mutations.

In some embodiments, the human subject has a KIT D816V mutation with a variant allele frequency (VAF) of at least 0.05, at least 0.1, at least 0.15, at least 0.20, at least 0.25, at least 0.30, at least 0.35, at least 0.40, at least 0.45, at least 0.50, at least 0.55, or at least 0.60.

In some embodiments, the human subject has a KIT D816V mutation with a variant allele frequency (VAF) of about 0.05, about 0.1, about 0.15, about 0.20, about 0.25, about 0.30, about 0.35, about 0.40, about 0.45, about 0.50, about 0.55, or about 0.60.

In some embodiments, the human subject has one or more mutation in a gene selected from the group consisting of ASXL1, CBL, DNMT3A, EZH2, JAK2, KRAS, NRAS, SF3B1, RUNX1, SF3B1, SRSF2, TET2, and combinations thereof.

In some embodiments, the human subject does not have a KIT D816V mutation.

In some embodiments, the KIT D816V mutation results in constitutive activation of KIT.

In some embodiments, the constitutive activation of KIT results in the aggregation of mast cells in bone marrow and/or peripheral tissue of the human subject which degranulate upon exposure to a lower antigenic stimulus than healthy mast cells.

In some embodiments, the BTK inhibitor is administered in an amount sufficient to reduce IgE-mediated FcεRI activity.

In some embodiments, the BTK inhibitor is administered in an amount sufficient to inhibit MRGPRX2-mediated mast cell cytokine production in the human subject.

In some embodiments, the IgE-mediated FcεRI activity is associated with antigen binding to IgE.

In some embodiments, the IgE-mediated FcεRI activity is associated with monomeric IgE binding to FcεRI.

In some embodiments, the BTK inhibitor is administered in an amount sufficient to reduce non-IgE-mediated FcεRI activity.

In some embodiments, the BTK inhibitor is administered in an amount sufficient to reduce IgE-mediated FcεRI activity from mast cells/basophils in the human subject.

In some embodiments, the BTK inhibitor is administered in an amount sufficient to inhibit MRGPRX2-mediated mast cell cytokine production from mast cells/basophils in the human subject.

In some embodiments, the IgE-mediated FcεRI activity is associated with antigen binding to IgE from mast cells/basophils in the human subject.

In some embodiments, the IgE-mediated FcεRI activity is associated with monomeric IgE binding to FcεRI from mast cells/basophils in the human subject.

In some embodiments, the BTK inhibitor is administered in an amount sufficient to reduce non-IgE-mediated FcεRI activity from mast cells/basophils in the human subject.

In some embodiments, the IgE-mediated FcεRI activity is regulated by BTK activity.

In some embodiments, administering the BTK inhibitor reduces mast cell and/or basophil cell activation. In some embodiments, administering the BTK inhibitor reduces mast cell and/or basophil cell activation, wherein mast cell and/or basophil cell activation is IgE dependent. In some embodiments, administering the BTK inhibitor reduces mast cell and/or basophil cell degranulation. In some embodiments, administering the BTK inhibitor reduces mast cell and/or basophil cell degranulation, wherein mast cell and/or basophil cell degranulation is IgE dependent.

In some embodiments, administering the BTK inhibitor reduces trafficking of aberrant immature mast cells from bone marrow to the skin and gastrointestinal tract, thereby reducing the number of aberrant mast cells in the skin and gastrointestinal tract.

In some embodiments, administering the BTK inhibitor reduces the frequency of anaphylactic reactions in the human subject. In some embodiments, administering the BTK inhibitor reduces the severity of anaphylactic reactions in the human subject. In some embodiments, the anaphylactic reactions are allergen induced anaphylactic reactions.

In some embodiments, the BTK inhibitor is administered twice daily at a dose selected from the group consisting of 10 mg, 25 mg, 50 mg, 75 mg, 100 mg, 150 mg, 200 mg, 250 mg, and 300 mg. In some embodiments, the BTK inhibitor is administered twice daily at a dose of 10 mg. In some embodiments, the BTK inhibitor is administered twice daily at a dose of 25 mg. In some embodiments, the BTK inhibitor is administered twice daily at a dose of 50 mg. In some embodiments, the BTK inhibitor is administered twice daily at a dose of 75 mg. In some embodiments, the BTK inhibitor is administered twice daily at a dose of 100 mg. In some embodiments, the BTK inhibitor is administered twice daily at a dose of 150 mg. In some embodiments, the BTK inhibitor is administered twice daily at a dose of 200 mg. In some embodiments, the BTK inhibitor is administered twice daily at a dose of 250 mg. In some embodiments, the BTK inhibitor is administered twice daily at a dose of 300 mg. In some embodiments, the BTK inhibitor is orally administered.

In some embodiments, the human subject has previously failed prior treatment for ISM. In some embodiments, the prior treatment is avapritinib. In some embodiments, the human subject has previously failed treatment of a KIT inhibitor selected from the group consisting of regorafenib, sorafenib, imatinib, ilorasertib, sunitinib, pazopanib, lenvatinib, dasatinib, bezuclastinib, exarafenib, nintedanib, telatinib, avapritinib, TPX-0022, crenolanib, midostaurin, nilotinib, and pharmaceutically acceptable salts thereof. In some embodiments, the human subject is a non-responder to prior treatment for ISM. In some embodiments, the human subject is ISM treatment naïve. In some embodiments, the human subject has a refractory or relapsed ISM. In some embodiments, the human subject is treatment resistant to prior treatment for ISM. In some embodiments, the BTK inhibitor is administered in combination with the best supportive care for ISM. In some embodiments, the BTK inhibitor is administered as a monotherapy. In some embodiments, the human subject is resistant to best supportive care for ISM. In some embodiments, the prior treatment for ISM is selected from the group consisting of histamine H1 blockers, histamine H2 blockers, leukotriene inhibitors, cromolyn sodium, corticosteroids and omalizumab.

In yet another aspect, the disclosure encompasses a method of reducing or alleviating at least one symptom selected from the group consisting of fatigue, abdominal pain, diarrhea, nausea, skin spots, itching, flushing, brain fog, headache, dizziness, bone pain, and combinations thereof in a human subject diagnosed with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

In yet another aspect, the invention encompasses a method of reducing or alleviating at least one symptom selected from the group consisting of fatigue, abdominal pain, diarrhea, nausea, skin spots, itching, flushing, brain fog, headache, dizziness, bone pain, and combinations thereof in a human subject diagnosed with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

In yet another aspect, the invention encompasses a method of reducing or alleviating at least one symptom selected from the group consisting of fatigue, abdominal pain, diarrhea, nausea, skin spots, itching, flushing, brain fog, headache, dizziness, bone pain, and combinations thereof in a human subject diagnosed with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period.

In yet another aspect, the disclosure encompasses a BTK inhibitor for use in reducing or alleviating at least one symptom selected from the group consisting of fatigue, abdominal pain, diarrhea, nausea, skin spots, itching, flushing, brain fog, headache, dizziness, bone pain, and combinations thereof in a human subject diagnosed with indolent systemic mastocytosis (ISM), wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. The human subject may have a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period.

In yet another aspect, the invention encompasses a method of reducing or alleviating a symptom selected from the group consisting of muscle pain, difficulty concentrating, difficulty remembering, runny nose, nasal congestion, wheezing, shortness of breath, throat itching, heart palpitations, diarrhea, and combinations thereof in a human subject with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

In yet another aspect, the invention encompasses a method of reducing or alleviating at least one symptom selected from the group consisting of muscle pain, wheezing, shortness of breath, heart palpitations, nasal congestion, runny nose, throat itching, difficulty concentrating, difficulty remembering, diarrhea and combinations thereof in a human subject diagnosed with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject has a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period.

In yet another aspect, the disclosure encompasses a BTK inhibitor for use in reducing or alleviating at least one symptom selected from the group consisting of muscle pain, wheezing, shortness of breath, heart palpitations, nasal congestion, runny nose, throat itching, difficulty concentrating, difficulty remembering, diarrhea and combinations thereof in a human subject diagnosed with indolent systemic mastocytosis (ISM) wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. The human subject may have a total symptom score which is reduced by at least 18% after a treatment period of at least 12 weeks. In some embodiments, the total symptom score of the human subject is reduced by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% after the treatment period.

The invention encompasses a method of reducing or alleviating a symptom selected from the group consisting of itching, skin redness and/or swelling, flushing, diarrhea and/or loose stools, fatigue and/or exhaustion, headache, muscle and/or joint pain, difficulty concentrating, and combinations thereof in a human subject with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

The disclosure encompasses a method of reducing or alleviating a symptom selected from the group consisting of itching, skin redness and/or swelling, flushing, diarrhea and/or loose stools, fatigue and/or exhaustion, headache, muscle and/or joint pain, difficulty concentrating, and combinations thereof in a human subject with indolent systemic mastocytosis (ISM) comprising administering to the human subject an amount of a Bruton's Tyrosine Kinase (BTK) inhibitor effective to reduce or alleviate the symptom, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the human subject has a total symptom score which is reduced by at least 18% after a treatment period of at least 12 weeks.

The disclosure encompasses BTK inhibitor for use in reducing or alleviating a symptom selected from the group consisting of itching, skin redness and/or swelling, flushing, diarrhea and/or loose stools, fatigue and/or exhaustion, headache, muscle and/or joint pain, difficulty concentrating, and combinations thereof in a human subject with indolent systemic mastocytosis (ISM), wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. The human subject may have a total symptom score which is reduced by at least 18% after a treatment period of at least 12 weeks.

In some embodiments, the total symptom score is calculated based on the responses to the eleven questions listed in ISM-TSAF (Table 2).

In some embodiments, the total symptom score is calculated based on the responses to the questions 1-8 listed in SISM-TSAF (Table 3). In some embodiments, the total symptom score calculated based on the responses to questions 1-8 of SISM-TSAF is highly correlated with the total symptom score calculated based on the responses to questions 1-11 of ISM-TSAF (Table 2).

In some embodiments, the total symptom score is an average of daily total symptom score, such as a 7-day rolling average of daily total symptom score, a 10-day rolling average of daily total symptom score, a 14-day rolling average of daily total symptom score, or a 21-day rolling average of daily total symptom score.

In some embodiments, the total symptom score of the human subject is reduced by at least 20% after the treatment period.

In some embodiments, the total symptom score of the human subject is reduced by at least 25% after the treatment period.

In some embodiments, the total symptom score of the human subject is reduced by at least 30% after the treatment period.

In some embodiments, the total symptom score of the human subject is reduced by at least 35% after the treatment period.

In some embodiments, the total symptom score of the human subject is reduced by at least 40% after the treatment period.

In some embodiments, the total symptom score of the human subject is reduced by at least 45% after the treatment period.

In some embodiments, the total symptom score of the human subject is reduced by at least 50% after the treatment period.

In some embodiments, the total symptom score of the human subject is reduced by at least 55% after the treatment period.

In some embodiments, the total symptom score of the human subject is reduced by at least 60% after the treatment period.

In some embodiments, the total symptom score of the human subject is reduced by at least 65% after the treatment period.

In some embodiments, the total symptom score of the human subject is reduced by at least 70% after the treatment period.

In some embodiments, the total symptom score of the human subject is reduced by at least 75% after the treatment period.

In some embodiments, the total symptom score of the human subject is reduced by at least 80% after the treatment period.

In some embodiments, the total symptom score of the human subject is reduced by at least 85% after the treatment period.

In some embodiments, the total symptom score of the human subject is reduced by at least 90% after the treatment period.

In some embodiments, the total symptom score of the human subject is reduced by at least 95% after the treatment period.

In some embodiments, the total symptom score reduction is calculated by comparing to the total symptom score prior to the treatment period (baseline total symptom score).

In some embodiments, the treatment period is about 12 weeks, about 24 weeks, about 36 weeks, about 48 weeks, or about 60 weeks.

In some embodiments, the treatment period is at least 12 weeks, at least 24 weeks, at least 36 weeks, at least 48 weeks, or at least 60 weeks.

In some embodiments, the BTK inhibitor is administered in an amount sufficient to reduce release of histamine.

In some embodiments, the BTK inhibitor is administered in an amount sufficient to reduce release of leukotrienes.

In some embodiments, the BTK inhibitor is administered in an amount sufficient to reduce release of tryptase.

In some embodiments, the BTK inhibitor is administered in an amount sufficient to reduce release of prostaglandins.

In some embodiments, the BTK inhibitor is administered in an amount sufficient to reduce release of kinins, serotonin, heparin and serine proteases.

In some embodiments, the human subject has previously failed prior treatment for ISM. In some embodiments, the prior treatment is avapritinib. In some embodiments, the human subject is a non-responder to prior treatment for ISM. In some embodiments, the human subject is ISM treatment naïve.

In some embodiments, administering the BTK inhibitor reduces the frequency of anaphylactic reactions in the human subject. In some embodiments, administering the BTK inhibitor reduces the severity of anaphylactic reactions in the human subject. In some embodiments, the anaphylactic reactions are allergen induced anaphylactic reactions.

In some embodiments, the human subject has a KIT D816V mutation. In some embodiments, the human subject does not have a KIT D816V mutation. In some embodiments, the KIT D816V mutation results in constitutive activation of KIT. In some embodiments, the constitutive activation of KIT results in the aggregation of mast cells in bone marrow and/or peripheral tissue of the human subject which degranulate upon exposure to a lower antigenic stimulus than healthy mast cells.

In some embodiments, the BTK inhibitor is administered twice daily at a dose selected from the group consisting of 10 mg, 25 mg, 50 mg, 75 mg, 100 mg, 150 mg, 200 mg, 250 mg, and 300 mg. In some embodiments, the BTK inhibitor is administered once daily at a dose selected from the group consisting of 10 mg, 25 mg, 50 mg, 75 mg, 100 mg, 150 mg, 200 mg, 250 mg, and 300 mg. In some embodiments, the BTK inhibitor is orally administered. In some embodiments, the BTK inhibitor is administered once daily at a dose of 10 mg. In some embodiments, the BTK inhibitor is administered once daily at a dose of 25 mg. In some embodiments, the BTK inhibitor is administered once daily at a dose of 50 mg. In some embodiments, the BTK inhibitor is administered once daily at a dose of 75 mg. In some embodiments, the BTK inhibitor is administered once daily at a dose of 100 mg. In some embodiments, the BTK inhibitor is administered once daily at a dose of 150 mg. In some embodiments, the BTK inhibitor is administered once daily at a dose of 200 mg. In some embodiments, the BTK inhibitor is administered once daily at a dose of 250 mg. In some embodiments, the BTK inhibitor is administered once daily at a dose of 300 mg. In some embodiments, the BTK inhibitor is administered twice daily at a dose of 10 mg. In some embodiments, the BTK inhibitor is administered twice daily at a dose of 25 mg. In some embodiments, the BTK inhibitor is administered twice daily at a dose of 50 mg. In some embodiments, the BTK inhibitor is administered twice daily at a dose of 75 mg. In some embodiments, the BTK inhibitor is administered twice daily at a dose of 100 mg. In some embodiments, the BTK inhibitor is administered twice daily at a dose of 150 mg. In some embodiments, the BTK inhibitor is administered twice daily at a dose of 200 mg. In some embodiments, the BTK inhibitor is administered twice daily at a dose of 250 mg. In some embodiments, the BTK inhibitor is administered twice daily at a dose of 300 mg.

In some embodiments, the method further comprises assessing the severity of the symptom prior to administration of the BTK inhibitor. In some embodiments, the method further comprises assessing the severity of the symptom after administration of the BTK inhibitor. In some embodiments, the severity of the symptom is determined by self-assessment. In some embodiments, the severity of the symptom is determined by self-reporting.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein the BTK inhibitor is not mutagenic or genotoxic. In some embodiments, "mutagenic" refers to something that causes mutations, which are changes in the DNA sequence of an organism's genome. Mutagenic agents can include chemicals, radiation, or even certain biological agents. These agents interact with DNA in a way that causes alterations, which can lead to changes in cellular processes, and in some cases, lead to diseases such as cancer. In some embodiments, "genotoxic" refers to any substance or agent that damages the genetic material within a cell, affecting its integrity. Genotoxic agents may cause mutations, chromosomal fragmentation, or other types of DNA damage, which can lead to cancer, cell death, or inherited genetic diseases if the damage is not repaired.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein the BTK inhibitor is more efficacious than avapritinib in treating ISM.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein the BTK inhibitor does not cause intracranial hemorrhage or cognitive adverse reactions. In some embodiments, the cognitive adverse reactions are negative effects on cognitive functions (such as memory, attention, problem-solving, and executive functioning) that result from certain medications, treatments, or medical conditions. In some embodiments, the cognitive adverse reactions include memory impairment, difficulty focusing, slowed thinking, confusion or disorientation, and impairments in planning, organizing, and completing tasks.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein administration of the BTK inhibitor to the human subject does not cause photosensitivity. In some embodiments, photosensitivity refers to the unusually sensitive skin to light compared to a normal human subject. In some embodiments, photosensitivity affect sun-exposed areas of the skin, such as: face, neck, arms, and hands.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein administration of the BTK inhibitor to the human subject does not cause abdominal discomfort, dysgeusia, or changes in hair color.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein administration of the BTK inhibitor to the human subject reduces or eliminates abdominal discomfort, dysgeusia, or changes in hair color.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein administration of the BTK inhibitor to the human subject does not cause fluid retention, including pleural effusions; cardiovascular events; pulmonary arterial hypertension; QT interval prolongation; or severe dermatologic reactions.

In yet another aspect, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof, wherein administration of the BTK inhibitor to the human subject reduces or eliminates fluid retention, including pleural effusions; cardiovascular events; pulmonary arterial hypertension; QT interval prolongation; or severe dermatologic reactions.

BRIEF DESCRIPTION OF THE DRAWINGS

As used herein, the term "Compound 128" is abbreviated as "CP-128" or "Cmpd 128".

FIG. 15A shows the fold change over unstimulated control for MRGPRX2-induced BTK phosphorylation in three donors with ISM-like mast cell conditions. FIG. 15B shows the percentage of control for MRGPRX2-induced cytokine production in three donors with ISM-like mast cell conditions. FIG. 15C shows the percentage of control for MRGPRX2-induced cytokine production across different agonists and Compound 128 concentrations in one donor with ISM-like mast cell conditions.

FIGS. 18 A-D show return of degranulation after Compound 128 exposure.

DETAILED DESCRIPTION

Figure 1:
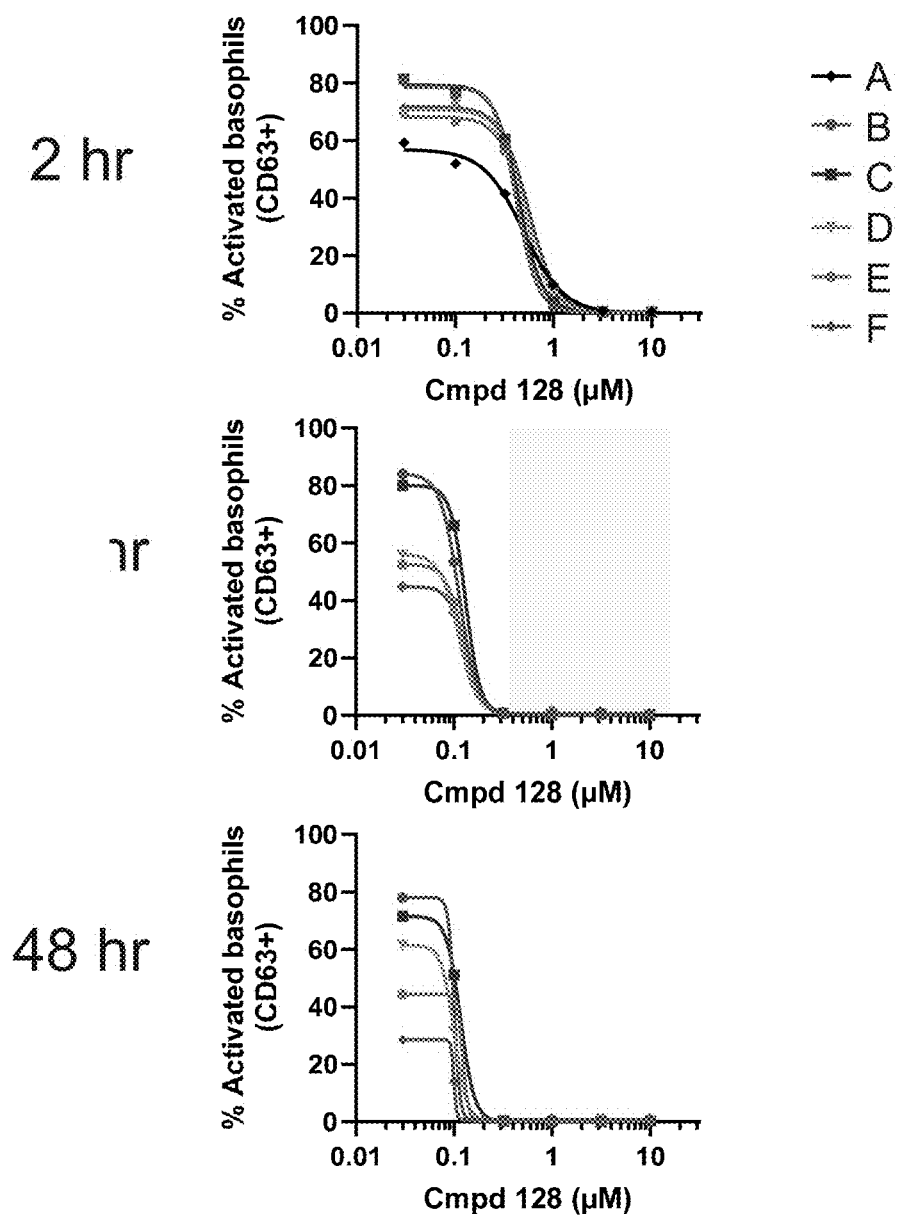
FIG. 1 is a graph showing percent of activated basophils (CD63+) 2 hours, 24 hours, and 48 hours after exposure to different BTK inhibitor (Compound 128) concentrations.

While preferred embodiments of the disclosure are shown and described herein, such embodiments are provided by way of example only and are not intended to otherwise limit the scope of the disclosure. Various alternatives to the described embodiments of the disclosure may be employed in practicing the disclosure.

In certain aspects, the invention relates to treating ISM in a human subject having at least one of the WHO 2016 criteria used for diagnosis and classification of different subtypes of mastocytosis (Valent (2017), Blood 129, 1420-1427). In certain aspects, the invention described herein relates to clonal mastocytosis, which can result from the presence of a same mutation across a sub-population of mast cells. Without wishing to be bound by theory, in certain aspects, the invention described herein relates to ISM associated with accumulation of neoplastic mature mast cells. In certain aspects, the invention relates to methods and compositions for treating a human subject, having at least one mast cell having KIT D816V mutation. Mast cells harboring a KIT D816V mutation can exhibit lower threshold for activating/degranulation from Fc epsilon R One (FcεRI) signaling. In certain embodiments, such cells can be described as "twitchy." In certain embodiments, constitutively activated ISM mast cells can be caused by binding of ISM mast cell FcεRI receptors to circulating monomeric immunoglobulin E (IgE) coupled with activated KIT signaling through KIT mutations (e.g. D816V+ and others). In some embodiments, human subjects having ISM can have chronic and highly debilitating constitutional symptoms.

In certain aspects, the invention relates to treating ISM in a human subject by administering a Bruton's Tyrosine Kinase (BTK) inhibitor. BTK is a non-receptor tyrosine kinase that belongs to the Tec family and has an important function in multiple hematopoietic cell types (Schmidt (2004) Int. Arch. Allergy Immunol. 134, 65-78). use of BTK inhibitors in humans can be complicated by toxicities and/or adverse events such as severe infections, cardiac complications, and liver dysfunction. In some cases, off-target effects can lead to adverse immune responses, negating the intended therapeutic benefits and raising safety concerns. For example, administration of ibrutinib is associated with a heightened risk of atrial fibrillation, hypertension, major bleeding events, and cytopenias. The cardiovascular risks, in particular, such as atrial fibrillation, raised significant concerns, leading to trial discontinuations or restricted usage in certain patient populations. These adverse effects were often severe enough to outweigh the potential therapeutic benefits, ultimately impacting the risk-benefit profile of the treatment and contributing to the decision to halt or adjust the clinical trial's course (Leong et al., The risk of atrial fibrillation with ibrutinib use: a systematic review and meta-analysis, *Blood* (2016) 128 (1): 138-140); Caron et al., Current understanding of bleeding with ibrutinib use: a systematic review and meta-analysis, *Blood Adv* (2017) 1 (12): 772-778).

Figure 10:
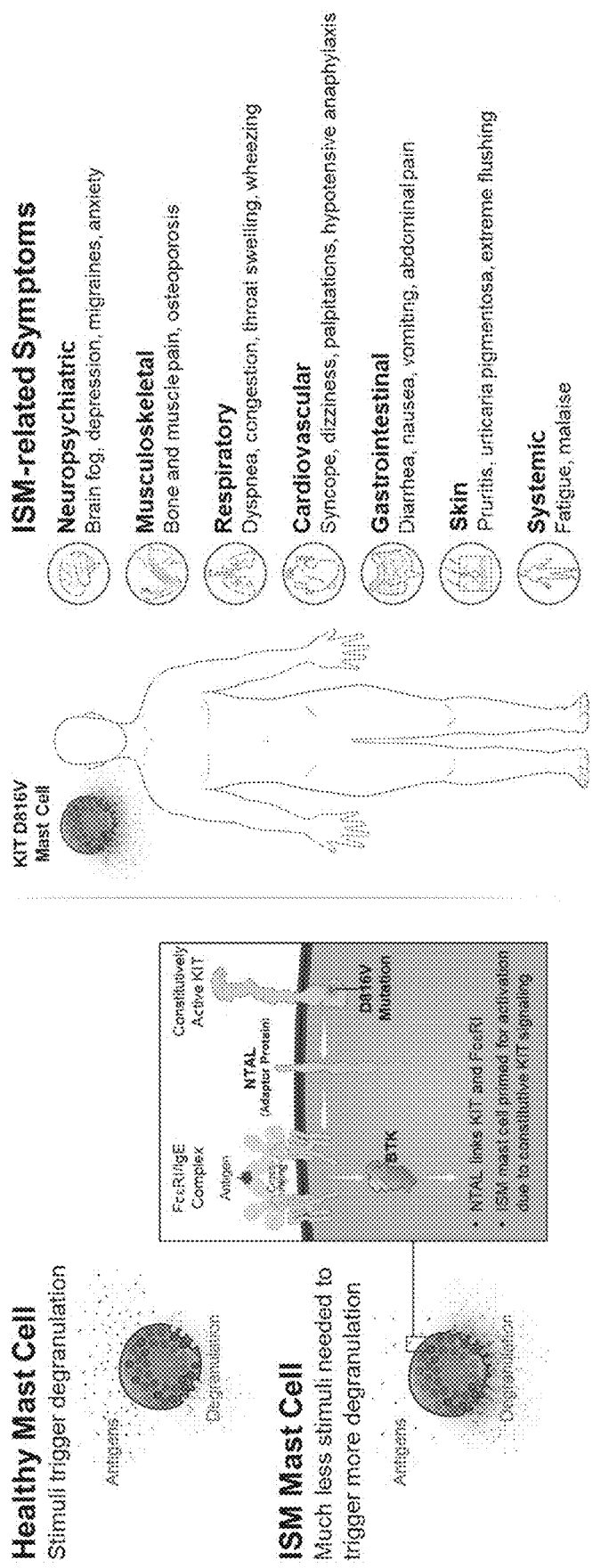
FIG. 10 is a diagram showing the role of BTK in aberrant ISM mast cells, connection between the KIT receptor and FcεRI signaling pathways along with typical systemic symptoms associated with ISM.

In certain aspects, the invention relates to the finding that the interconnection between these two signaling pathways in mutated KIT (D816V) mast cells lowers the antigen-mediated threshold for cell degranulation, resulting in "twitchy" mast cells. In certain aspects, binding of ISM mast cell FcεRI receptors to circulating monomeric IgE may be the cause of constitutively activated ISM mast cells, which in turn explains the continuous constitutional symptoms observed in the majority of patients with ISM. The BTK signaling pathway downstream of the FcεRI/IgE interaction is therefore important to the activation, degranulation and cytokine-driven inflammatory cascade triggered by mast cells and subsequently propagated by basophils. In some embodiments, the invention relates to the treatment of ISM, a disease of aberrant mast cell signaling (see FIG. 10), wherein mast cells are too easily triggered to degranulate and may become activated by either monomeric IgE or antigen-bound IgE, such treatment offers a novel therapeutic approach. In some embodiments, the invention relates to the treatment of ISM, wherein degranulation of the mast cells of the ISM patients are IgE dependent. In some embodiments, the invention relates to therapeutically targeting BTK with a BTK inhibitor to hinder mast cell and basophil degranulation, subsequent histamine, tryptase release and cytokine-driven inflammation thought to be causing the significant ISM-related symptoms.

Mast cells are located throughout the body in areas below the epithelium in connective tissues surrounding blood cells, smooth muscle, mucous and hair follicles. They are particularly abundant in tissues with frequent contact with the surrounding environment such as the skin, the linings of the esophagus, stomach and intestine (gastrointestinal tract), respiratory epithelium and certain ocular compartments (conjunctiva, uveal tract). They play an important role in the immune defense against bacteria and parasites. By releasing chemical "alarms" such as histamine, mast cells attract other key players of the immune defense system to areas of the body where they are needed. In healthy individuals, the symptoms associated with mast cell degranulation are often relatively mild and short-lived (e.g. tenderness, redness and histamine-driven itching around a healing dermal injury). Mast cells express a cell surface receptor, KIT (CD117), which is the receptor for SCF, a mast cell growth factor. In laboratory studies, SCF appears to be important for the proliferation of mast cells. Mutations of the gene coding for the KIT receptor (i.e. D816V), leading to constitutive signaling through the receptor is found in >95% of patients with systemic mastocytosis. KIT signaling amplifies FcεRI signaling by inducing NTAL phosphorylation, creating docking sites for cytosolic adapter molecules and the signaling enzymes, PLCγ and phosphoinositide (PI) 3-kinase. This leads to KIT signaling acting in synergy with FcεRI signaling to enhance intracellular calcium levels and PKC activation, resulting in greater degranulation and histamine release, which may be an underlying pathogenic driver of ISM symptoms. Inhibition of BTK potently inhibits PLCγ and calcium release leading to a block in mast cell degranulation with potential to neutralize the mast cell activating effects of KIT.

BTK is also a key component of FcεRI signaling in basophils. Basophils augment the signaling process initiated by mast cells. Basophils express a complete FcεRI, the surface expression of which directly correlates with free IgE concentration. Aggregation of FcεRI bound to IgE by multivalent antigen leads to basophil activation, granule exocytosis, and mediator release. As stated above, the BTK signaling pathway downstream of the FcεRI/IgE interaction may lead to the activation, degranulation and cytokine-driven inflammatory cascade triggered propagated by basophils.

Unless defined otherwise, all technical and scientific terms used herein have the same meaning as is commonly understood by one of skill in the art to which this disclosure belongs.

The term "best supportive care (BSC)" refers supportive therapies to control symptoms of ISM in patients. In some cases, the BSC includes one or more administration of one or more agents selected from the table below.

| Drug Class | Generic/Trade Name |
| --- | --- |
| H1 antihistamines | Loratidine/Claritin |
| | Diphenhydramine/Benadryl |
| | Cetirizine/Zyrtec |
| | Fexofenadine/Allegra |
| | Hydroxyzine/Vistaril/Atarax |
| | Rupatadine/Rupafin |
| | Ketotifen/Zaditor |
| H2 antihistamines | Cimetidine/Tagamet |
| | Famotidine/Pepcid |
| | Ranitidine/Zantac |
| Leukotriene inhibitors | Montelukast/Singulair |
| | Zafirlukast/Accolate |
| Corticosteroids | Prednisone/Deltasone |
| Cromolyn sodium | Cromoglicic acid/Nasalcrom/Gastrocrom |
| Anti-IgE antibody | Omalizumab/Xolair |
| Bisphosphonates for osteoporosis | Alendronate/Aledronic acid//Fosamax |
| | Risedronate/Risedronic acid/Actenol/Atelvia |
| | Ibandronate/Ibandronic acid/Boniva |
| | Pamidronic acid/Aredia |
| | Zoledronic acid/Reclast/Zometa |
| Other drugs for osteoporosis | Denosumab/Prolia |
| | Raloxifene/Evista |
| | Teriparatide/Forteo |
| Epinephrine for allergic reactions | Adrenalin/EpiPen |

The term "effective amount" or "therapeutically effective amount" or "amount sufficient" refers to that amount of an active pharmaceutical ingredient or combination of active pharmaceutical ingredients as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, and other factors which can readily be determined by one of ordinary skill in the art. The term also applies to a dose that will induce a particular response in target cells, (e.g. mast cells and basophils). The specific dose will vary depending on the particular compounds chosen, the dosing regimen to be followed, whether the compound is administered in combination with other compounds, timing of administration, the tissue to which it is administered, and the physical delivery system in which the compound is carried.

"Systemic Mastocytosis" is a type of mast cell disease, a rare disorder affecting both children and adults caused by the accumulation of functionally defective mast cells (also called mastocytes) and CD34+ mast cell precursors. People affected by mastocytosis are susceptible to a variety of symptoms, including gastrointestinal, skin, cardiovascular, neuropsychiatric, musculoskeletal, respiratory and systemic symptoms caused by the release of histamine and other pro-inflammatory substances from mast cells. When mast cells undergo degranulation, the substances (histamines, prostaglandins, leukotrienes) that are released, and subsequent proinflammatory cytokines that are produced, can cause a number of symptoms that can vary over time and can range in intensity from mild to severe. Because mast cells play a role in allergic reactions, the symptoms of mastocytosis often are similar to the symptoms of an allergic reaction. Signs and symptoms may include, but are not limited to fatigue, skin lesions (urticaria pigmentosa), pruritus (itching), flushing and dermatographic urticaria (skin writing), abdominal discomfort, nausea and vomiting, diarrhea, olfactive intolerance, ear/nose/throat inflammation, anaphylaxis (shock from allergic or immune causes), episodes of very low blood pressure (including shock) and faintness/dizziness, bone or muscle pain, decreased bone density or increased bone density (osteoporosis or osteosclerosis), migraine/headache, depression, ocular discomfort, increased stomach acid production causing peptic ulcers (increased stimulation of enterochromaffin cell and direct histamine stimulation on parietal cell), malabsorption (due to inactivation of pancreatic enzymes by increased acid), hepatosplenomegaly, brain fog, heart palpitations, dyspnea and wheezing. Signs and symptoms may include, those identified in Valent (2017) Blood 129, 1420-1427.

"Indolent systemic mastocytosis" (ISM) is most common variant of systemic mastocytosis. ISM patients frequently suffer from mast cell (MC) mediator-related symptoms, including brain fog, migraines, anxiety, bone and muscle pain, osteoporosis, dyspnea, congestion, throat swelling, wheezing, syncope, dizziness, palpitations, hypotensive anaphylaxis, diarrhea, nausea, vomiting, abdominal pain, pruritus, urticaria pigmentosa, extreme flushing, fatigue, and malaise (see FIG. 10). In some embodiments, the symptoms of ISM may be one or more symptoms listed in Table 2 and Table 3. This subtype of mastocytosis is characterized by a relatively stable clinical course compared to other types of mastocytosis (e.g. aggressive systemic mastocytosis), with a low burden of symptoms and a better overall patient prognosis.

Although the etiology of ISM is not fully understood, an activating mutation of KIT, usually KIT D816V, is found in the MCs of majority of ISM cases. This mutation probably accounts for the abnormal accumulation of MCs in organ(s)/tissue(s).

The term "in the human subject" or "in the human," when referring to the effects of the BTK inhibitors disclosed herein with regard to degranulation (including the release of histamine, tryptase, prostaglandins, leukotrienes, kinins, serotonin, heparin, and serine proteases), cytokine production, FcεRI activity, and inflammation, indicates that these effects can be assessed by in vitro or in vivo methods.

"Peak plasma concentration" (abbreviated as Cmax) is a pharmacokinetic term that refers to the highest concentration of a drug that is observed in the blood plasma after a dose is administered. This value represents the point at which the absorption rate of the drug equals its elimination rate.

"Pharmaceutically acceptable carrier" or "pharmaceutically acceptable excipient" is intended to include any and all solvents, dispersion media, coatings, antibacterial and antifungal agents, isotonic, and absorption delaying agents. The use of such media and agents for active pharmaceutical ingredients is well known in the art. Except insofar as any conventional media or agent is incompatible with the active pharmaceutical ingredient, its use in the therapeutic compositions of the disclosure is contemplated. Supplementary active ingredients can also be incorporated into the described compositions.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve proton transfer between the cocrystal and the drug, and instead involves intermolecular interactions, such as hydrogen bonding, aromatic ring stacking, or dispersive forces, between the cocrystal former and the drug in the crystal structure.

The terms "QD" means quaque die, once a day, or once daily. The terms "BID" mean bis in die, twice a day, or twice daily. The terms "TID" mean ter in die, three times a day, or three times daily. The terms "QID" mean quater in die, four times a day, or four times daily.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease, symptom or condition, or any combination thereof.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from between 1% and 15% of the stated number or numerical range.

BTK inhibitor compounds of the disclosure also include crystalline and amorphous forms of the any of the compounds in Table 1, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to herein.

Methods of Treating Indolent Systemic Mastocytosis

In certain aspects, the invention relates to the unexpected discovery that a BTK inhibitor can be used to treat indolent systemic mastocytosis and various symptoms associated therewith. Accordingly, in certain aspects, the disclosure relates to methods for treating indolent systemic mastocytosis by administering to a human subject in need thereof an effective amount of a BTK inhibitor, including any BTK inhibitor set forth in Table 1. In certain embodiments, the invention relates to the surprising finding that in addition to regulating the B Cell Receptor (BCR) on B cells, BTK also regulates the IgE FcεRI pathway involved in initiating mast cell and basophil degranulation, leading to histamine release and cytokine-driven inflammation. In certain embodiments, inhibition of BTK activity using any of the BTK inhibitors disclosed herein reduces mast cell degranulation. In certain embodiments, the mast cell degranulation is IgE dependent. In certain embodiments, inhibition of BTK activity using any of the BTK inhibitors disclosed herein reduces basophil degranulation. In certain embodiments, inhibition of BTK activity using any of the BTK inhibitors disclosed herein reduces degranulation (including release of histamine, tryptase, prostaglandins, leukotrienes, kinins, serotonin, heparin, and serine proteases), cytokine production and inflammation. Thus, BTK inhibitors disclosed herein can be used to inhibit release of one or more of the following: histamine, tryptase, prostaglandins, leukotrienes, kinins, serotonin, heparin, and serine proteases.

In certain aspects of the invention, one or more BTK inhibitors can be used to treat indolent systemic mastocytosis, optionally including the reducing or alleviating of one or more symptoms associated with systemic mastocytosis, including, but not limited to, fatigue, skin lesions (urticaria pigmentosa), itching, and dermatographic urticaria (skin writing), abdominal discomfort, nausea and vomiting, diarrhea, olfactive intolerance, ear/nose/throat inflammation, anaphylaxis (shock from allergic or immune causes), episodes of very low blood pressure (including shock) and faintness, bone or muscle pain, decreased bone density or increased bone density (osteoporosis or osteosclerosis), headache, depression, ocular discomfort, increased stomach acid production causing peptic ulcers (increased stimulation of enterochromaffin cell and direct histamine stimulation on parietal cell), malabsorption (due to inactivation of pancreatic enzymes by increased acid) and hepatosplenomegaly. In certain aspects of the invention, BTK inhibitors can be used to treat for indolent systemic mastocytosis, optionally including the reducing or alleviating of symptoms associated with indolent systemic mastocytosis, including fatigue, abdominal pain, diarrhea, nausea, skin spots, itching, flushing, brain fog, headache, dizziness, bone pain, and combinations thereof. In yet further aspects of the invention, BTK inhibitors can be used to treat for indolent systemic mastocytosis, optionally including the reducing or alleviating of symptoms associated with indolent systemic mastocytosis, including muscle pain, difficulty concentrating, runny nose, nasal congestion, wheezing, shortness of breath, throat itching, heart palpitations, diarrhea, and combinations thereof. In yet further aspects, BTK inhibitors can be used to treat for indolent systemic mastocytosis additionally, optionally including the reducing or alleviating of symptoms associated with indolent systemic mastocytosis, including itching, skin redness and/or swelling, flushing, diarrhea and/or loose stools, fatigue and/or exhaustion, headache, muscle and/or joint pain, difficulty concentrating, and combinations thereof.

In yet further aspects of the disclosure, BTK inhibitors can be used to treat for indolent systemic mastocytosis, optionally including the reducing or alleviating of skin symptoms, such as flushing, itching and/or spots. In yet further aspects of the disclosure, BTK inhibitors can be used to treat for indolent systemic mastocytosis, optionally including the reducing or alleviating of gastrointestinal symptoms, such as abdominal pain, diarrhea and/or nausea. In yet further aspects of the disclosure, BTK inhibitors can be used to treat for indolent systemic mastocytosis, optionally including the reducing or alleviating of neurocognitive symptoms such as brain fog, dizziness and/or headache. In yet further aspects of the disclosure, BTK inhibitors can be used to treat for indolent systemic mastocytosis, optionally including the reducing or alleviating of skeletal symptoms, such as bone pain and/or fatigue. In yet further aspects of the disclosure, BTK inhibitors can be used to treat for indolent systemic mastocytosis, optionally including the reducing or alleviating of allergic symptoms, such as runny nose, nasal congestion and/or throat itching. In yet further aspects of the disclosure, BTK inhibitors can be used to treat for indolent systemic mastocytosis, optionally including the reducing or alleviating of respiratory symptoms such as wheezing, shortness of breath and/or heart palpitations. In yet further aspects of the disclosure, BTK inhibitors can be used to treat for indolent systemic mastocytosis, optionally including the reducing or alleviating of systemic symptoms such as muscle pain and/or concentration.

In one aspect, there is provided a BTK inhibitor for use in reducing or alleviating any one or more of the aforementioned symptoms in a human subject with ISM, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

In certain aspects, the present disclosure relates to a method of treating indolent systemic mastocytosis (ISM) comprising the step of administering to a human subject in need thereof a BTK inhibitor compound or a pharmaceutically acceptable salt thereof. In some embodiments, the BTK inhibitor is any of the compounds in Table 1 or a pharmaceutically acceptable salt thereof.

In an embodiment, the disclosure relates to a method of treating ISM in a human subject that comprises the step of administering to said human subject a therapeutically effective amount of a BTK inhibitor or a pharmaceutically acceptable salt thereof, wherein the BTK inhibitor is a compound selected from Table 1. In an embodiment, the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

In an embodiment, the BTK inhibitor, such as 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, is administered in an amount sufficient to reduce degranulation and release of histamine and/or cytokines from mast cells and/or basophil cells in the human subject. In an embodiment, the BTK inhibitor is administered in an amount sufficient to inhibit histamine release from mast cells or basophil cells in the human subject. In an embodiment, the BTK inhibitor is administered in an amount sufficient to inhibit tryptase release in the human subject. In an embodiment, the BTK inhibitor is administered in an amount sufficient to inhibit cytokine release/production in the human subject. In an embodiment, administering the BTK inhibitor reduces mast cell and/or basophil cell activation and thus reduced mast cell degranulation and cytokine-driven inflammation. In an embodiment, the BTK inhibitor is administered in an amount sufficient to reduce cytokine expression by mast cells and basophils. In an embodiment, the BTK inhibitor is administered in an amount sufficient reduce one or more secondary (i.e. distal) inflammatory process. As used herein, a secondary inflammatory process occurs at a site different from an initial inflammatory process. Such reductions in secondary inflammatory processes can be measured by any means described herein and known in the art.

In an embodiment, the BTK inhibitor, such as 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, is administered in an amount sufficient to inhibit FcεRI-mediated calcium mobilization in the human subject, resulting in down-stream inhibition of degranulation in mast cells and basophils. In mast cells, elevation in cytosolic calcium activates a cascade of downstream events that trigger degranulation, which is responsible for the release of inflammatory mediators associated with antigen binding to IgE bound to FcεRI. Without wishing to be bound by theory, it is believed that BTK inhibitors block mast cell degranulation through the inhibition of calcium signaling, halting acute and late phase cytokine-driven inflammation. In an embodiment, the BTK inhibitor is administered in an amount sufficient to reduce IgE-mediated FcεRI activity. In an embodiment, the BTK inhibitor is administered in an amount sufficient to reduce IgE-mediated FcεRI expression. In an embodiment, the BTK inhibitor is administered in an amount sufficient to reduce non-IgE-mediated FcεRI activity. In an embodiment, the IgE-mediated FcεRI activity is regulated by BTK activity.

In an embodiment, monomeric IgE (i.e. not bound to antigen) is already bound to FcεRI on a mast cell, priming the mast cell for activation upon binding of antigen. Thus, mast cells expressing FcεRI which is bound to IgE may be present in the skin or gastrointestinal tract, and produce the inflammatory response associated with ISM. In an embodiment, the BTK inhibitor, such as 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, is administered in an amount sufficient to inhibit this activation of mast cells in the skin and/or gastrointestinal tract. Further, treatment with a BTK inhibitor over time may reduce the amount of these primed mast cells at the inflammatory site (e.g. the skin and/or gastrointestinal tract). In an embodiment, the binding of monomeric IgE results in activation of the mast cells without the binding of antigen to IgE. See Cruse (2005) Eur. Respir. J. 25, 858-863. In an embodiment, the mast cells contain a mutation in KIT (e.g. D816V) which constitutively activates the mast cell resulting a level of degranulation which occurs in the absence of antigen binging to IgE. In an embodiment, the inhibition of BTK mediates sequestration of mast cells in the bone marrow. This sequestration of mast cells in the bone marrow results in decreased numbers of mast cells at potential peripheral tissue inflammatory sites (e.g. the skin and/or gastrointestinal tract). Hence, in an embodiment, this reduction of mast cells reduces the inflammatory response at the site of antigen exposure because there are fewer mast cells and/or basophils in the peripheral tissue to recruit and sustain an inflammatory response.

In an embodiment, the inhibition of BTK-mediated calcium release mediates a reduced inflammatory response. In an embodiment, the inhibition of BTK-mediated cytokine production mediates a reduced inflammatory response. In an embodiment, the inhibition of BTK reduces dysregulation of the cytokine production and subsequent inflammatory response. In an embodiment, inhibition of BTK blocks mast cell degranulation and inflammation through inhibition of FcεRI-induced calcium release and the subsequent inflammatory response.

In an embodiment, the BTK inhibitor, such as 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, is administered in an amount sufficient to reduce degranulation of mast cells and/or basophil cells in the human subject. Such inhibition of degranulation blocks the release of histamine, tryptases, prostaglandins, leukotrienes, kinins, serotonin, heparin and serine proteases.

In an embodiment, the BTK inhibitor, such as 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, is administered in an amount sufficient to reduce release of leukotrienes. In an embodiment, the BTK inhibitor is administered in an amount sufficient to reduce release of histamine, prostaglandins, leukotrienes, tryptase, kinins, serotonin, heparin and serine proteases from mast cells which occurs during degranulation.

In an embodiment, the human subject is suffering from indolent systemic mastocytosis where the mast cells of the human subject have a KIT D816V mutation. In the vast majority of cases with systemic mastocytosis, the clonal nature of the disease can be established through demonstration of a somatic A to T missense mutation at position 2447 of the coding sequence in the KIT gene (Orfao et al. (2007) Br. J. Haematol. 138:12-30). Without wishing to be bound by theory, the resulting substitution of aspartate (D) to valine (V) at amino acid position 816 in the kinase domain can lead to autoactivation of the KIT receptor tyrosine kinase and cause systemic mastocytosis.

In an embodiment, the KIT D816V mutation results in constitutive activation of KIT. In an embodiment, the constitutive activation of KIT results in the aggregation of mast cells in bone marrow and/or peripheral tissue (e.g., skin or gut) of the human subject which degranulate upon exposure to a lower antigenic stimulus than healthy mast cells. In an embodiment, the constitutive activation of KIT results in the aggregation of mast cells in bone marrow of the human subject which degranulate upon exposure to a lower level of antigenic stimulus than healthy mast cells. In an embodiment, the constitutive activation of KIT results in the aggregation of mast cells in peripheral tissue (e.g. skin or gut) of the human subject which degranulate upon exposure to a lower level of antigenic stimulus than healthy mast cells.

In an embodiment, the human subject is suffering from indolent systemic mastocytosis which does not have a KIT D816V mutation.

In an embodiment, the BTK inhibitor is administered twice daily at a dose selected from the group consisting of 10 mg, 25 mg, 50 mg, 75 mg, 100 mg, 150 mg, 200 mg, 250 mg, and 300 mg. In an embodiment, the BTK inhibitor is administered once daily at a dose selected from the group consisting of 10 mg, 25 mg, 50 mg, 75 mg, 100 mg, 150 mg, 200 mg, 250 mg, and 300 mg. In an embodiment, the BTK inhibitor is administered twice daily at a dose selected from the group consisting of at least about 10 mg, at least about 25 mg, at least about 50 mg, at least about 75 mg, at least about 100 mg, at least about 150 mg, at least 200 mg, at least 250 mg, and at least 300 mg. In an embodiment, the BTK inhibitor is administered once daily at a dose selected from the group consisting of about 10 mg, about 25 mg, about 50 mg, about 75 mg, about 100 mg, about 150 mg, about 200 mg, about 250 mg, and about 300 mg. In an embodiment, the BTK inhibitor is administered to a human subject according to Section Dosages and Dosing Regimens.

In an embodiment, the disclosure relates to a method of treating indolent systemic mastocytosis (ISM) in a human subject that comprises the step of administering to said human subject a therapeutically effective amount of a BTK inhibitor or a pharmaceutically acceptable salt thereof, wherein the BTK inhibitor is a compound selected from Table 1. In one embodiment, the BTK inhibitor is Compound 128 in Table 1 (1-(4-(((6-amino-5-(4-phenoxyphenyl)pyrimidin-4-yl)amino)methyl)-4-fluoropiperidin-1-yl)prop-2-en-1-one).

TABLE 1

| | | BTK Inhibitors |
|---|---|---|
| No. | IUPAC Name | Structure |
| 1. | Acalabrutinib ((S)-4-(8-amino-3-(1-(but-2-ynoyl)pyrrolidin-2-yl)imidazo[1,5-a]pyrazin-1-yl)-N-(pyridin-2-yl)benzamide) | |
| 2. | Ibrutinib (1-[(3R)-3-[4-amino-3-(4-phenoxyphenyl)pyrazolo[3,4-d]pyrimidin-1-yl]piperidin-1-yl]prop-2-en-1-one) | |
| 3. | (7S)-2-(4-phenoxyphenyl)-7-(1-prop-2-enoylpiperidin-4-yl)-4,5,6,7-tetrahydropyrazolo[1,5-a]pyrimidine-3-carboxamide | |
| 4. | 2-(4-phenoxyphenyl)-7-(1-prop-2-enoylpiperidin-4-yl)-4,5,6,7-tetrahydropyrazolo[1,5-a]pyrimidine-3-carboxamide | |

TABLE 1-continued

BTK Inhibitors

| No. | IUPAC Name | Structure |
|---|---|---|
| 5. | (7R)-2-(4-phenoxyphenyl)-7-(1-prop-2-enoylpiperidin-4-yl)-4,5,6,7-tetrahydropyrazolo[1,5-a]pyrimidine-3-carboxamide | 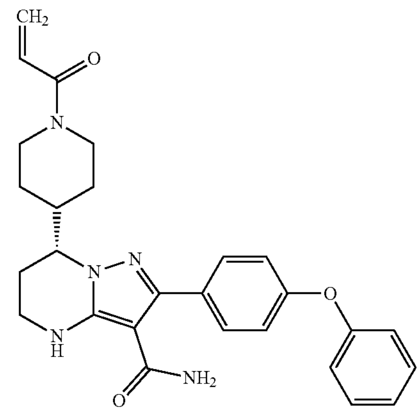 [SMILES: C=CC(=O)N1CCC([C@H]2CCNc3c(C(N)=O)c(-c4ccc(Oc5ccccc5)cc4)nn32)CC1] |
| 6. | 6-amino-9-[(3R)-1-but-2-ynoylpyrrolidin-3-yl]-7-(4-phenoxyphenyl)purin-8-one | 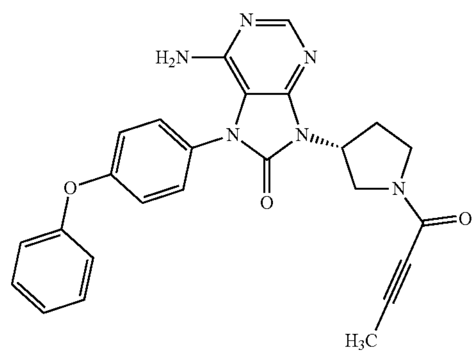 [SMILES: CC#CC(=O)N1CC[C@@H](n2c(=O)n(-c3ccc(Oc4ccccc4)cc3)c3c(N)ncnc32)C1] |
| 7. | N-[3-[[5-fluoro-2-[4-(2-methoxyethoxy)anilino]pyrimidin-4-yl]amino]phenyl]prop-2-enamide | 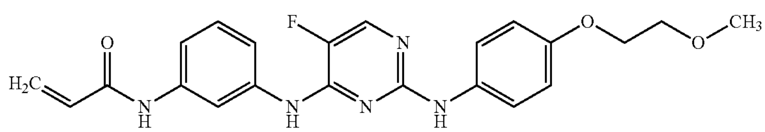 [SMILES: C=CC(=O)Nc1cccc(Nc2nc(Nc3ccc(OCCOC)cc3)ncc2F)c1] |
| 8. | Fenebrutinib (10-[3-(hydroxymethyl)-4-[1-methyl-5-[[5-[(2S)-2-methyl-4-(oxetan-3-yl)piperazin-1-yl]pyridin-2-yl]amino]-6-oxopyridin-3-yl]pyridin-2-yl]-4,4-dimethyl-1,10-diazatricyclo[6.4.0.0²,⁶]dodeca-2(6),7-dien-9-one) | 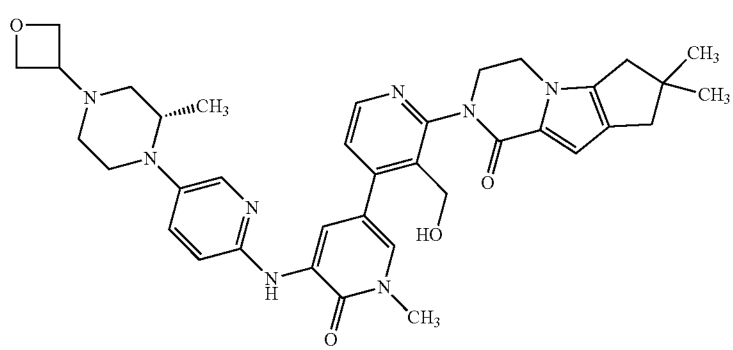 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1] |
| 9. | 1-[4-[[[6-amino-5-(4-phenoxyphenyl)pyrimidin-4-yl]amino]methyl]piperidin-1-yl]prop-2-en-1-one | 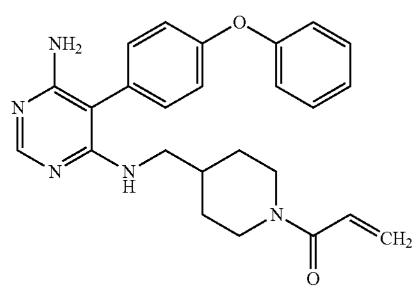 [SMILES: C=CC(=O)N1CCC(CNc2ncnc(N)c2-c2ccc(Oc3ccccc3)cc2)CC1] |

TABLE 1-continued

BTK Inhibitors

| No. | IUPAC Name | Structure |
|---|---|---|
| 10. | 1-[4-[[[6-amino-5-(4-phenoxyphenyl)pyrimidin-4-yl]amino]methyl]piperidin-1-yl]prop-2-en-1-one | 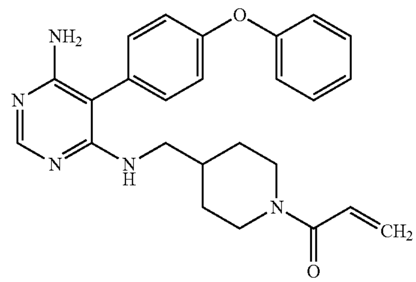 [SMILES: C=CC(=O)N1CCC(CNc2ncnc(N)c2-c2ccc(Oc3ccccc3)cc2)CC1] |
| 11. | (2-chloro-4-phenoxyphenyl)-[4-[[(3R,6S)-6-(hydroxymethyl)oxan-3-yl]amino]-7H-pyrrolo[2,3-d]pyrimidin-5-yl]methanone | 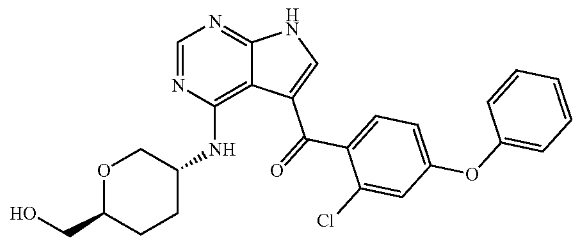 [SMILES: O=C(c1ccc(Oc2ccccc2)cc1Cl)c1c[nH]c2ncnc(N[C@@H]3CC[C@@H](CO)OC3)c12] |
| 12. | N-[3-[6-[4-[(2R)-1,4-dimethyl-3-oxopiperazin-2-yl]anilino]-4-methyl-5-oxopyrazin-2-yl]-2-methylphenyl]-4,5,6,7-tetrahydro-1-benzothiophene-2-carboxamide | 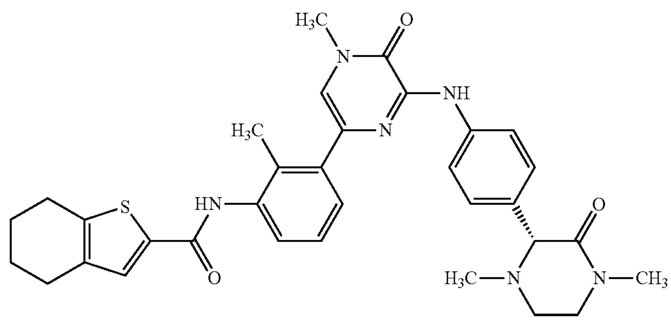 [SMILES: Cc1c(NC(=O)c2cc3c(s2)CCCC3)cccc1-c1cn(C)c(=O)c(Nc2ccc([C@@H]3C(=O)N(C)CCN3C)cc2)n1] |
| 13. | 2-[2-[2-[4-[4-amino-3-(4-phenoxyphenyl)pyrazolo[3,4-d]pyrimidin-1-yl]piperidin-1-yl]ethoxy]ethoxy]-N-[2-(2,6-dioxopiperidin-3-yl)-1,3-dioxoisoindol-5-yl]acetamide | 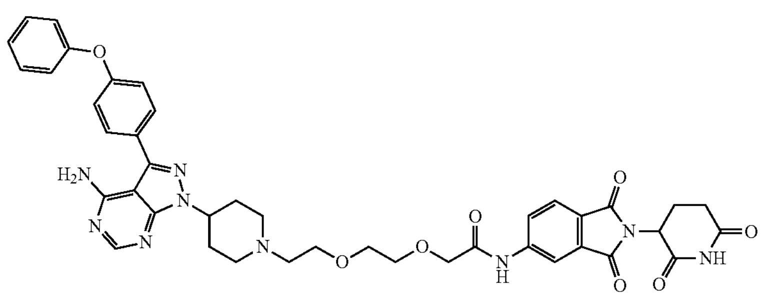 [SMILES: Nc1ncnc2c1c(-c1ccc(Oc3ccccc3)cc1)nn2C1CCN(CCOCCOCC(=O)Nc2ccc3c(c2)C(=O)N(C2CCC(=O)NC2=O)C3=O)CC1] |
| 14. | N-[3-[2-[4-(4-methylpiperazin-1-yl)anilino]furo[3,2-d]pyrimidin-4-yl]oxyphenyl]prop-2-enamide | 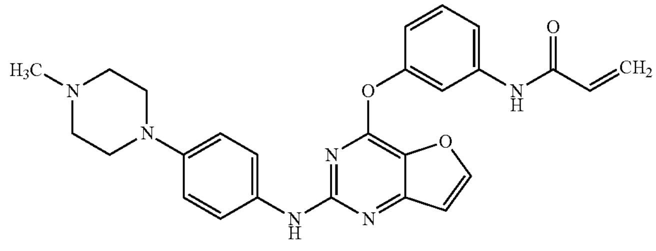 [SMILES: C=CC(=O)Nc1cccc(Oc2nc(Nc3ccc(N4CCN(C)CC4)cc3)nc3ccoc23)c1] |

TABLE 1-continued

BTK Inhibitors

| No. | IUPAC Name | Structure |
|-----|------------|-----------|
| 15. | 4-tert-butyl-N-[2-methyl-3-[1-methyl-5-[4-(morpholine-4-carbonyl)-3-(prop-2-enoylamino)anilino]-6-oxopyridin-3-yl]phenyl]benzamide | 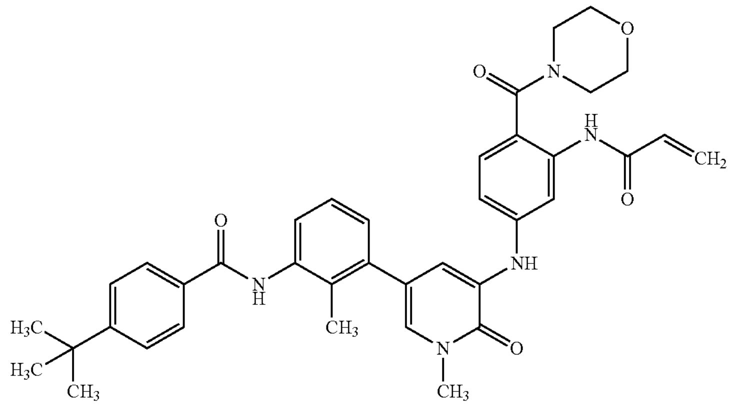 [SMILES: C=CC(=O)Nc1cc(Nc2cc(-c3cccc(NC(=O)c4ccc(C(C)(C)C)cc4)c3C)cn(C)c2=O)ccc1C(=O)N1CCOCC1] |
| 16. | (R,E)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile | 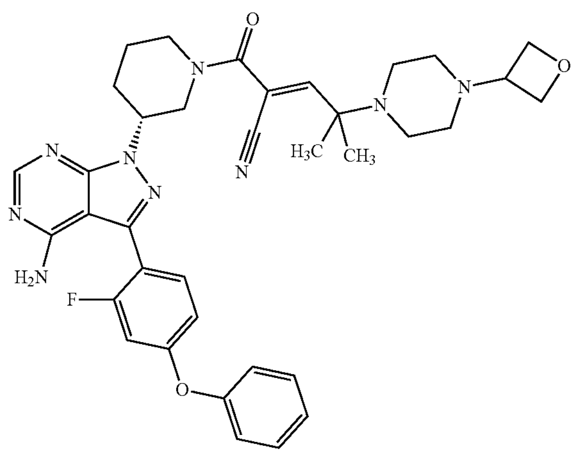 [SMILES: CC(C)(/C=C(\C#N)C(=O)N1CCC[C@@H](n2nc(-c3ccc(Oc4ccccc4)cc3F)c3c(N)ncnc32)C1)N1CCN(C2COC2)CC1] |
| 17. | Branebrutinib ((S)-4-(3-(but-2-ynamido)piperidin-1-yl)-5-fluoro-2,3-dimethyl-1H-indole-7-carboxamide) | 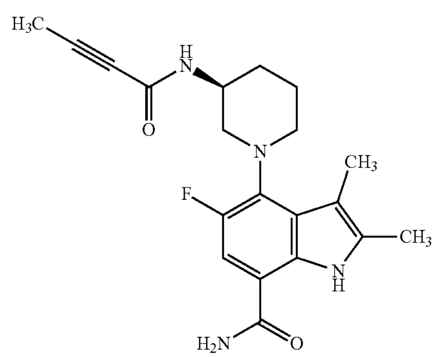 [SMILES: CC#CC(=O)N[C@H]1CCCN(c2c(F)cc(C(N)=O)c3[nH]c(C)c(C)c23)C1] |
| 18. | 4-(tert-Butyl)-N-(2-methyl-3-(4-methyl-6-((4-(morpholine-4-carbonyl)phenyl)amino)-5-oxo-4,5-dihydropyrazin-2-yl)phenyl)benzamide | 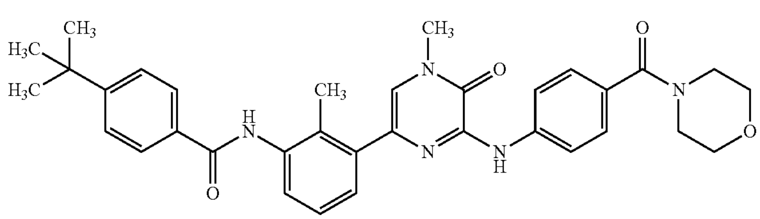 [SMILES: Cc1c(NC(=O)c2ccc(C(C)(C)C)cc2)cccc1-c1cn(C)c(=O)c(Nc2ccc(C(=O)N3CCOCC3)cc2)n1] |

TABLE 1-continued

BTK Inhibitors

| No. | IUPAC Name | Structure |
|---|---|---|
| 19. | N-(1-(7H-Pyrrolo[2,3-d]pyrimidin-4-yl)piperidin-3-yl)-2-((3-chlorophenyl)amino) acetamide | 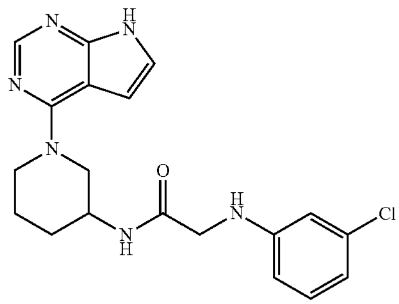 [SMILES: O=C(CNc1cccc(Cl)c1)NC1CCCN(c2ncnc3[nH]ccc23)C1] |
| 20. | 6-cyclopropyl-8-fluoro-2-[2-(hydroxymethyl)-3-[1-methyl-5-[[5-(4-methylpiperazin-1-yl)pyridin-2-yl]amino]-6-oxopyridin-3-yl]phenyl]isoquinolin-1-one | 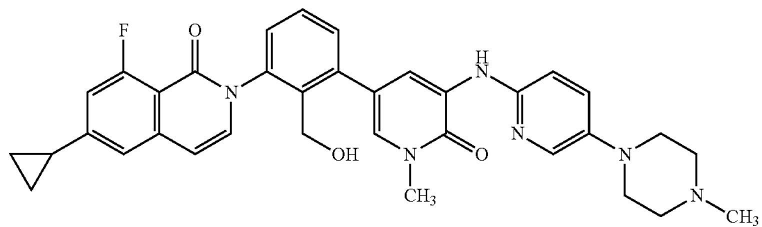 [SMILES: CN1CCN(c2ccc(Nc3cc(-c4cccc(-n5ccc6cc(C7CC7)cc(F)c6c5=O)c4CO)cn(C)c3=O)nc2)CC1] |
| 21. | N-[5-[9-[4-(methanesulfonamido)phenyl]-2-oxobenzo[h][1,6]naphthyridin-1-yl]-2-methylphenyl]prop-2-enamide | 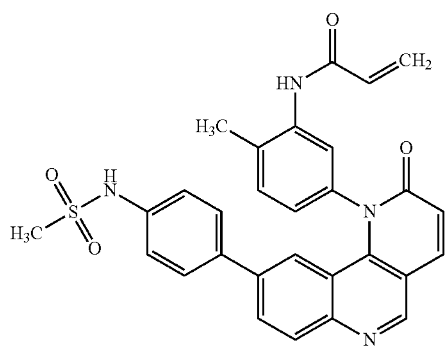 [SMILES: C=CC(=O)Nc1cc(-n2c(=O)ccc3cnc4ccc(-c5ccc(NS(C)(=O)=O)cc5)cc4c32)ccc1C] |
| 22. | 4-(4-((4-((3-acrylamidophenyl)amino)-5-fluoropyrimidin-2-yl)amino)phenoxy)-N-methylpicolinamide | 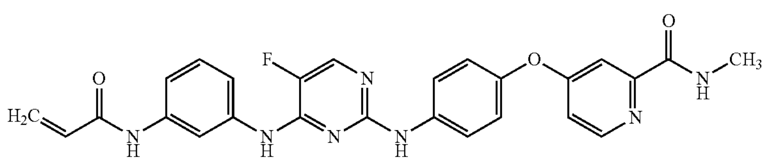 [SMILES: C=CC(=O)Nc1cccc(Nc2nc(Nc3ccc(Oc4ccnc(C(=O)NC)c4)cc3)ncc2F)c1] |
| 23. | (7S)-3-fluoro-4-[3-(8-fluoro-1-methyl-2,4-dioxoquinazolin-3-yl)-2-methylphenyl]-7-(2-hydroxypropan-2-yl)-6,7,8,9-tetrahydro-5H-carbazole-1-carboxamide | 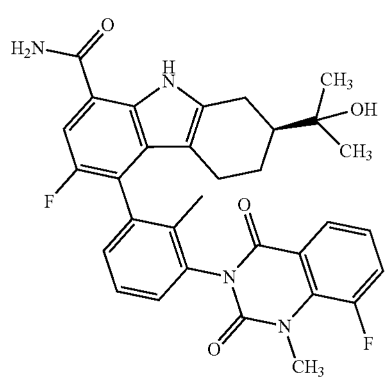 [SMILES: Cc1c(-c2c(F)cc(C(N)=O)c3[nH]c4c(c23)CC[C@H](C(C)(C)O)C4)cccc1-n1c(=O)c2cccc(F)c2n(C)c1=O] |

TABLE 1-continued

BTK Inhibitors

| No. | IUPAC Name | Structure |
|---|---|---|
| 24. | 1-[3-fluoro-4-[7-(5-methyl-1H-imidazol-2-yl)-1-oxo-2,3-dihydroisoindol-4-yl]phenyl]-3-[3-(trifluoromethyl)phenyl]urea | 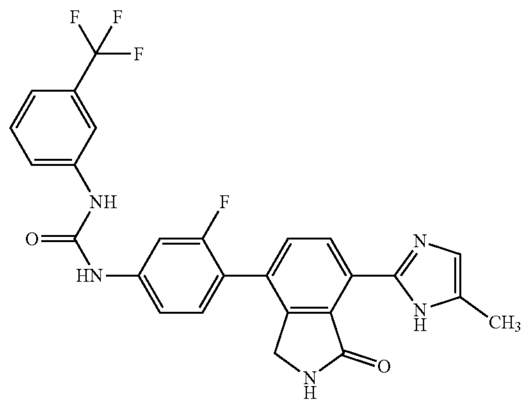 [SMILES: Cc1cnc(-c2ccc(-c3ccc(NC(=O)Nc4cccc(C(F)(F)F)c4)cc3F)c3c2C(=O)NC3)[nH]1] |
| 25. | 9-(1-methylpyrazol-4-yl)-1-(1-prop-2-enoyl-2,3-dihydroindol-6-yl)benzo[h][1,6]naphthyridin-2-one | 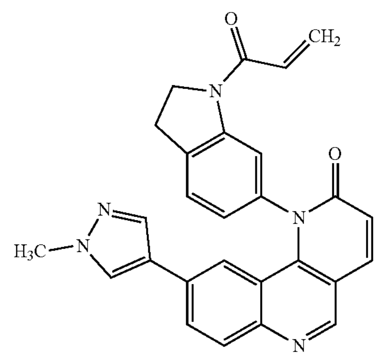 [SMILES: C=CC(=O)N1CCc2ccc(-n3c(=O)ccc4cnc5ccc(-c6cnn(C)c6)cc5c43)cc21] |
| 26. | 7-(2-hydroxypropan-2-yl)-4-[2-methyl-3-(4-oxoquinazolin-3-yl)phenyl]-9H-carbazole-1-carboxamide | 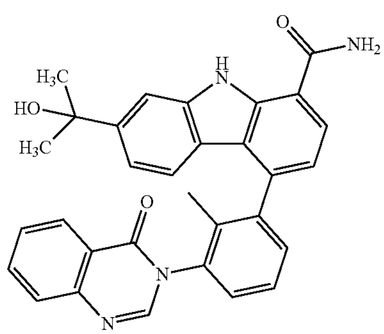 [SMILES: Cc1c(-c2ccc(C(N)=O)c3[nH]c4cc(C(C)(C)O)ccc4c23)cccc1-n1cnc2ccccc2c1=O] |
| 27. | 10-[2-(Hydroxymethyl)-3-[1-methyl-6-oxo-5-(pyrimidin-4-ylamino)pyridin-3-yl]phenyl]-4,4-dimethyl-7-thia-10-azatricyclo[6.4.0.0²,⁶]dodeca-1(8),2(6)-dien-9-one | 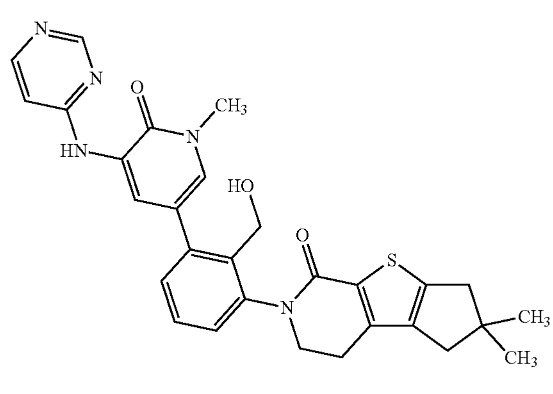 [SMILES: Cn1cc(-c2cccc(N3CCc4c(sc5c4CC(C)(C)C5)C3=O)c2CO)cc(Nc2ccncn2)c1=O] |

TABLE 1-continued

BTK Inhibitors

| No. | IUPAC Name | Structure |
|-----|------------|-----------|
| 28. | (S)-5-amino-1-(1-cyanopiperidin-3-yl)-3-(4-(2,4-difluorophenoxy)phenyl)-1H-pyrazole-4-carboxamide | 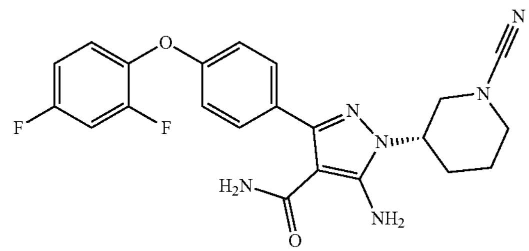 [SMILES: N#CN1CCC[C@H](n2nc(-c3ccc(Oc4ccc(F)cc4F)cc3)c(C(N)=O)c2N)C1] |
| 29. | (S)-4-(3-(1-Acryloylpyrrolidin-2-yl)-8-aminoimidazo[1,5-a]pyrazin-1-yl)-N-(pyridin-2-yl)benzamide | 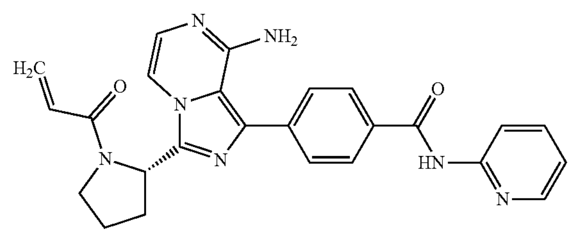 [SMILES: C=CC(=O)N1CCC[C@H]1c1nc(-c2ccc(C(=O)Nc3ccccn3)cc2)c2c(N)nccn12] |
| 30. | (S,E)-4-(8-Amino-3-(1-(4-(dimethylamino)but-2-enoyl)pyrrolidin-2-yl)imidazo[1,5-a]pyrazin-1-yl)-N(pyridin-2-yl)benzamide | 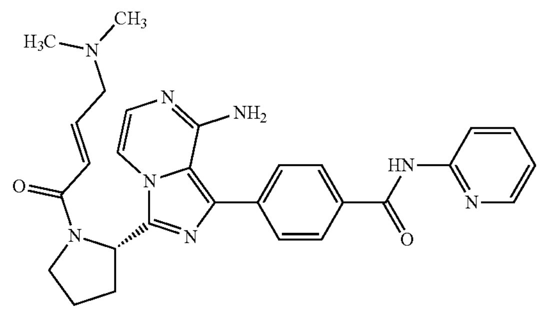 [SMILES: CN(C)C/C=C/C(=O)N1CCC[C@H]1c1nc(-c2ccc(C(=O)Nc3ccccn3)cc2)c2c(N)nccn12] |
| 31. | (S)-4-(8-Amino-3-(1-but-2-ynoylpyrrolidin-2-yl)imidazo[1,5-a]pyrazin-1-yl)-N-(4-methylpyridin-2-yl)benzamide | 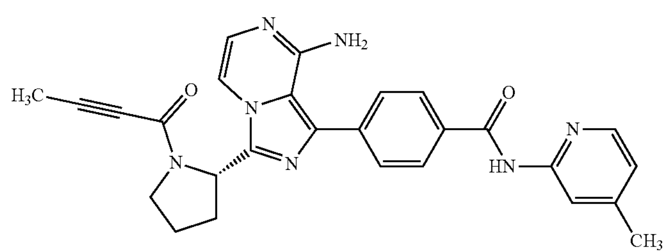 [SMILES: CC#CC(=O)N1CCC[C@H]1c1nc(-c2ccc(C(=O)Nc3cc(C)ccn3)cc2)c2c(N)nccn12] |
| 32. | (S,E)-4-(8-Amino-3-(1-(4-methoxybut-2-enoyl)pyrrolidin-2-yl)imidazo[1,5-a]pyrazin-1-yl)-N-(4-propylpyridin-2-yl)benzamide | 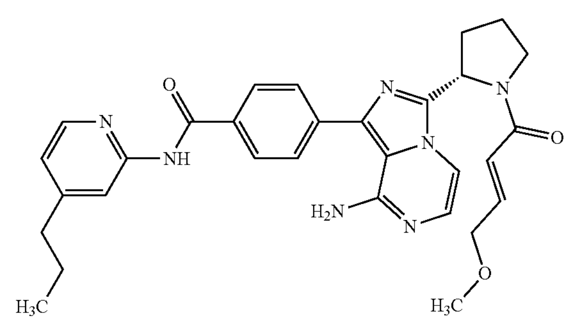 [SMILES: CCCc1ccnc(NC(=O)c2ccc(-c3nc([C@@H]4CCCN4C(=O)/C=C/COC)n4ccnc(N)c34)cc2)c1] |

TABLE 1-continued

BTK Inhibitors

| No. | IUPAC Name | Structure |
| --- | --- | --- |
| 33. | (S)-4-(8-Amino-3-(1-but-2-ynoylpyrrolidin-2-yl)imidazo[1,5-a]pyrazin-1-yl)-N-(4-(trifluoromethyl)pyridin-2-yl)benzamide | 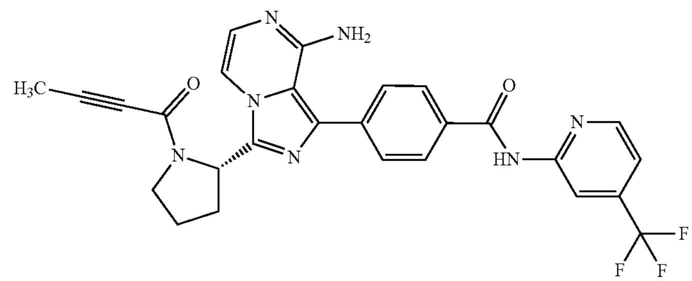 [SMILES: CC#CC(=O)N1CCC[C@H]1c1nc(-c2ccc(C(=O)Nc3cc(C(F)(F)F)ccn3)cc2)c2c(N)nccn12] |
| 34. | (S)-4-(8-Amino-3-(1-but-2-ynoylpyrrolidin-2-yl)imidazo[1,5-a]pyrazin-1-yl)-N-(4,5,6,7-tetrahydrobenzo[d]thiazol-2-yl)benzamide | 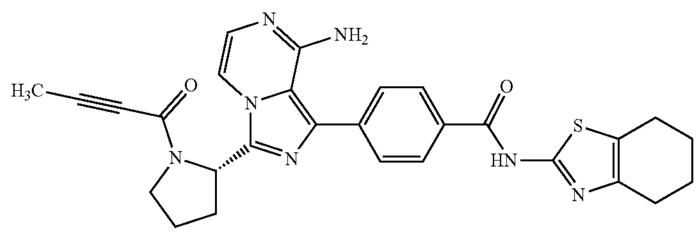 [SMILES: CC#CC(=O)N1CCC[C@H]1c1nc(-c2ccc(C(=O)Nc3nc4c(s3)CCCC4)cc2)c2c(N)nccn12] |
| 35. | (S)-4-(3-(1-acryloylpyrrolidin-2-yl)-8-aminoimidazo[1,5-a]pyrazin-1-yl)-2-fluoro-N-(pyridin-2-yl)benzamide | 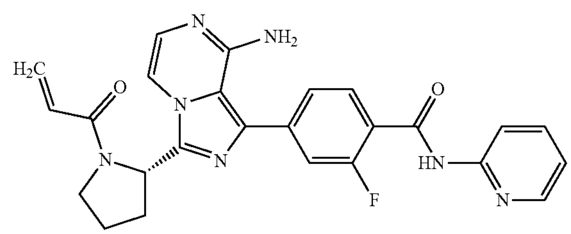 |
| 36. | (S)-4-(3-(1-Acryloylpyrrolidin-2-yl)-8-aminoimidazo[1,5-a]pyrazin-1-yl)-2-methoxy-N-(pyridin-2-yl)benzamide | 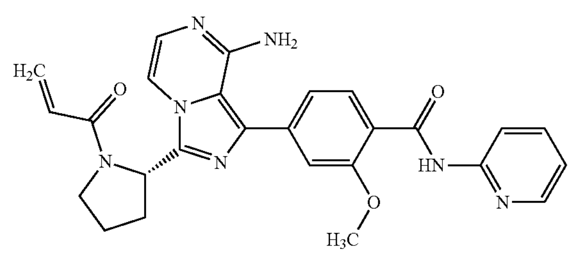 [SMILES: C=CC(=O)N1CCC[C@H]1c1nc(-c2ccc(C(=O)Nc3ccccn3)c(OC)c2)c2c(N)nccn12] |
| 37. | (S,E)-4-(8-Amino-3-(1-(4-(dimethylamino)but-2-enoyl)pyrrolidin-2-yl)imidazo[1,5-a]pyrazin-1-yl)-N-(thiazol-2-yl)benzamide | 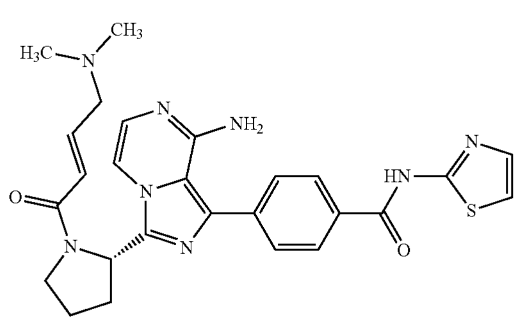 [SMILES: CN(C)C/C=C/C(=O)N1CCC[C@H]1c1nc(-c2ccc(C(=O)Nc3nccs3)cc2)c2c(N)nccn12] |

TABLE 1-continued

BTK Inhibitors

| No. | IUPAC Name | Structure |
|---|---|---|
| 38. | (S)-4-(3-(1-Acryloylpiperidin-2-yl)-8-aminoimidazo[1,5-a]pyrazin-1-yl)-N-(4-fluoropyridin-2-yl)benzamide | 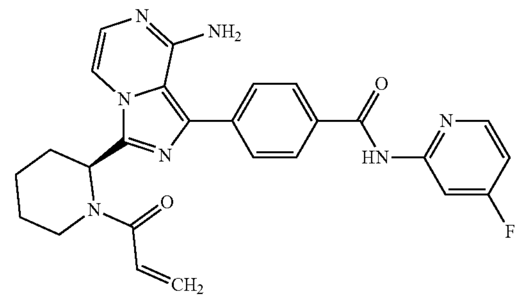 [SMILES: C=CC(=O)N1CCCC[C@H]1c1nc(-c2ccc(C(=O)Nc3cc(F)ccn3)cc2)c2c(N)nccn12] |
| 39. | (S)-4-(3-(1-Acryloylpiperidin-2-yl)-8-aminoimidazo[1,5-a]pyrazin-1-yl)-N-(4-cyanopyridin-2-yl)benzamide | 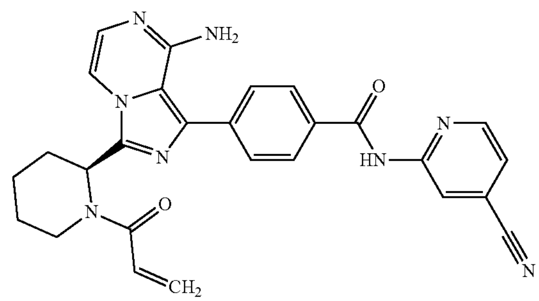 [SMILES: C=CC(=O)N1CCCC[C@H]1c1nc(-c2ccc(C(=O)Nc3cc(C#N)ccn3)cc2)c2c(N)nccn12] |
| 40. | (S)-4-(8-Amino-3-(1-(vinylsulfonyl)piperidin-2-yl)imidazo[1,5-a]pyrazin-1-yl)-N-(4-(trifluoromethyl)pyridin-2-yl)benzamide | 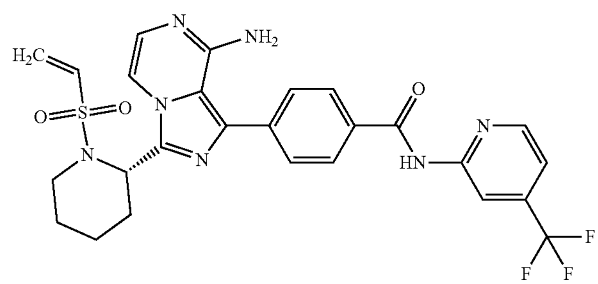 [SMILES: C=CS(=O)(=O)N1CCCC[C@H]1c1nc(-c2ccc(C(=O)Nc3cc(C(F)(F)F)ccn3)cc2)c2c(N)nccn12] |
| 41. | (S)-4-(3-(1-Acryloylpiperidin-2-yl)-8-aminoimidazo[1,5-a]pyrazin-1-yl)-N-(pyrimidin-2-yl)benzamide | 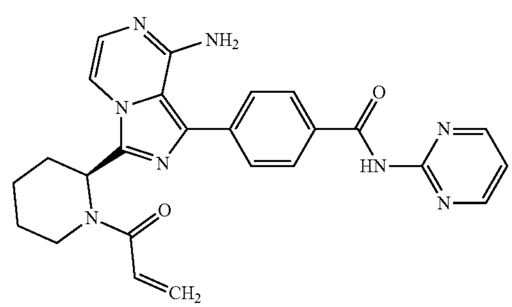 [SMILES: C=CC(=O)N1CCCC[C@H]1c1nc(-c2ccc(C(=O)Nc3ncccn3)cc2)c2c(N)nccn12] |
| 42. | (S)-4-(3-(1-Acryloylpiperidin-2-yl)-8-aminoimidazo[1,5-a]pyrazin-1-yl)-N-(4-methylpyrimidin-2-yl)benzamide | 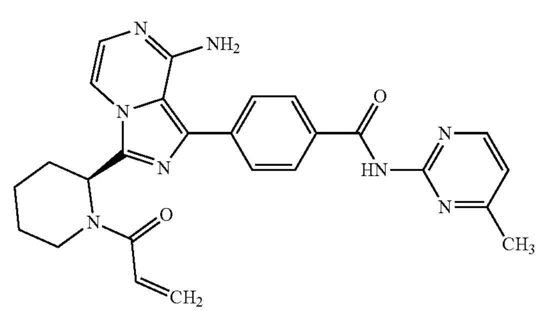 [SMILES: C=CC(=O)N1CCCC[C@H]1c1nc(-c2ccc(C(=O)Nc3nccc(C)n3)cc2)c2c(N)nccn12] |

TABLE 1-continued

BTK Inhibitors

| No. | IUPAC Name | Structure |
| --- | --- | --- |
| 43. | (S)-4-(8-Amino-3-(1-but-2-ynoylpiperidin-2-yl)imidazo[1,5-a]pyrazin-1-yl)-N-(pyrimidin-4-yl)benzamide | 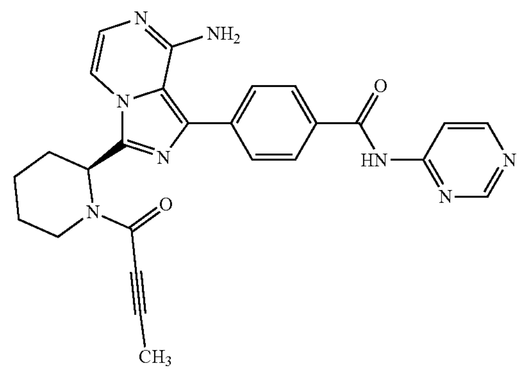 [SMILES: CC#CC(=O)N1CCCC[C@H]1c1nc(-c2ccc(C(=O)Nc3ccncn3)cc2)c2c(N)nccn12] |
| 44. | (S)-4-(8-Amino-3-(1-but-2-ynoylpiperidin-2-yl)imidazo[1,5-a]pyrazin-1-yl)-N-(pyridazin-3-yl)benzamide | 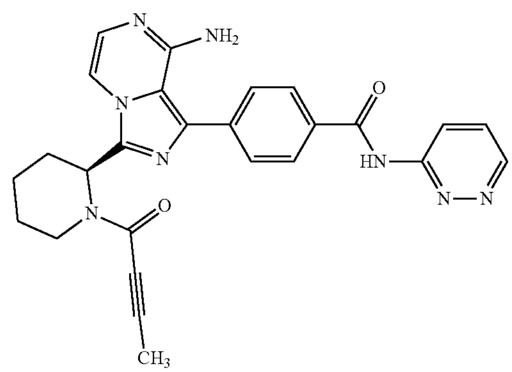 [SMILES: CC#CC(=O)N1CCCC[C@H]1c1nc(-c2ccc(C(=O)Nc3cccnn3)cc2)c2c(N)nccn12] |
| 45. | (S,E)-4-(8-Amino-3-(1-(4-methoxybut-2-enoyl)piperidin-2-yl)imidazo[1,5-a]pyrazin-1-yl)-N-(5-ethylthiazol-2-yl)benzamide | 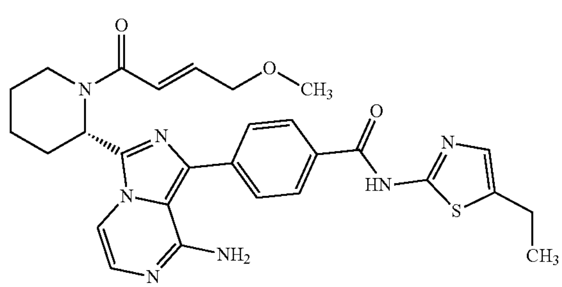 [SMILES: CCc1cnc(NC(=O)c2ccc(-c3nc([C@@H]4CCCCN4C(=O)/C=C/COC)n4ccnc(N)c34)cc2)s1] |
| 46. | (S)-4-(3-(1-Acryloylpiperidin-2-yl)-8-aminoimidazo[1,5-a]pyrazin-1-yl)-2-fluoro-N-(4-propylpyridin-2-yl)benzamide | 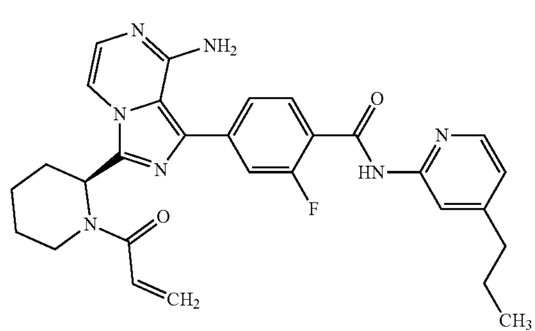 [SMILES: C=CC(=O)N1CCCC[C@H]1c1nc(-c2ccc(C(=O)Nc3cc(CCC)ccn3)c(F)c2)c2c(N)nccn12] |

TABLE 1-continued

BTK Inhibitors

| No. | IUPAC Name | Structure |
|---|---|---|
| 47. | (S,E)-4-(8-Amino-3-(1-(4-(dimethylamino)but-2-enoyl)piperidin-2-yl)imidazo[1,5-a]pyrazin-1-yl)-2-methoxy-N-(4-propylpyridin-2-yl)benzamide | 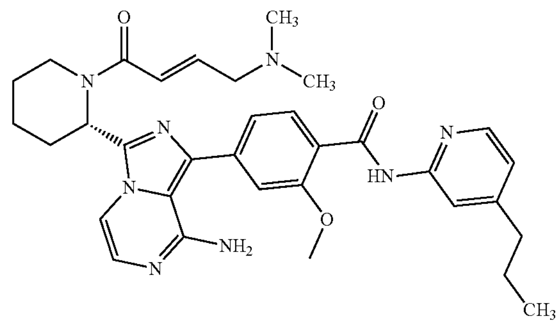 [SMILES: CCCc1ccnc(NC(=O)c2ccc(-c3nc([C@@H]4CCCCN4C(=O)/C=C/CN(C)C)n4ccnc(N)c34)cc2OC)c1] |
| 48. | 4-(8-Amino-3-((S)-1-but-2-ynoylpiperidin-2-yl)imidazo[1,5-a]pyrazin-1-yl)-3-methyl-N-(pyridin-2-yl)benzamide | 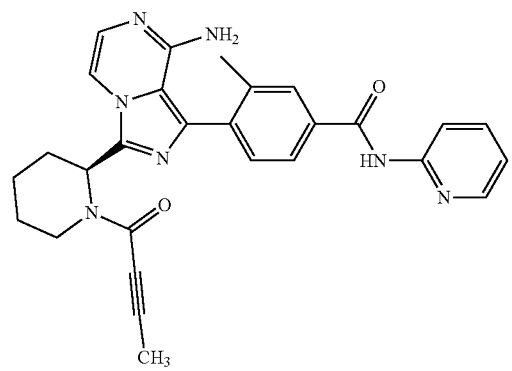 [SMILES: CC#CC(=O)N1CCCC[C@H]1c1nc(-c2ccc(C(=O)Nc3ccccn3)cc2C)c2c(N)nccn12] |
| 49. | 4-(3-(Acrylamidomethyl)-8-aminoimidazo[1,5-a]pyrazin-1-yl)-N-(pyridin-2-yl)benzamide | 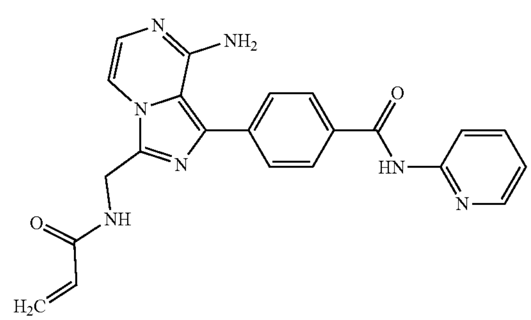 [SMILES: C=CC(=O)NCc1nc(-c2ccc(C(=O)Nc3ccccn3)cc2)c2c(N)nccn12] |
| 50. | (S)-4-(8-Amino-3-(1-but-2-ynamidoethyl)imidazo[1,5-a]pyrazin-1-yl)-N-(pyridin-2-yl)benzamide | 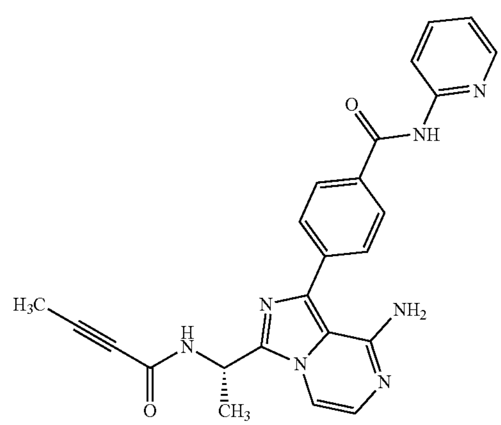 [SMILES: CC#CC(=O)N[C@@H](C)c1nc(-c2ccc(C(=O)Nc3ccccn3)cc2)c2c(N)nccn12] |

TABLE 1-continued

BTK Inhibitors

| No. | IUPAC Name | Structure |
|---|---|---|
| 51. | (S)-S-(2-(2-(8-amino-1-(4-(pyridin-2-ylcarbamoyl)phenyl)imidazo[1,5-a]pyrazin-3-yl)pyrrolidin-1-yl)-2-oxoethyl) ethanethioate | 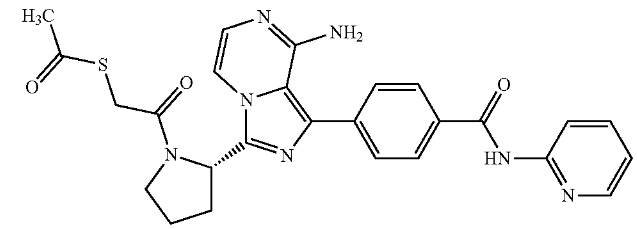 [SMILES: CC(=O)SCC(=O)N1CCC[C@H]1c1nc(-c2ccc(C(=O)Nc3ccccn3)cc2)c2c(N)nccn12] |
| 52. | (S)-4-(8-Amino-3-(1-(4-hydroxy-4-methylpent-2-ynoyl)pyrrolidin-2-yl)imidazo[1,5-a]pyrazin-1-yl)-N-(pyridin-2-yl)benzamide | 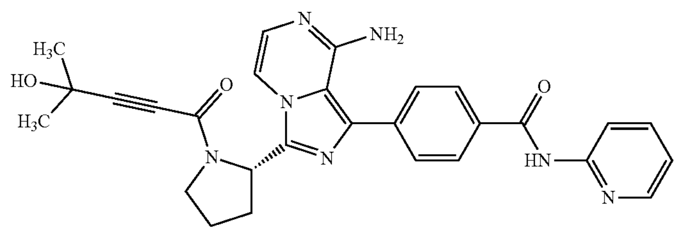 [SMILES: CC(C)(O)C#CC(=O)N1CCC[C@H]1c1nc(-c2ccc(C(=O)Nc3ccccn3)cc2)c2c(N)nccn12] |
| 53. | (S)-4-(8-Amino-3-(1-(6-chloropyrimidine-4-carbonyl)pyrrolidin-2-yl)imidazo[1,5-a]pyrazin-1-yl)-N-(pyridin-2-yl)benzamide | 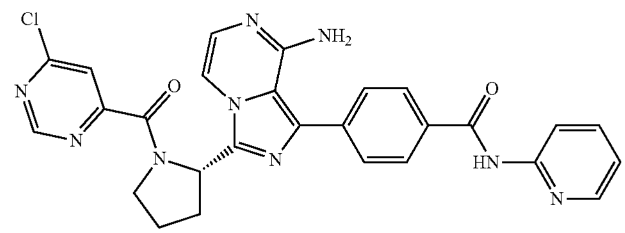 [SMILES: Nc1nccn2c([C@@H]3CCCN3C(=O)c3cc(Cl)ncn3)nc(-c3ccc(C(=O)Nc4ccccn4)cc3)c12] |
| 54. | (S)-4-(8-Amino-3-(1-pent-2-ynoylpyrrolidin-2-yl)imidazo[1,5-a]pyrazin-1-yl)-N-(pyridin-2-yl)benzamide | 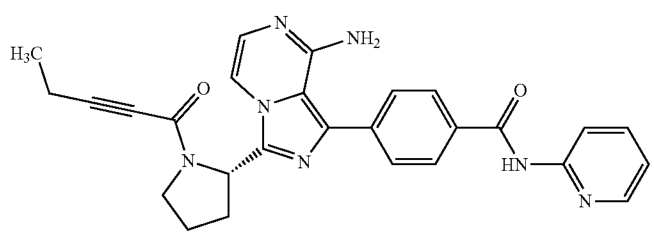 [SMILES: CCC#CC(=O)N1CCC[C@H]1c1nc(-c2ccc(C(=O)Nc3ccccn3)cc2)c2c(N)nccn12] |
| 55. | (S)-4-(8-Amino-3-(1-(3-cyclopropylpropioloyl)pyrrolidin-2-yl)imidazo[1,5-a]pyrazin-1-yl)-N-(pyridin-2-yl)benzamide | 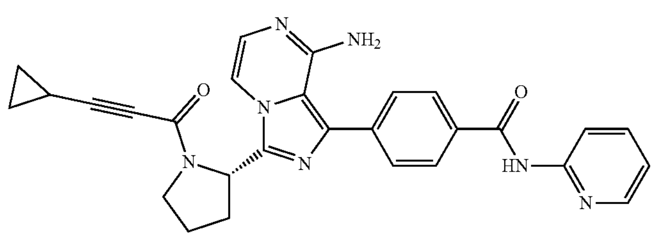 [SMILES: Nc1nccn2c([C@@H]3CCCN3C(=O)C#CC3CC3)nc(-c3ccc(C(=O)Nc4ccccn4)cc3)c12] |
| 56. | (S)-4-(8-Amino-3-(1-hex-2-ynoylpyrrolidin-2-yl)imidazo[1,5-a]pyrazin-1-yl)-N-(pyridin-2-yl)benzamide | 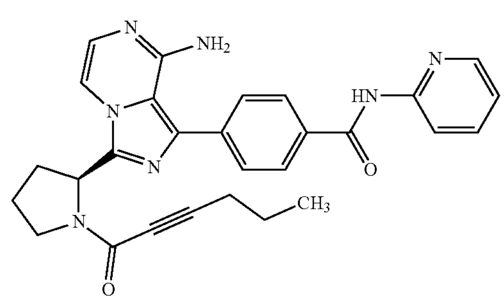 [SMILES: CCCC#CC(=O)N1CCC[C@H]1c1nc(-c2ccc(C(=O)Nc3ccccn3)cc2)c2c(N)nccn12] |

TABLE 1-continued

BTK Inhibitors

| No. | IUPAC Name | Structure |
|-----|------------|-----------|
| 57. | 4-(3-(1-Acryloylazepan-2-yl)-8-aminoimidazo[1,5-a]pyrazin-1-yl)-N-(pyridin-2-yl)benzamide | 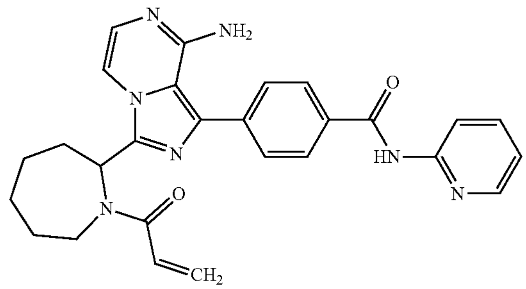 [SMILES: C=CC(=O)N1CCCCCC1c1nc(-c2ccc(C(=O)Nc3ccccn3)cc2)c2c(N)nccn12] |
| 58. | (R)-4-(8-Amino-3-(4-but-2-ynoylmorpholin-3-yl)imidazo[1,5-a]pyrazin-1-yl)-N-(pyridin-2-yl)benzamide | 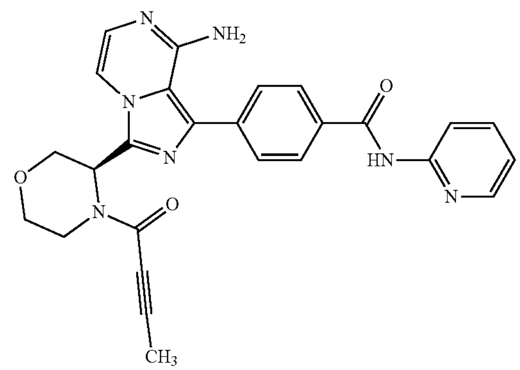 [SMILES: CC#CC(=O)N1CCOC[C@H]1c1nc(-c2ccc(C(=O)Nc3ccccn3)cc2)c2c(N)nccn12] |
| 59. | (S)-4-(8-amino-3-(1-(N-methylbut-2-ynamido)ethyl)imidazo[1,5-a]pyrazin-1-yl)-N-(4-(trifluoromethyl)pyridin-2-yl)benzamide | 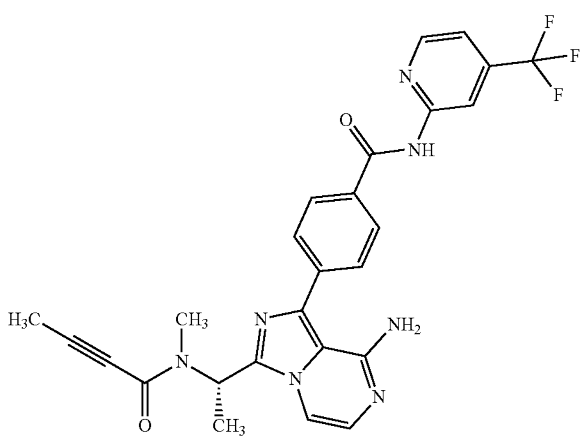 [SMILES: CC#CC(=O)N(C)[C@@H](C)c1nc(-c2ccc(C(=O)Nc3cc(C(F)(F)F)ccn3)cc2)c2c(N)nccn12] |
| 60. | (S)-4-(3-(1-acryloylpyrrolidin-2-yl)-8-aminoimidazo[1,5-a]pyrazin-1-yl)-N-(4-fluoropyridin-2-yl)benzamide | 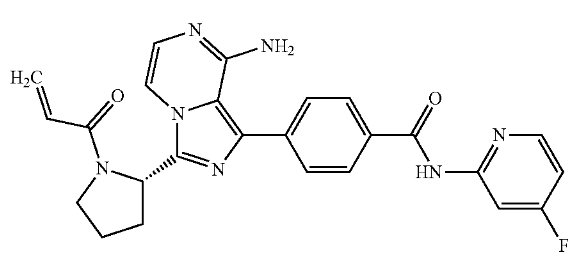 [SMILES: C=CC(=O)N1CCC[C@H]1c1nc(-c2ccc(C(=O)Nc3cc(F)ccn3)cc2)c2c(N)nccn12] |

TABLE 1-continued

BTK Inhibitors

| No. | IUPAC Name | Structure |
|---|---|---|
| 61. | (S)-4-(3-(1-acryloylpyrrolidin-2-yl)-8-aminoimidazo[1,5-a]pyrazin-1-yl)-N-(4-(pyrrolidin-1-yl)pyridin-2-yl)benzamide | 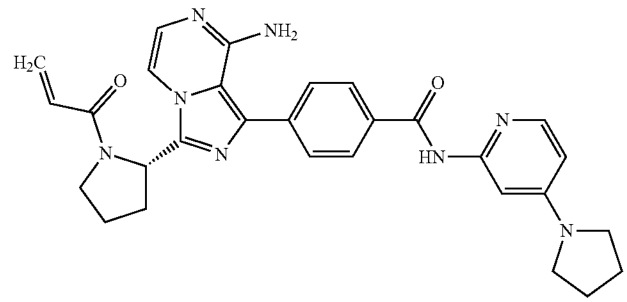 [SMILES: C=CC(=O)N1CCC[C@H]1c1nc(-c2ccc(C(=O)Nc3cc(N4CCCC4)ccn3)cc2)c2c(N)nccn12] |
| 62. | (S)-4-(8-amino-3-(1-but-2-ynoylpiperidin-2-yl)imidazo[1,5-a]pyrazin-1-yl)-N-(4-fluoropyridin-2-yl)benzamide | 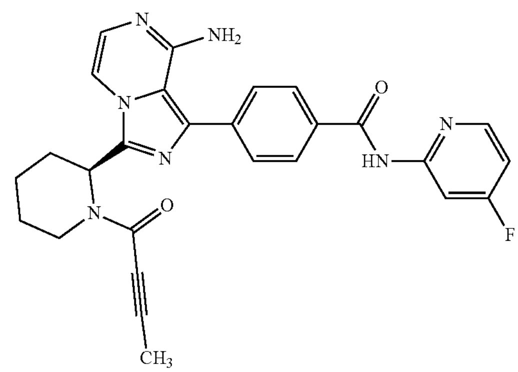 [SMILES: CC#CC(=O)N1CCCC[C@H]1c1nc(-c2ccc(C(=O)Nc3cc(F)ccn3)cc2)c2c(N)nccn12] |
| 63. | (S)-4-(8-amino-3-(1-but-2-ynoylpiperidin-2-yl)imidazo[1,5-a]pyrazin-1-yl)-N-(pyridine-2-yl)benzamide | 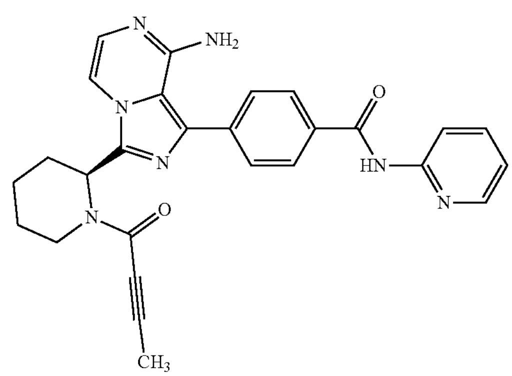 |
| 64. | (S)-4-(3-(1-acryloylpiperidin-2-yl)-8-aminoimidazo[1,5-a]pyrazin-1-yl)-N-(pyridine-2-yl)benzamide | 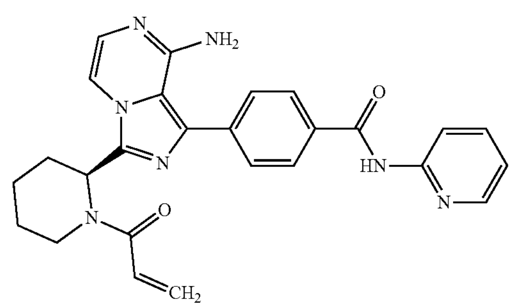 |

TABLE 1-continued

BTK Inhibitors

| No. | IUPAC Name | Structure |
|---|---|---|
| 65. | (S)-4-(8-amino-3-(1-but-2-ynoylpyrrolidin-2-yl)imidazo[1,5-a]pyrazin-1-yl)-N-(4-propylpyridin-2-yl)benzamide | 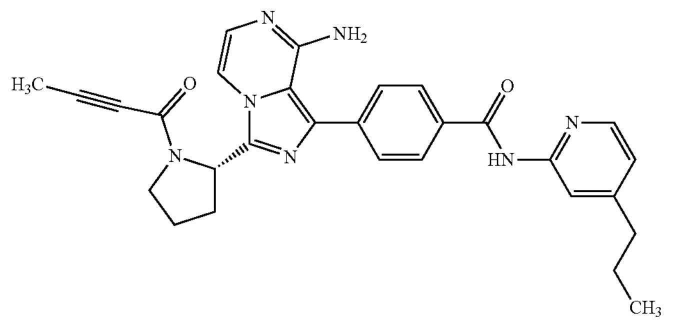 [SMILES: CC#CC(=O)N1CCC[C@H]1c1nc(-c2ccc(C(=O)Nc3cc(CCC)ccn3)cc2)c2c(N)nccn12] |
| 66. | (S,E)-4-(8-amino-3-(1-(4-methoxy-N-methylbut-2-enamido)ethyl)imidazo[1,5-a]pyrazin-1-yl)-N-(4-propylpyridin-2-yl)benzamide | 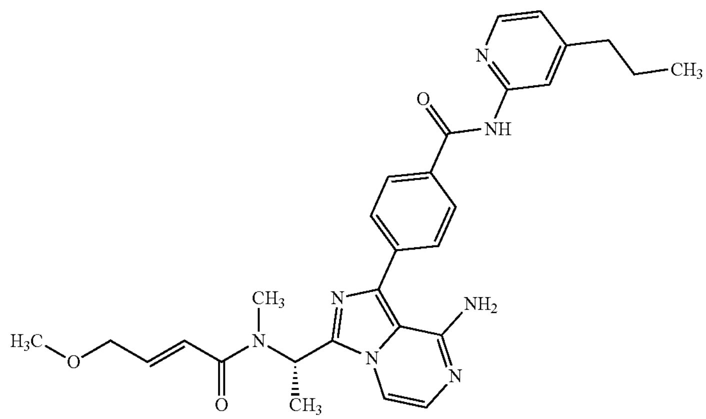 [SMILES: CCCc1ccnc(NC(=O)c2ccc(-c3nc([C@H](C)N(C)C(=O)/C=C/COC)n4ccnc(N)c34)cc2)c1] |
| 67. | (S)-4-(8-amino-3-(1-(vinylsulfonyl)piperidin-2-yl)imidazo[1,5-a]pyrazin-1-yl)-N-(4-propylpyridin-2-yl)benzamide | 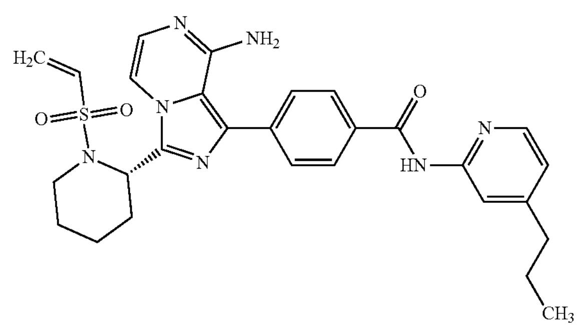 [SMILES: C=CS(=O)(=O)N1CCCC[C@H]1c1nc(-c2ccc(C(=O)Nc3cc(CCC)ccn3)cc2)c2c(N)nccn12] |
| 68. | (S)-4-(3-(1-acryloylpiperidin-2-yl)-8-aminoimidazo[1,5-a]pyrazin-1-yl)-N-(4-propylpyridin-2-yl)benzamide | 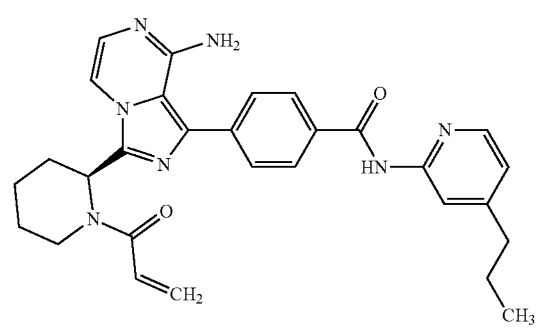 [SMILES: C=CC(=O)N1CCCC[C@H]1c1nc(-c2ccc(C(=O)Nc3cc(CCC)ccn3)cc2)c2c(N)nccn12] |

TABLE 1-continued

BTK Inhibitors

| No. | IUPAC Name | Structure |
| --- | --- | --- |
| 69. | (S)-4-(3-(1-acryloylpyrrolidin-2-yl)-8-aminoimidazo[1,5-a]pyrazin-1-yl)-N-(4-(trifluoromethyl)pyridin-2-yl)benzamide | 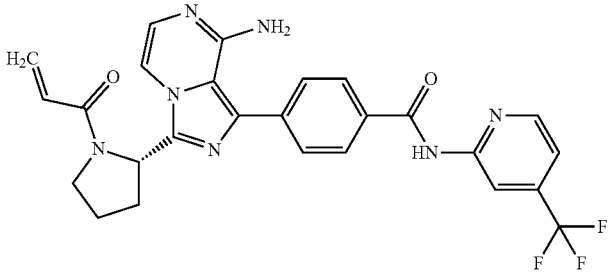 [SMILES: C=CC(=O)N1CCC[C@H]1c1nc(-c2ccc(C(=O)Nc3cc(C(F)(F)F)ccn3)cc2)c2c(N)nccn12] |
| 70. | (S)-4-(8-amino-3-(1-but-2-ynoylpiperidin-2-yl)imidazo[1,5-a]pyrazin-1-yl)-N-(4-(trifluoromethyl)pyridin-2-yl)benzamide | 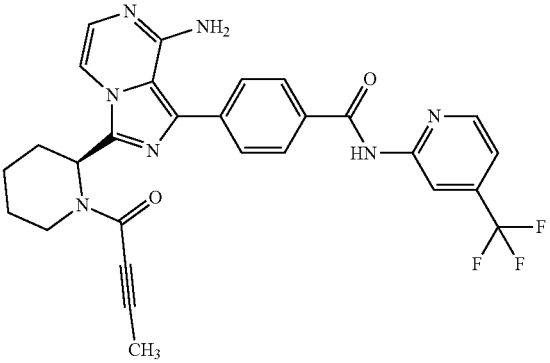 [SMILES: CC#CC(=O)N1CCCC[C@H]1c1nc(-c2ccc(C(=O)Nc3cc(C(F)(F)F)ccn3)cc2)c2c(N)nccn12] |
| 71. | (S)-4-(8-amino-3-(1-but-2-ynoylpiperidin-2-yl)imidazo[1,5-a]pyrazin-1-yl)-N-(4-propylpyridin-2-yl)benzamide | 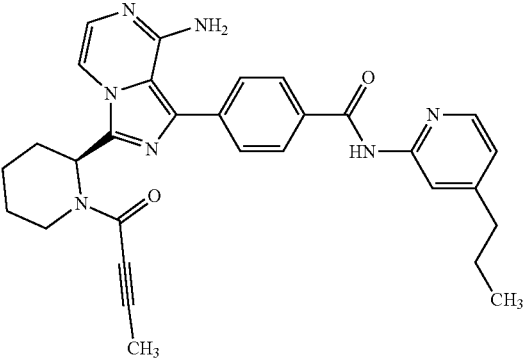 [SMILES: CC#CC(=O)N1CCCC[C@H]1c1nc(-c2ccc(C(=O)Nc3cc(CCC)ccn3)cc2)c2c(N)nccn12] |
| 72. | (S,E)-4-(8-amino-3-(1-(4-(dimethylamino)but-2-enoyl)pyrrolidin-2-yl)imidazo[1,5-a]pyrazin-1-yl)-N-(4-isopropylpyridin-2-yl)benzamide | 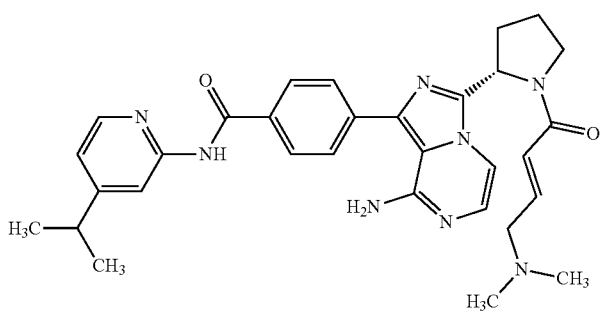 [SMILES: CC(C)c1ccnc(NC(=O)c2ccc(-c3nc([C@@H]4CCCN4C(=O)/C=C/CN(C)C)n4ccnc(N)c34)cc2)c1] |

TABLE 1-continued

BTK Inhibitors

| No. | IUPAC Name | Structure |
|---|---|---|
| 73. | 4-(8-amino-3-((S)-1-(vinylsulfonyl)piperidin-2-yl)imidazo[1,5-a]pyrazin-1-yl)-3-methyl-N-(pyridin-2-yl)benzamide | 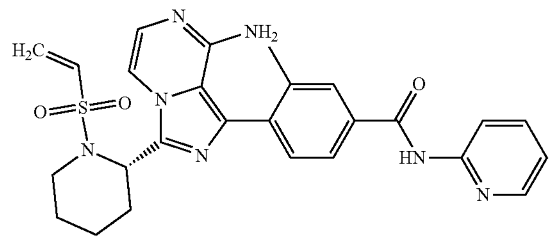 [SMILES: C=CS(=O)(=O)N1CCCC[C@H]1c1nc(-c2ccc(C(=O)Nc3ccccn3)cc2C)c2c(N)nccn12] |
| 74. | (S)-4-(8-amino-3-(1-but-2-ynoylpiperidin-2-yl)imidazo[1,5-a]pyrazin-1-yl)-2-fluoro-N-(4-propylpyridin-2-yl)benzamide | 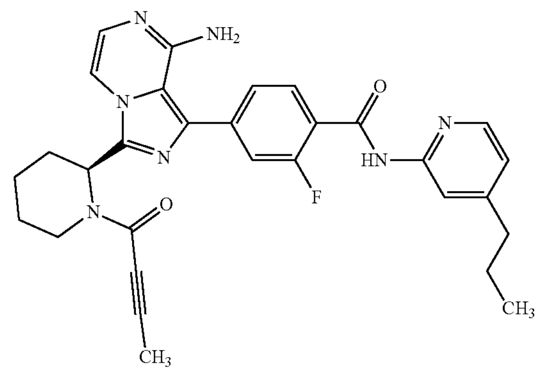 [SMILES: CC#CC(=O)N1CCCC[C@H]1c1nc(-c2ccc(C(=O)Nc3cc(CCC)ccn3)c(F)c2)c2c(N)nccn12] |
| 75. | (S,E)-4-(8-amino-3-(1-(4-methoxy-N-methylbut-2-enamido)ethyl)imidazo[1,5-a]pyrazin-1-yl)-N-(4-(trifluoromethyl)pyridin-2-yl)benzamide | 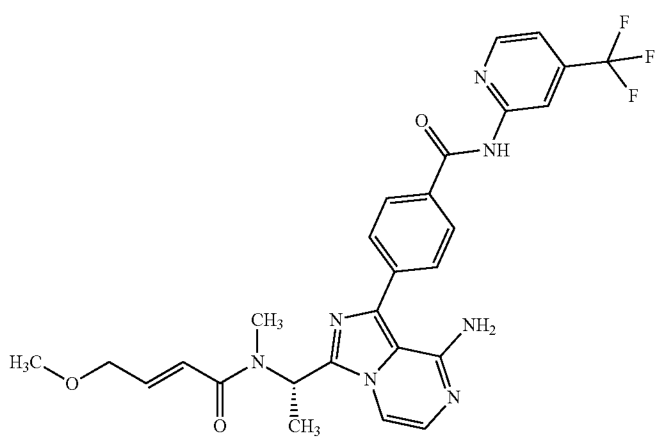 [SMILES: COC/C=C/C(=O)N(C)[C@@H](C)c1nc(-c2ccc(C(=O)Nc3cc(C(F)(F)F)ccn3)cc2)c2c(N)nccn12] |
| 76. | (S,E)-4-(8-amino-3-(1-(4-(dimethylamino)-N-methylbut-2-enamido)ethyl)imidazo[1,5-a]pyrazin-1-yl)-N-(4-propylpyridin-2-yl)benzamide | 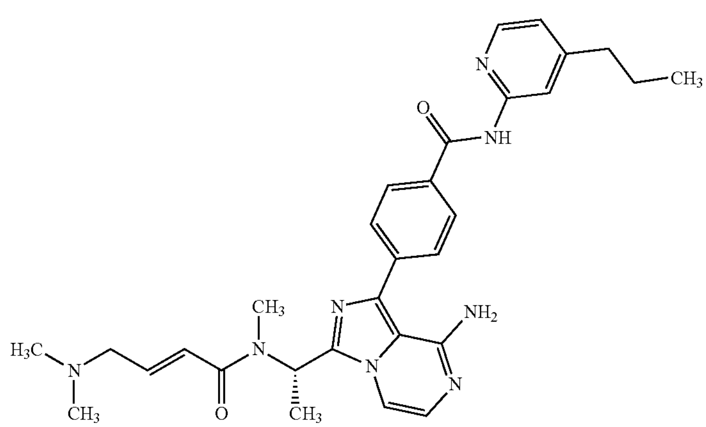 [SMILES: CCCc1ccnc(NC(=O)c2ccc(-c3nc([C@H](C)N(C)C(=O)/C=C/CN(C)C)n4ccnc(N)c34)cc2)c1] |

TABLE 1-continued

BTK Inhibitors

| No. | IUPAC Name | Structure |
|---|---|---|
| 77. | (S,E)-4-(8-amino-3-(1-(4-(pyrrolidin-1-yl)but-2-enoyl)pyrrolidin-2-yl)imidazo[1,5-a]pyrazin-1-yl)-N-(4-propylpyridin-2-yl)benzamide | 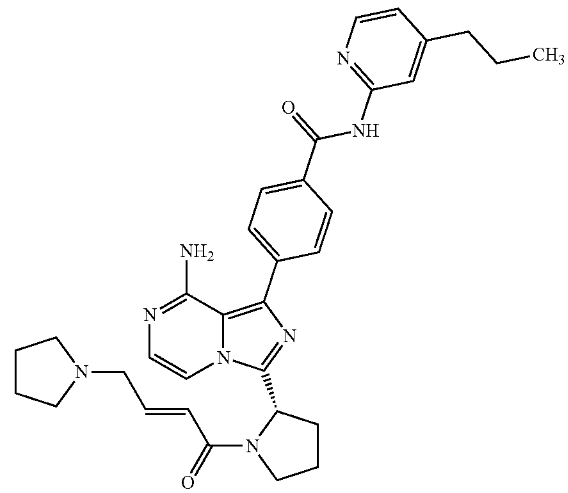 [SMILES: CCCc1ccnc(NC(=O)c2ccc(-c3nc([C@@H]4CCCN4C(=O)/C=C/CN4CCCC4)n4ccnc(N)c34)cc2)c1] |
| 78. | (S,E)-4-(8-amino-3-(1-(4-(dimethylamino)but-2-enoyl)piperidin-2-yl)imidazo[1,5-a]pyrazin-1-yl)-N-(pyridin-2-yl)benzamide | 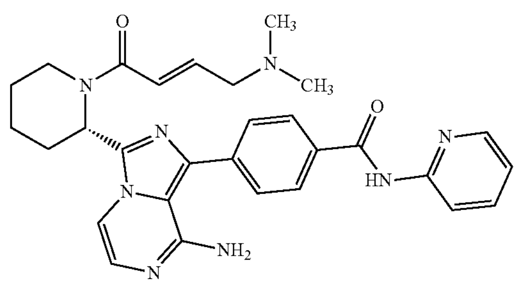 [SMILES: CN(C)C/C=C/C(=O)N1CCCC[C@H]1c1nc(-c2ccc(C(=O)Nc3ccccn3)cc2)c2c(N)nccn12] |
| 79. | (S)-4-(8-amino-3-(1-(2-chloropyrimidine-4-carbonyl)pyrrolidin-2-yl)imidazo[1,5-a]pyrazin-1-yl)-N-(4-propylpyridin-2-yl)benzamide | 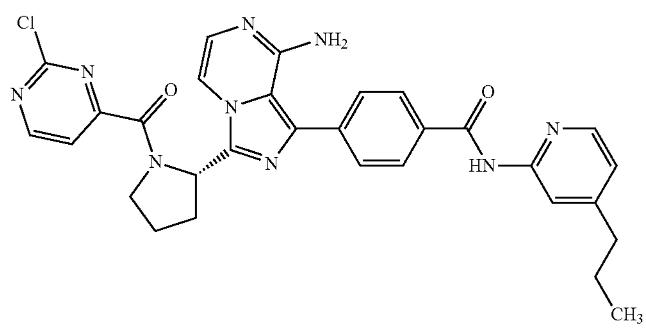 [SMILES: CCCc1ccnc(NC(=O)c2ccc(-c3nc([C@@H]4CCCN4C(=O)c4ccnc(Cl)n4)n4ccnc(N)c34)cc2)c1] |
| 80. | (S)-4-(3-(1-acrylamidoethyl)-8-aminoimidazo[1,5-a]pyrazin-1-yl)-N-(pyridin-2-yl)benzamide | 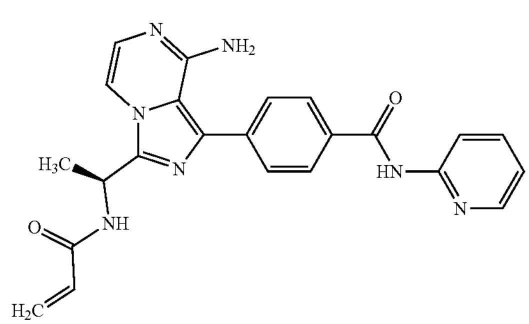 [SMILES: C=CC(=O)N[C@@H](C)c1nc(-c2ccc(C(=O)Nc3ccccn3)cc2)c2c(N)nccn12] |

US 12,414,950 B1

TABLE 1-continued

BTK Inhibitors

| No. | IUPAC Name | Structure |
|---|---|---|
| 81. | (S)-4-(3-(1-acryloylpyrrolidin-2-yl)-8-aminoimidazo[1,5-a]pyrazin-1-yl)-N-(thiazol-2-yl)benzamide | 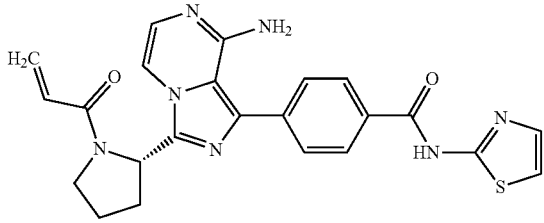 [SMILES: C=CC(=O)N1CCC[C@H]1c1nc(-c2ccc(C(=O)Nc3nccs3)cc2)c2c(N)nccn12] |
| 82. | (S)-4-(8-amino-3-(1-but-2-ynoylpyrrolidin-2-yl)imidazo[1,5-a]pyrazin-1-yl)-N-(4-isopropylpyridin-2-yl)benzamide | 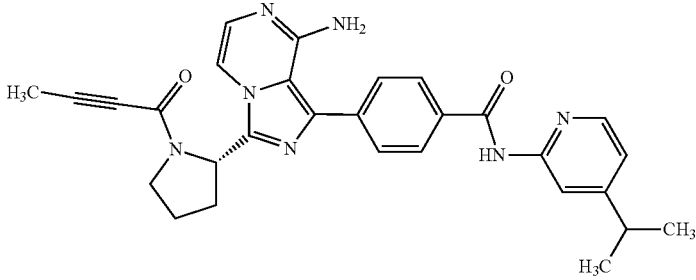 [SMILES: CC#CC(=O)N1CCC[C@H]1c1nc(-c2ccc(C(=O)Nc3cc(C(C)C)ccn3)cc2)c2c(N)nccn12] |
| 83. | (S)-4-(8-amino-3-(1-(2-chloropyrimidine-4-carbonyl)piperidin-2-yl)imidazo[1,5-a]pyrazin-1-yl)-N-(4-propylpyridin-2-yl)benzamide | 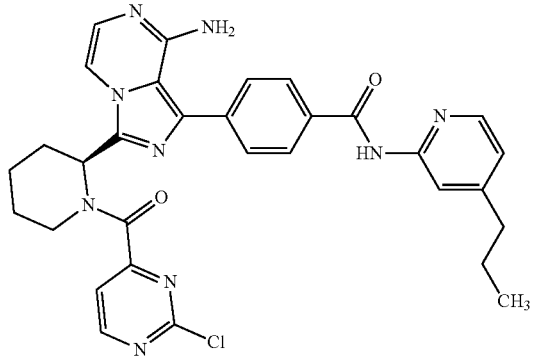 [SMILES: CCCc1ccnc(NC(=O)c2ccc(-c3nc([C@@H]4CCCCN4C(=O)c4ccnc(Cl)n4)n4ccnc(N)c34)cc2)c1] |
| 84. | (S,E)-4-(8-amino-3-(1-(4-methoxybut-2-enoyl)piperidin-2-yl)imidazo[1,5-a]pyrazin-1-yl)-N-(4-(trifluoromethyl)pyridin-2-yl)benzamide | 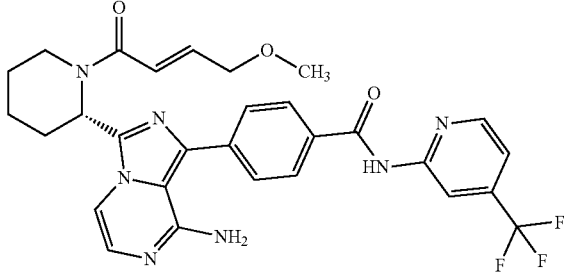 [SMILES: COC/C=C/C(=O)N1CCCC[C@H]1c1nc(-c2ccc(C(=O)Nc3cc(C(F)(F)F)ccn3)cc2)c2c(N)nccn12] |
| 85. | (S)-4-(3-(1-acryloylpiperidin-2-yl)-8-aminoimidazo[1,5-a]pyrazin-1-yl)-N-(4-(trifluoromethyl)pyridin-2-yl)benzamide | 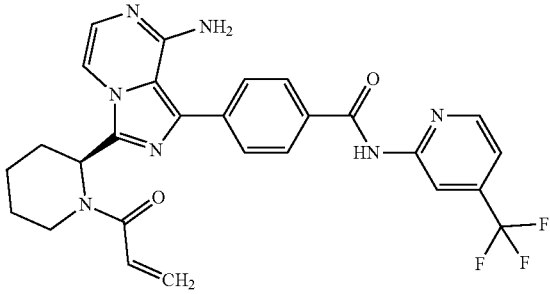 [SMILES: C=CC(=O)N1CCCC[C@H]1c1nc(-c2ccc(C(=O)Nc3cc(C(F)(F)F)ccn3)cc2)c2c(N)nccn12] |

TABLE 1-continued

BTK Inhibitors

| No. | IUPAC Name | Structure |
|---|---|---|
| 86. | (S)-4-(8-amino-3-(1-but-2-ynoylpiperidin-2-yl)imidazo[1,5-a]pyrazin-1-yl)-2-methoxy-N-(4-propylpyridin-2-yl)benzamide | 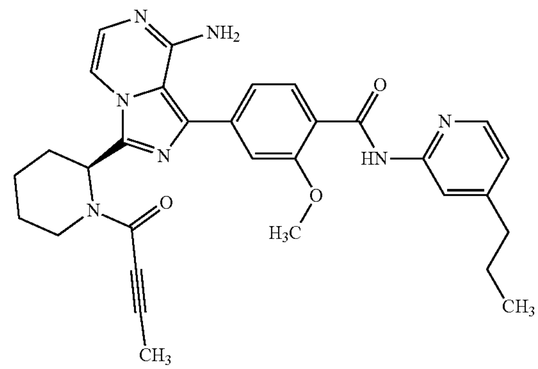 [SMILES: CC#CC(=O)N1CCCC[C@H]1c1nc(-c2ccc(C(=O)Nc3cc(CCC)ccn3)c(OC)c2)c2c(N)nccn12] |
| 87. | (S,E)-4-(8-amino-3-(1-(4-methoxybut-2-enoyl)piperidin-2-yl)imidazo[1,5-a]pyrazin-1-yl)-2-methoxy-N-(4-propylpyridin-2-yl) benzamide | 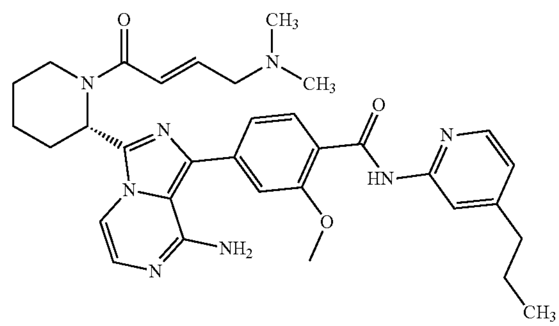 [SMILES: CCCc1ccnc(NC(=O)c2ccc(-c3nc([C@@H]4CCCCN4C(=O)/C=C/CN(C)C)n4ccnc(N)c34)cc2OC)c1] |
| 88. | (S)-4-(8-amino-3-(1-(2-chloropyrimidine-4-carbonyl)piperidin-2-yl)imidazo[1,5-a]pyrazin-1-yl)-N-(4-(trifluoromethyl)pyridin-2-yl)benzamide | 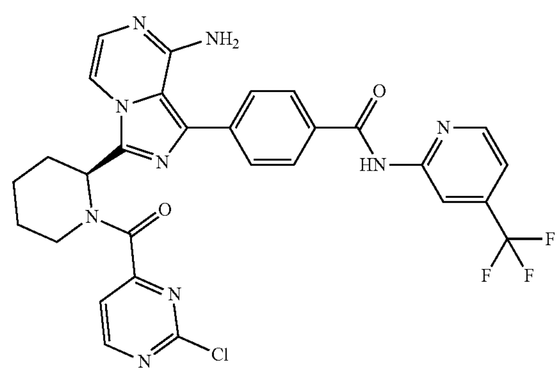 [SMILES: Nc1nccn2c([C@@H]3CCCCN3C(=O)c3ccnc(Cl)n3)nc(-c3ccc(C(=O)Nc4cc(C(F)(F)F)ccn4)cc3)c12] |
| 89. | (S)-4-(8-amino-3-(1-but-2-ynoylpiperidin-2-yl)imidazo[1,5-a]pyrazin-1-yl)-N-(5-ethylthiazol-2-yl)benzamide | 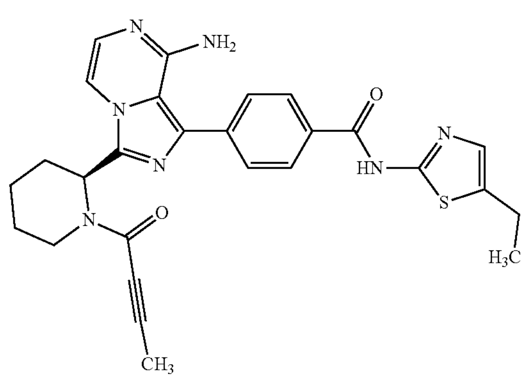 [SMILES: CC#CC(=O)N1CCCC[C@H]1c1nc(-c2ccc(C(=O)Nc3ncc(CC)s3)cc2)c2c(N)nccn12] |

TABLE 1-continued

BTK Inhibitors

| No. | IUPAC Name | Structure |
|---|---|---|
| 90. | (S)-4-(3-(1-acryloylpiperidin-2-yl)-8-aminoimidazo[1,5-a]pyrazin-1-yl)-N-(5-ethylthiazol-2-yl)benzamide | 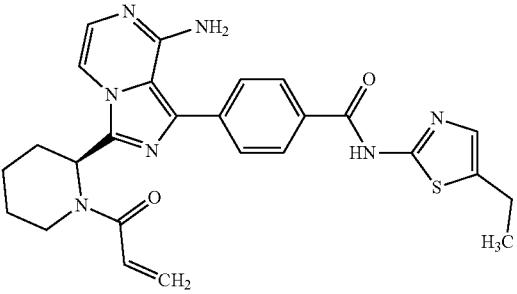 [SMILES: C=CC(=O)N1CCCC[C@H]1c1nc(-c2ccc(C(=O)Nc3ncc(CC)s3)cc2)c2c(N)nccn12] |
| 91. | (S)-4-(8-amino-3-(1-(2-chloropyrimidine-4-carbonyl)piperidin-2-yl)imidazo[1,5-a]pyrazin-1-yl)-N-(5-ethylthiazol-2-yl)benzamide | 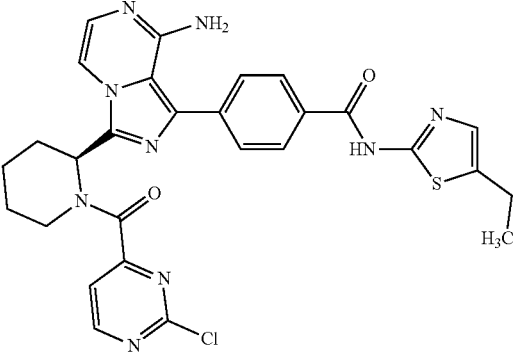 [SMILES: CCc1cnc(NC(=O)c2ccc(-c3nc([C@@H]4CCCCN4C(=O)c4ccnc(Cl)n4)n4ccnc(N)c34)cc2)s1] |
| 92. | (R,E)-4-(8-amino-3-(4-(4-methoxybut-2-enoyl)morpholin-3-yl)imidazo[1,5-a]pyrazin-1-yl)-N-(pyridin-2-yl)benzamide | 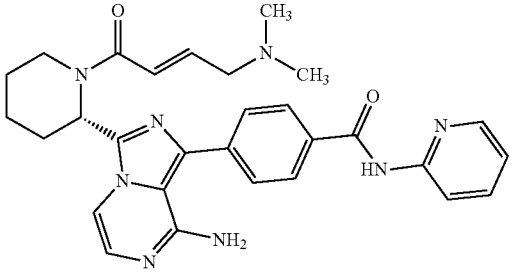 [SMILES: CN(C)C/C=C/C(=O)N1CCCC[C@H]1c1nc(-c2ccc(C(=O)Nc3ccccn3)cc2)c2c(N)nccn12] |
| 93. | (S,E)-4-(8-amino-3-(1-(4-methoxybut-2-enoyl)piperidin-2-yl)imidazo[1,5-a]pyrazin-1-yl)-N-(4-propylpyridin-2-yl)benzamide | 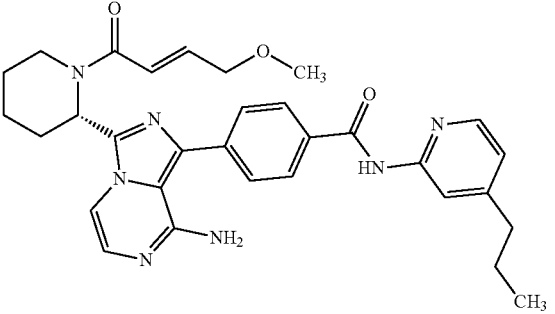 [SMILES: CCCc1ccnc(NC(=O)c2ccc(-c3nc([C@@H]4CCCCN4C(=O)/C=C/COC)n4ccnc(N)c34)cc2)c1] |
| 94. | (S)-4-(3-(1-acryloylpyrrolidin-2-yl)-8-aminoimidazo[1,5-a]pyrazin-1-yl)-N-(4-cyanopyridin-2-yl)benzamide | 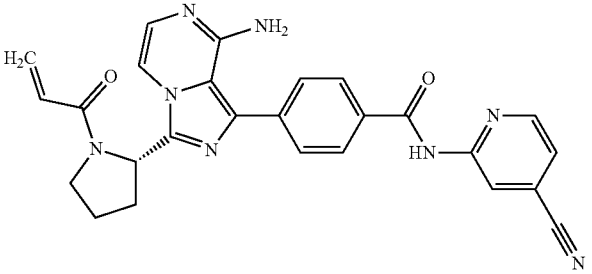 [SMILES: C=CC(=O)N1CCC[C@H]1c1nc(-c2ccc(C(=O)Nc3cc(C#N)ccn3)cc2)c2c(N)nccn12] |

TABLE 1-continued

BTK Inhibitors

| No. | IUPAC Name |
|---|---|
| 95. | (S)-4-(8-amino-3-(1-but-2-ynoylpyrrolidin-2-yl)imidazo[1,5-a]pyrazin-1-yl)-N-(4-methoxypyridin-2-yl)benzamide |
| 96. | (S)-4-(3-(1-acryloylpyrrolidin-2-yl)-8-aminoimidazo[1,5-a]pyrazin-1-yl)-N-(4-methylpyridin-2-yl)benzamide |
| 97. | (S)-4-(3-(1-acryloylpyrrolidin-2-yl)-8-aminoimidazo[1,5-a]pyrazin-1-yl)-N-(4-propylpyridin-2-yl)benzamide |
| 98. | (S)-4-(3-(1-acryloylpyrrolidin-2-yl)-8-aminoimidazo[1,5-a]pyrazin-1-yl)-N-(4-ethylpyridin-2-yl)benzamide |
| 99. | (S,E)-4-(8-amino-3-(1-(4-(dimethylamino)but-2-enoyl)pyrrolidin-2-yl)imidazo[1,5-a]pyrazin-1-yl)-N-(pyridin-2-yl)benzamide |

TABLE 1-continued

BTK Inhibitors

| No. | IUPAC Name | Structure |
|---|---|---|
| 100. | (S,E)-4-(8-amino-3-(1-(4-methoxybut-2-enoyl)pyrrolidin-2-yl)imidazo[1,5-a]pyrazin-1-yl)-N-(4-(trifluoromethyl)pyridin-2-yl)benzamide | 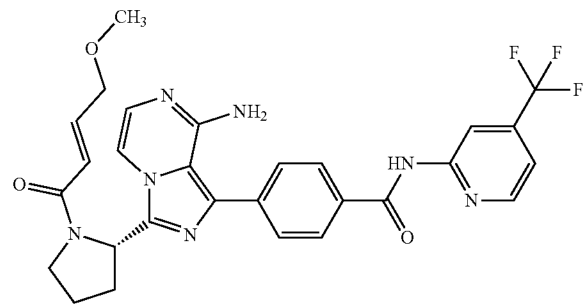 [SMILES: COC/C=C/C(=O)N1CCC[C@H]1c1nc(-c2ccc(C(=O)Nc3cc(C(F)(F)F)ccn3)cc2)c2c(N)nccn12] |
| 101. | (S)-4-(8-amino-3-(1-(2-chloropyrimidine-4-carbonyl)pyrrolidin-2-yl)imidazo[1,5-a]pyrazin-1-yl)-N-(4-methylpyridin-2-yl)benzamide | 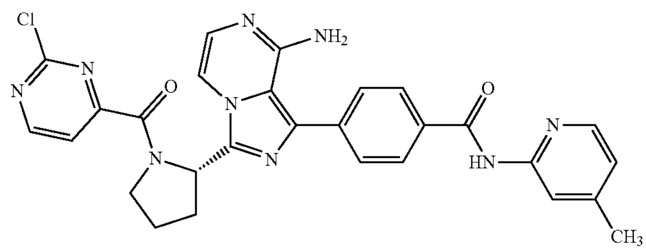 [SMILES: Cc1ccnc(NC(=O)c2ccc(-c3nc([C@@H]4CCCN4C(=O)c4ccnc(Cl)n4)n4ccnc(N)c34)cc2)c1] |
| 102. | (S)-4-(8-amino-3-(1-but-2-ynoylpyrrolidin-2-yl)imidazo[1,5-a]pyrazin-1-yl)-N-(4-cyanopyridin-2-yl)benzamide | 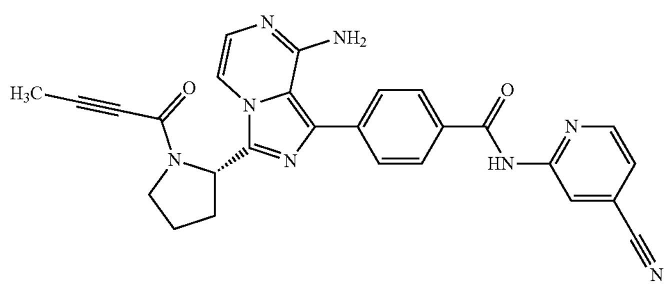 [SMILES: CC#CC(=O)N1CCC[C@H]1c1nc(-c2ccc(C(=O)Nc3cc(C#N)ccn3)cc2)c2c(N)nccn12] |
| 103. | (S)-4-(8-amino-3-(1-but-2-ynoylpyrrolidin-2-yl)imidazo[1,5-a]pyrazin-1-yl)-N-(4-ethylpyridin-2-yl)benzamide | 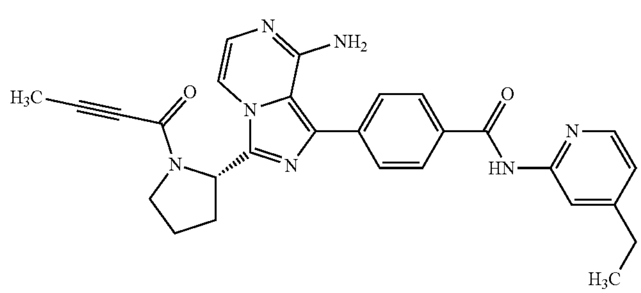 [SMILES: CC#CC(=O)N1CCC[C@H]1c1nc(-c2ccc(C(=O)Nc3cc(CC)ccn3)cc2)c2c(N)nccn12] |
| 104. | (S)-4-(8-amino-3-(1-but-2-ynoylpyrrolidin-2-yl)imidazo[1,5-a]pyrazin-1-yl)-N-(4-phenylpyridin-2-yl)benzamide | 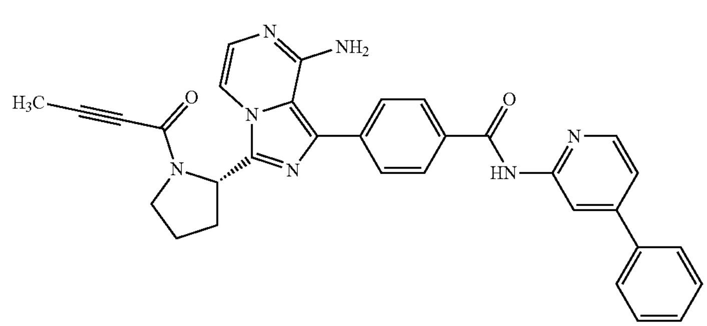 [SMILES: CC#CC(=O)N1CCC[C@H]1c1nc(-c2ccc(C(=O)Nc3cc(-c4ccccc4)ccn3)cc2)c2c(N)nccn12] |

TABLE 1-continued

BTK Inhibitors

| No. | IUPAC Name | Structure |
|-----|------------|-----------|
| 105. | (S)-4-(3-(1-acryloylpyrrolidin-2-yl)-8-aminoimidazo[1,5-a]pyrazin-1-yl)N-(4-phenylpyridin-2-yl)benzamide | 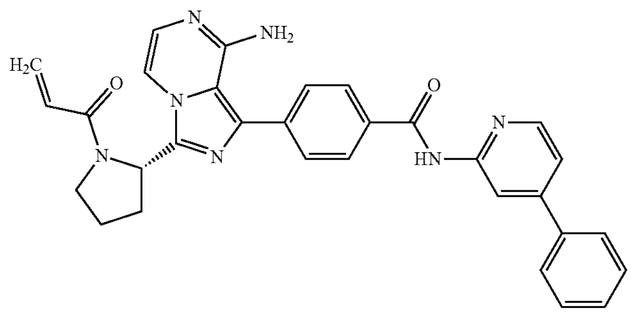 [SMILES: C=CC(=O)N1CCC[C@H]1c1nc(-c2ccc(C(=O)Nc3cc(-c4ccccc4)ccn3)cc2)c2c(N)nccn12] |
| 106. | (R,E)-1-(3-(4-amino-3-(4-phenoxyphenyl)-1H-pyrazolo[3,4-d]pyrimidin-1-yl)piperidin-1-yl)-4-(dimethylamino)but-2-en-1-one | 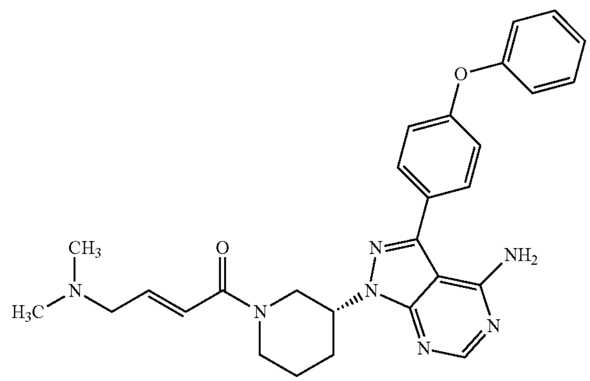 [SMILES: CN(C)C/C=C/C(=O)N1CCC[C@@H](n2nc(-c3ccc(Oc4ccccc4)cc3)c3c(N)ncnc32)C1] |
| 107. | (E)-1-(3-(4-amino-3-(4-phenoxyphenyl)-1H-pyrazolo[3,4-d]pyrimidin-1-yl)piperidin-1-yl)-4-morpholinobut-2-en-1-one | 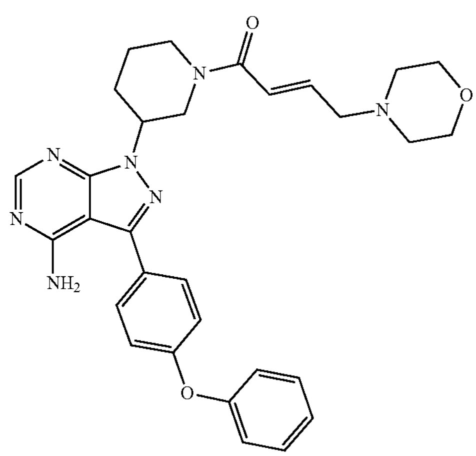 [SMILES: Nc1ncnc2c1c(-c1ccc(Oc3ccccc3)cc1)nn2C1CCCN(C(=O)/C=C/CN2CCOCC2)C1] |
| 108. | 1-(4-(4-amino-3-(4-phenoxyphenyl)-1H-pyrazolo[3,4-d]pyrimidin-1-yl)piperidin-1-yl)prop-2-en-1-one | 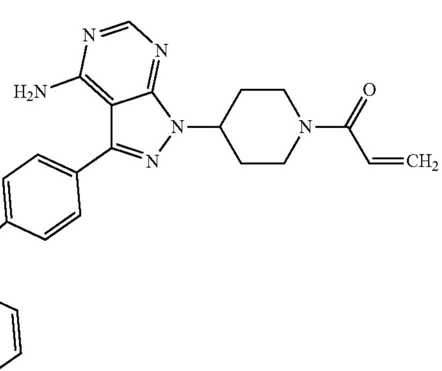 |

TABLE 1-continued

BTK Inhibitors

| No. | IUPAC Name | Structure |
|---|---|---|
| 109. | (E)-1-(4-(4-amino-3-(4-phenoxyphenyl)-1H-pyrazolo[3,4-d]pyrimidin-1-yl)piperidin-1-yl)-4-(dimethylamino)but-2-en-1-one | 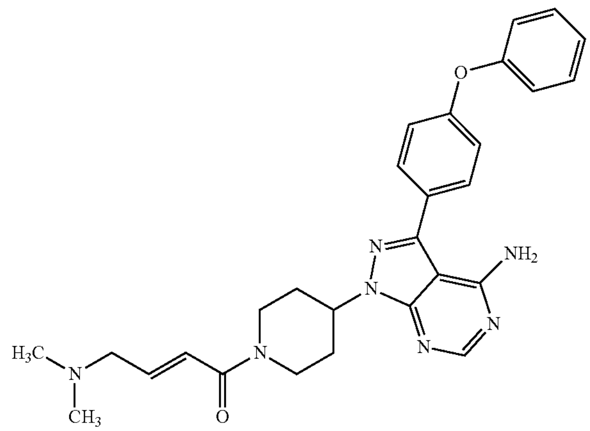 [SMILES: CN(C)C/C=C/C(=O)N1CCC(n2nc(-c3ccc(Oc4ccccc4)cc3)c3c(N)ncnc32)CC1] |
| 110. | (E)-N-((1s,4s)-4-(4-amino-3-(4-phenoxyphenyl)-1H-pyrazolo[3,4-d]pyrimidin-1-yl)cyclohexyl)-4-(dimethylamino)but-2-enamide | 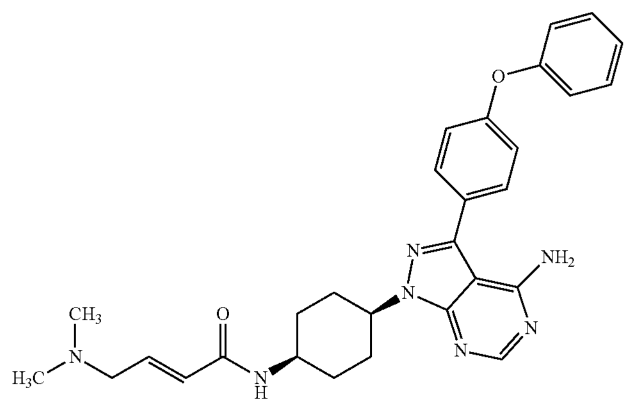 [SMILES: CN(C)C/C=C/C(=O)N[C@H]1CC[C@@H](n2nc(-c3ccc(Oc4ccccc4)cc3)c3c(N)ncnc32)CC1] |
| 111. | 1-(4-(4-amino-3-(4-phenoxyphenyl)-1H-pyrazolo[3,4-d]pyrimidin-1-yl)piperidin-1-yl)prop-2-en-1-one | 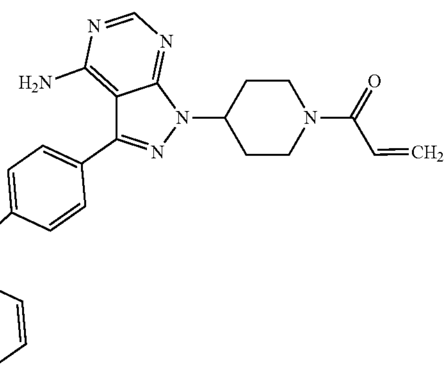 |
| 112. | N-((1r,4r)-4-(4-amino-3-(4-phenoxyphenyl)-1H-pyrazolo[3,4-d]pyrimidin-1-yl)cyclohexyl)acrylamide | 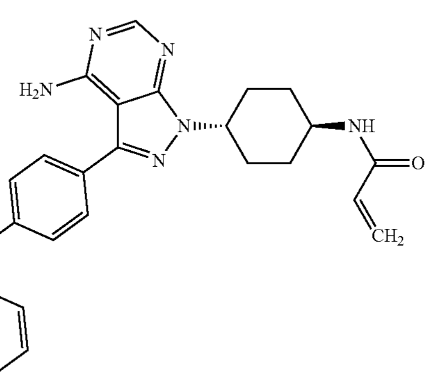 |

TABLE 1-continued

BTK Inhibitors

| No. | IUPAC Name | Structure |
|-----|------------|-----------|
| 113. | (E)-1-((R)-2-((4-amino-3-(4-phenoxyphenyl)-1H-pyrazolo[3,4-d]pyrimidin-1-yl)methyl)pyrrolidin-1-yl)-4-(dimethylamino)but-2-en-1-one | 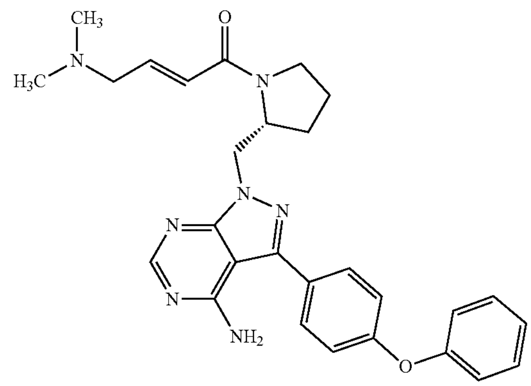 [SMILES: CN(C)C/C=C/C(=O)N1CCC[C@@H]1Cn1nc(-c2ccc(Oc3ccccc3)cc2)c2c(N)ncnc21] |
| 114. | (E)-1-((S)-2-((4-amino-3-(4-phenoxyphenyl)-1H-pyrazolo[3,4-d]pyrimidin-1-yl)methyl)pyrrolidin-1-yl)-4-(dimethylamino)but-2-en-1-one | 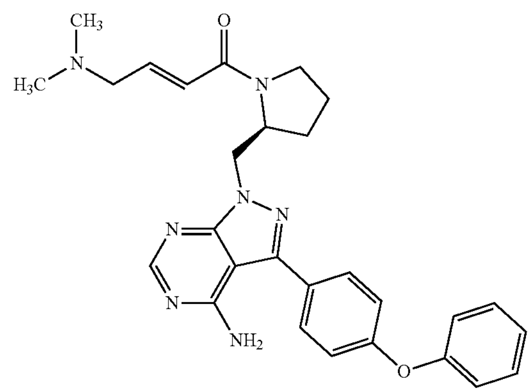 [SMILES: CN(C)C/C=C/C(=O)N1CCC[C@H]1Cn1nc(-c2ccc(Oc3ccccc3)cc2)c2c(N)ncnc21] |
| 115. | 1-((R)-2-((4-amino-3-(4-phenoxyphenyl)-1H-pyrazolo[3,4-d]pyrimidin-1-yl)methyl)pyrrolidin-1-yl)prop-2-en-1-one | 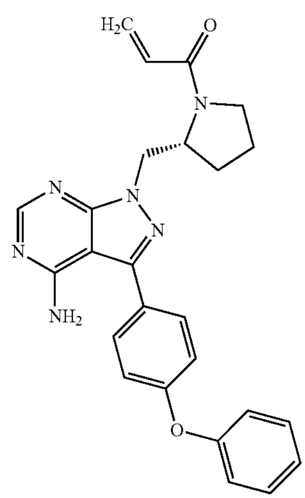 [SMILES: C=CC(=O)N1CCC[C@@H]1Cn1nc(-c2ccc(Oc3ccccc3)cc2)c2c(N)ncnc21] |

TABLE 1-continued

BTK Inhibitors

| No. | IUPAC Name | Structure |
|-----|------------|-----------|
| 116. | 1-((S)-2-((4-amino-3-(4-phenoxyphenyl)-1H-pyrazolo[3,4-d]pyrimidin-1-yl)methyl)pyrrolidin-1-yl)prop-2-en-1-one | 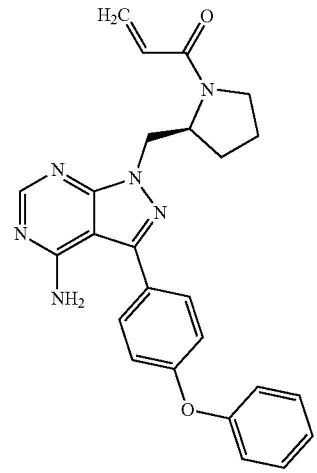 [SMILES: C=CC(=O)N1CCC[C@H]1Cn1nc(-c2ccc(Oc3ccccc3)cc2)c2c(N)ncnc21] |
| 117. | 1-((R)-2-((4-amino-3-(4-phenoxyphenyl)-1H-pyrazolo[3,4-d]pyrimidin-1-yl)methyl)pyrrolidin-1-yl)but-2-yn-1-one | 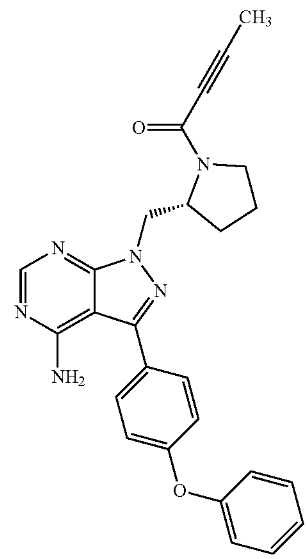 [SMILES: CC#CC(=O)N1CCC[C@@H]1Cn1nc(-c2ccc(Oc3ccccc3)cc2)c2c(N)ncnc21] |
| 118. | 1-((S)-2-((4-amino-3-(4-phenoxyphenyl)-1H-pyrazolo[3,4-d]pyrimidin-1-yl)methyl)pyrrolidin-1-yl)but-2-yn-1-one | 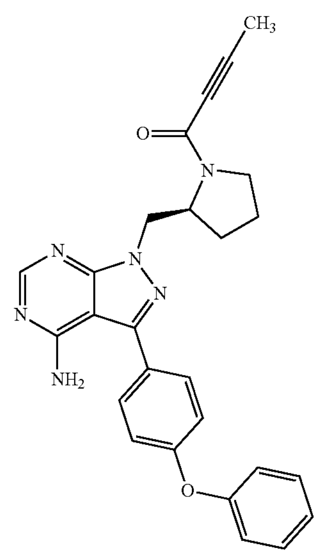 [SMILES: CC#CC(=O)N1CCC[C@H]1Cn1nc(-c2ccc(Oc3ccccc3)cc2)c2c(N)ncnc21] |

TABLE 1-continued

BTK Inhibitors

| No. | IUPAC Name | Structure |
|---|---|---|
| 119. | 1-((R)-3-(4-amino-3-(4-phenoxyphenyl)-1H-pyrazolo[3,4-d]pyrimidin-1-yl)piperidin-1-yl)but-2-yn-1-one | 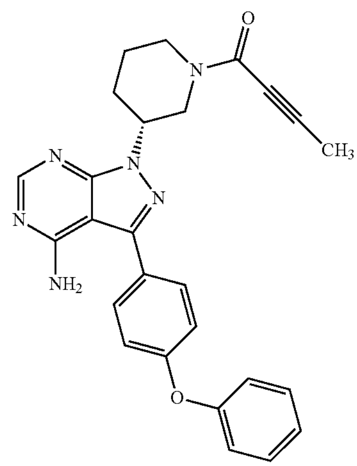 [SMILES: CC#CC(=O)N1CCC[C@@H](n2nc(-c3ccc(Oc4ccccc4)cc3)c3c(N)ncnc32)C1] |
| 120. | (E)-N-((1r,4r)-4-(4-amino-3-(4-phenoxyphenyl)-1H-pyrazolo[3,4-d]pyrimidin-1-yl)cyclohexyl-4-(dimethylamino))but-2-enamide | 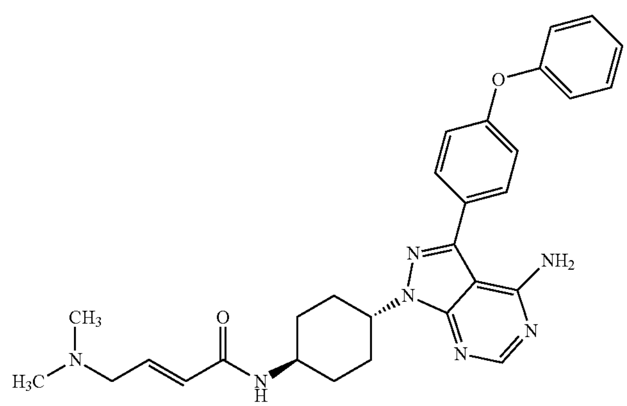 [SMILES: CN(C)C/C=C/C(=O)N[C@H]1CC[C@H](n2nc(-c3ccc(Oc4ccccc4)cc3)c3c(N)ncnc32)CC1] |
| 121. | N-(2-(4-amino-3-(4-phenoxyphenyl)-1H-pyrazolo[3,4-d]pyrimidin-1-yl)ethyl)-N-methylacrylamide | 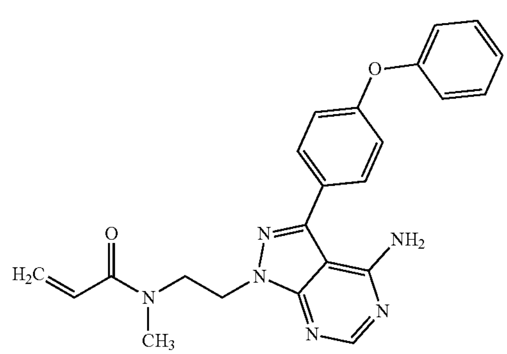 [SMILES: C=CC(=O)N(C)CCn1nc(-c2ccc(Oc3ccccc3)cc2)c2c(N)ncnc21] |

TABLE 1-continued

BTK Inhibitors

| No. | IUPAC Name | Structure |
|---|---|---|
| 122. | (E)-1-(4-(4-amino-3-(4-phenoxyphenyl)-1H-pyrazolo[3,4-d]pyrimidin-1-yl)-4-morpholino)but-2-en-1-one | 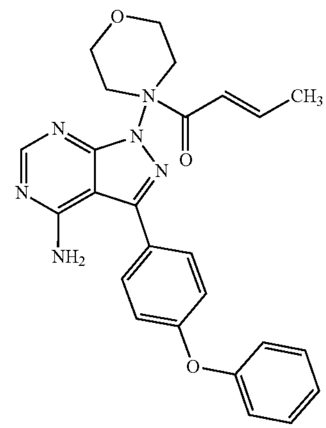 |
| 123. | (E)-1-(2-((S)-2-((4-amino-3-(4-phenoxyphenyl)-1H-pyrazolo[3,4-d]pyrimidin-1-yl)methyl)pyrrolidin-1-yl)morpholino)but-2-en-1-one | 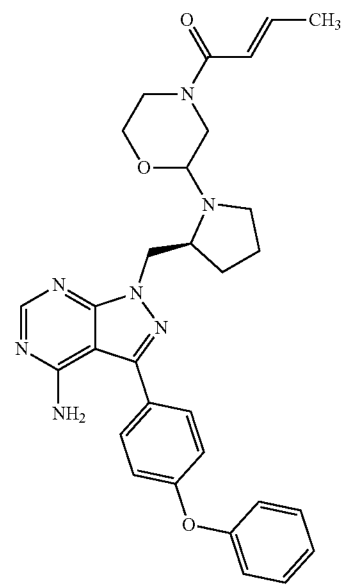 [SMILES: C/C=C/C(=O)N1CCOC(N2CCC[C@H]2Cn2nc(-c3ccc(Oc4ccccc4)cc3)c3c(N)ncnc32)C1] |
| 124. | N-((1s,4s)-4-(4-amino-3-(4-phenoxyphenyl)-1H-pyrazolo[3,4-d]pyrimidin-1-yl)cyclohexyl)but-2-ynamide | 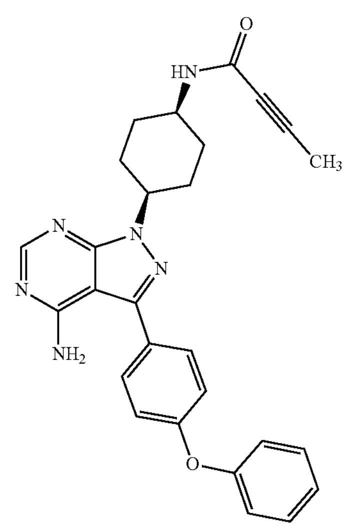 [SMILES: CC#CC(=O)N[C@H]1CC[C@@H](n2nc(-c3ccc(Oc4ccccc4)cc3)c3c(N)ncnc32)CC1] |

TABLE 1-continued

BTK Inhibitors

| No. | IUPAC Name | Structure |
|---|---|---|
| 125. | N-(2-(4-amino-3-(4-phenoxyphenyl)-1H-pyrazolo[3,4-d]pyrimidin-1-yl)ethyl)acrylamide | 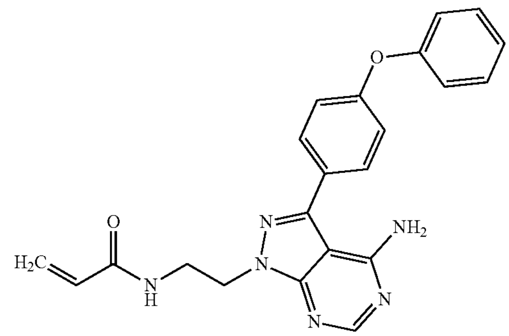 [SMILES: C=CC(=O)NCCn1nc(-c2ccc(Oc3ccccc3)cc2)c2c(N)ncnc21] |
| 126. | (E)-1-((R)-3-(4-amino-3-(4-phenoxyphenyl)-1H-pyrazolo[3,4-d]pyrimidin-1-yl)piperidin-1-yl)-4-morpholinobut-2-en-1-one | 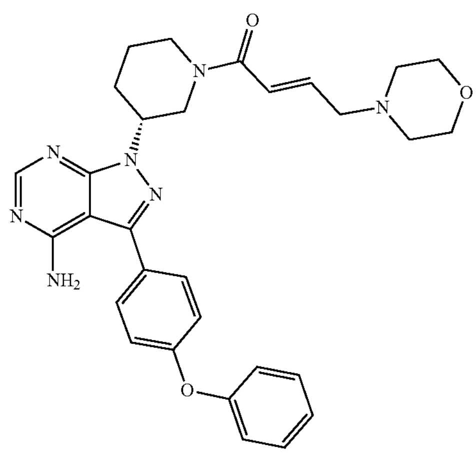 [SMILES: Nc1ncnc2c1c(-c1ccc(Oc3ccccc3)cc1)nn2[C@@H]1CCCN(C(=O)/C=C/CN2CCOCC2)C1] |
| 127. | (E)-N-((1s,4s)-4-(4-amino-3-(4-phenoxyphenyl)-1H-pyrazolo[3,4-d]pyrimidin-1-yl)cyclohexyl)-4-morpholinobut-2-enamide | 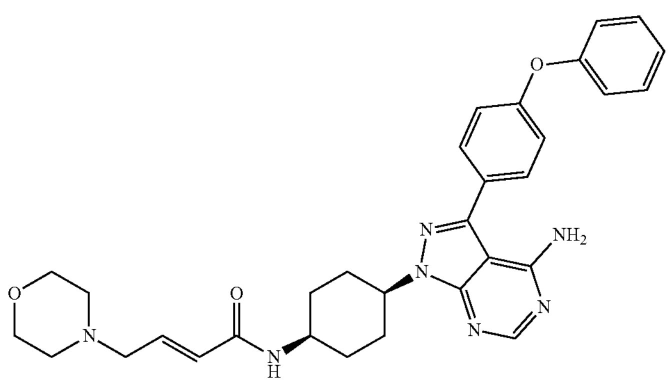 [SMILES: Nc1ncnc2c1c(-c1ccc(Oc3ccccc3)cc1)nn2[C@H]1CC[C@@H](NC(=O)/C=C/CN2CCOCC2)CC1] |
| 128. | 1-(4-(((6-amino-5-(4-phenoxyphenyl)pyrimidin-4-yl)amino)methyl)-4-fluoropiperidin-1-yl)prop-2-en-1-one | 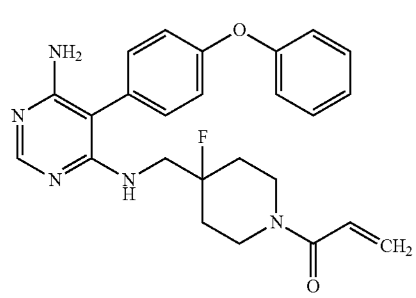 [SMILES: C=CC(=O)N1CCC(F)(CNc2ncnc(N)c2-c2ccc(Oc3ccccc3)cc2)CC1] |

TABLE 1-continued

BTK Inhibitors

| No. | IUPAC Name | Structure |
| --- | --- | --- |
| 129. | N-[3-[5-fluoro-2-[4-(2-methoxyethoxy)anilino]pyrimidin-4-yl]amino]phenyl]prop-2-enamide | 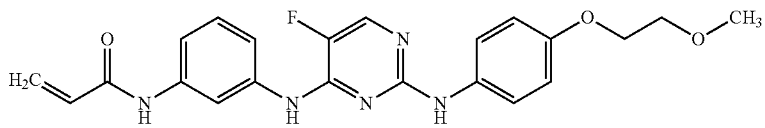 [SMILES: C=CC(=O)Nc1cccc(Nc2nc(Nc3ccc(OCCOC)cc3)ncc2F)c1] |
| 130. | 6-amino-9-[(3R)-1-but-2-ynoylpyrrolidin-3-yl]-7-(4-phenoxyphenyl)purin-8-one | 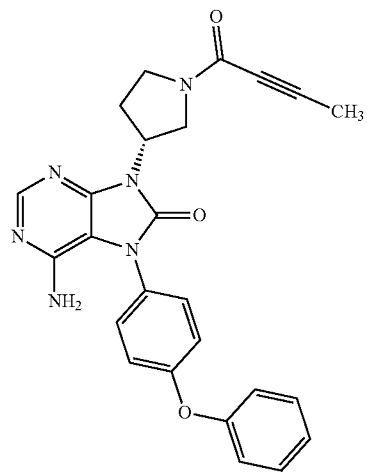 [SMILES: CC#CC(=O)N1CC[C@@H](n2c(=O)n(-c3ccc(Oc4ccccc4)cc3)c3c(N)ncnc32)C1] |
| 131. | (7S)-2-(4-phenoxyphenyl)-7-(1-prop-2-enoylpiperidin-4-yl)-4,5,6,7-tetrahydropyrazolo[1,5-a]pyrimidine-3-carboxamide | 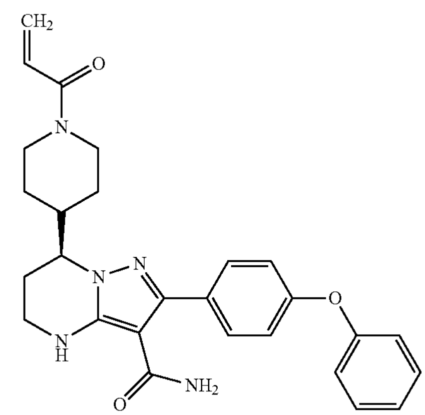 [SMILES: C=CC(=O)N1CCC([C@@H]2CCNc3c(C(N)=O)c(-c4ccc(Oc5ccccc5)cc4)nn32)CC1] |
| 132. | Orelabrutinib (2-(4-phenoxyphenyl)-6-(1-prop-2-enoylpiperidin-4-yl)pyridine-3-carboxamide) | 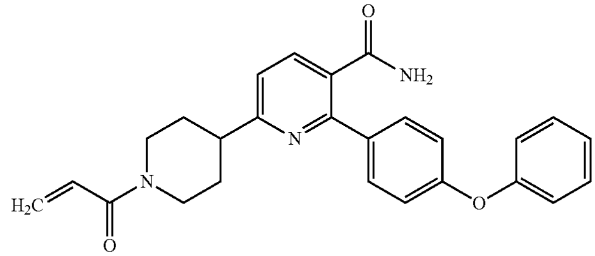 [SMILES: C=CC(=O)N1CCC(c2ccc(C(N)=O)c(-c3ccc(Oc4ccccc4)cc3)n2)CC1] |

TABLE 1-continued

BTK Inhibitors

| No. | IUPAC Name | Structure |
|---|---|---|
| 133. | Remibrutinib (N-[3-[6-amino-5-[2-[methyl(prop-2-enoyl)amino]ethoxy]pyrimidin-4-yl]-5-fluoro-2-methylphenyl]-4-cyclopropyl-2-fluorobenzamide) | 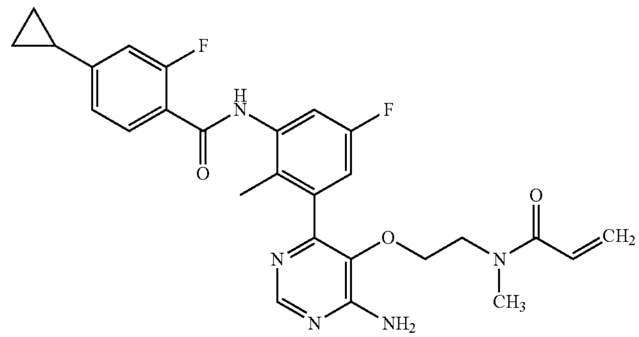 [SMILES: C=CC(=O)N(C)CCOc1c(N)ncnc1-c1cc(F)cc(NC(=O)c2ccc(C3CC3)cc2F)c1C] |
| 134. | Loxo-305 (1H-Pyrazole-4-carboxamide, 5-amino-3-[4-[[(5-fluoro-2-methoxybenzoyl)amino]methyl]phenyl]-1-[(1S)-2,2,2-trifluoro-1-methylethyl]) | 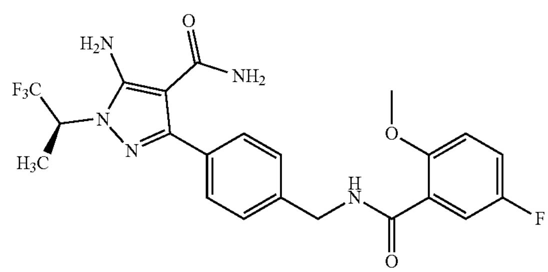 [SMILES: COc1ccc(F)cc1C(=O)NCc1ccc(-c2nn([C@@H](C)C(F)(F)F)c(N)c2C(N)=O)cc1] |
| 135. | TG-1701 (4-amino-1-[(3R)-1-but-2-ynoylpyrrolidin-3-yl]-3-[4-(2,6-difluorophenoxy)phenyl]-6H-pyrrolo[2,3-d]pyridazin-7-one) | 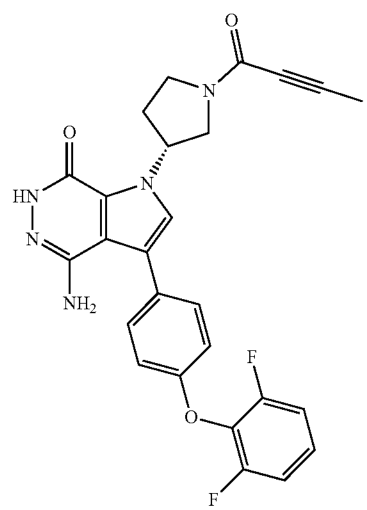 [SMILES: CC#CC(=O)N1CC[C@@H](n2cc(-c3ccc(Oc4c(F)cccc4F)cc3)c3c(N)n[nH]c(=O)c32)C1] |
| 136. | N-((1s,4s)-4-(4-amino-3-(4-phenoxyphenyl)-1H-pyrazolo[3,4-d]pyrimidin-1-yl)cyclohexyl)acrylamide | 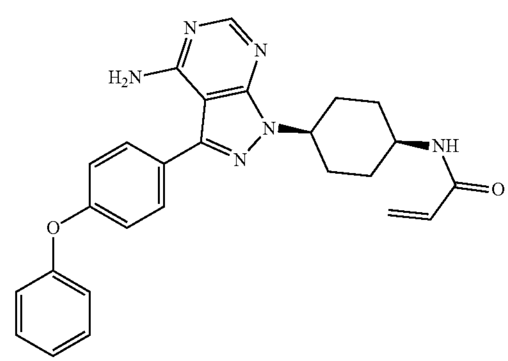 [SMILES: C=CC(=O)N[C@H]1CC[C@@H](n2nc(-c3ccc(Oc4ccccc4)cc3)c3c(N)ncnc32)CC1] |

TABLE 1-continued

BTK Inhibitors

| No. | IUPAC Name | Structure |
|---|---|---|
| 137. | N-((1r,4r)-4-(4-amino-3-(4-phenoxyphenyl)-1H-pyrazolo[3,4-d]pyrimidin-1-yl)cyclohexyl)but-2-ynamide | 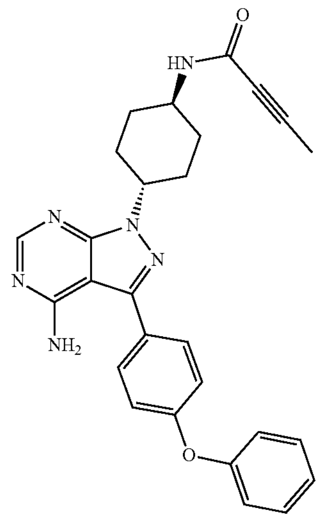 [SMILES: CC#CC(=O)N[C@H]1CC[C@H](n2nc(-c3ccc(Oc4ccccc4)cc3)c3c(N)ncnc32)CC1] |
| 138. | (E)-N-((1r,4r)-4-(4-amino-3-(4-phenoxyphenyl)-1H-pyrazolo[3,4-d]pyrimidin-1-yl)cyclohexyl)-4-morpholinobut-2-enamide | 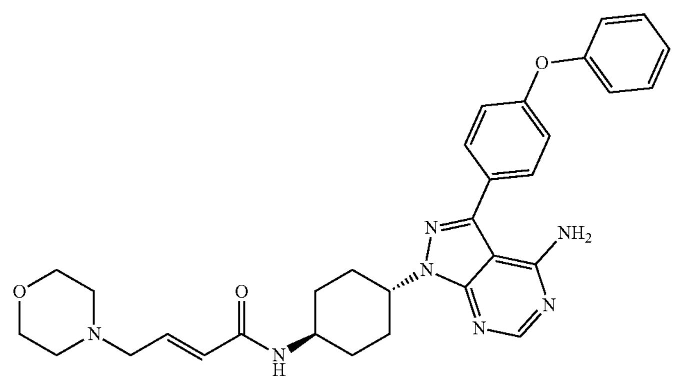 [SMILES: Nc1ncnc2c1c(-c1ccc(Oc3ccccc3)cc1)nn2[C@H]1CC[C@H](NC(=O)/C=C/CN2CCOCC2)CC1] |
| 139. | 2-[3-[2-amino-6-[1-(oxetan-3-yl)-3,6-dihydro-2H-pyridin-4-yl]-7H-pyrrolo[2,3-d]pyrimidin-4-yl]-2-(hydroxymethyl)phenyl]-6-cyclopropyl-8-fluoroisoquinolin-1-one | 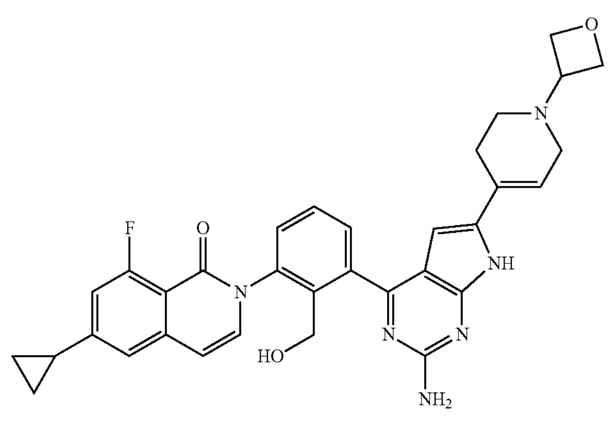 [SMILES: Nc1nc(-c2cccc(-n3ccc4cc(C5CC5)cc(F)c4c3=O)c2CO)c2cc(C3=CCN(C4COC4)CC3)[nH]c2n1] |

In an embodiment, the BTK inhibitor is a BTK-targeted proteolysis targeting chimera (PROTAC) (Arthur (2020) *Explor. Target Antitumor Ther.* 1, 131-152). In an embodiment, the BTK-targeted PROTAC comprises a BTK inhibitor moiety covalently coupled through a linker moiety to an ubiquitin protein ligase (E3) ligase-recruiting moiety. Such methods are known in the art, see for example, Bricelj (2021) *Front. Chem.* 9, 1-46. In an embodiment where the BTK inhibitor is a BTK-targeted PROTAC comprising a BTK inhibitor moiety, the BTK inhibitor moiety comprises a BTK inhibitor selected from the group consisting of the compounds listed in Table 1 or pharmaceutically-acceptable salt thereof. In an embodiment, the BTK inhibitor moiety is derived from a BTK inhibitor selected from the group consisting of the compounds listed in Table 1 or pharmaceutically-acceptable salt thereof. In an embodiment, the linker comprises polyethylene glycol (PEG). In an embodiment, the linker is 9 to 14 atoms in length, 10 to 12 atoms in length, or 11 atoms in length. In an embodiment, the E3 ligase-recruiting moiety comprises pomalidomide. In an embodiment, the E3 ligase-recruiting moiety is derived from pomalidomide. In an embodiment, the E3 ligase-recruiting moiety comprises lenalidomide. In an embodiment, the E3 ligase-recruiting moiety is derived from lenalidomide. In an embodiment, the E3 ligase-recruiting moiety comprises RG-71120. In an embodiment, the E3 ligase-recruiting moiety is derived from RG-71120. In an embodiment, the E3 ligase-recruiting moiety targets cereblon (CRBN). In an embodiment, the E3 ligase-recruiting moiety targets murine double-minute 2 (MDM2). In an embodiment, the E3 ligase-recruiting moiety targets Von Hippel-Landau (VHL). In an embodiment, the E3 ligase-recruiting moiety targets inhibitor of apoptosis protein (IAP).

In an embodiment, the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically-acceptable salt thereof.

In an embodiment, the disclosure relates to a method of treating ISM in a human subject that comprises the step of administering to said human subject a therapeutically effective amount of a BTK inhibitor compound selected from Table 1 or a pharmaceutically acceptable salt thereof, in a dosage selected from the group consisting of 10 mg QD, 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 10 mg BID, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the disclosure relates to a method of treating ISM in a human subject that comprises the step of administering to said human subject a therapeutically effective amount of a BTK inhibitor compound selected from Table 1 or a pharmaceutically acceptable salt thereof, in a dosage selected from the group consisting of at least about 10 mg QD, at least about 15 mg QD, at least about 25 mg QD, at least about 30 mg QD, at least about 50 mg QD, at least about 60 mg QD, at least about 75 mg QD, at least about 90 mg QD, at least about 100 mg QD, at least about 120 mg QD, at least about 150 mg QD, at least about 175 mg QD, at least about 180 mg QD, at least about 200 mg QD, at least about 225 mg QD, at least about 240 mg QD, at least about 250 mg QD, at least about 275 mg QD, at least about 300 mg QD, at least about 325 mg QD, at least about 350 mg QD, at least about 360 mg QD, at least about 375 mg QD, at least about 480 mg QD, at least about 10 mg BID, at least about 15 mg BID, at least about 25 mg BID, at least about 30 mg BID, at least about 50 mg BID, at least about 60 mg BID, at least about 75 mg BID, at least about 90 mg BID, at least about 100 mg BID, at least about 120 mg BID, at least about 150 mg BID, at least about 175 mg BID, at least about 180 mg BID, at least about 200 mg BID, at least about 225 mg BID, at least about 240 mg BID, at least about 250 mg BID, at least about 275 mg BID, at least about 300 mg BID, at least about 325 mg BID, at least about 350 mg BID, at least about 360 mg BID, at least about 375 mg BID, and at least about 480 mg BID.

In an embodiment, the disclosure relates to a use of a BTK inhibitor or a pharmaceutically acceptable salt thereof, in the manufacture of a medicament for treating ISM, wherein the treating comprises the step of administering to a human subject one or more doses of a BTK inhibitor compound selected from Table 1 or a pharmaceutically acceptable salt thereof.

The methods described above may be used as first-line treatment of ISM, in conjunction with or after treatment with conventional therapy, including treatment with anti-histamines, chemotherapy or stem cell transplant. In an embodiment, the BTK inhibitor is administered as a monotherapy. In an embodiment, the BTK inhibitor is administered in combination with the best supportive care for ISM.

In an embodiment, the human subject has previously failed prior treatment for ISM. In an embodiment, the human subject is a non-responder to prior treatment for ISM. In an embodiment, the human subject is treatment resistant to prior treatment for ISM. In an embodiment, the prior treatment for ISM is selected from the group consisting of histamine H1 blockers, histamine H2 blockers, leukotriene inhibitors, cromolyn sodium, corticosteroids and omalizumab. In an embodiment, the human subject is resistant to best supportive care for ISM.

Exemplary histamine H1 blockers include, but are not limited to, alkylamines such as brompheniramine, chlorpheniramine, dimethindene, pheniramine, triprolidine and acrivastine; piperazines such as buclizine, cyclizine, hydroxyzine, meclizine, oxatomide, cetirizine, and levocetirizine; piperidines such as zatadine, cyproheptadine, diphenylpyraline, ketotifen, astemizole, bilastine, desloratadine, ebastine, fexofenadine, levocabastine, loratadine, mizolastine, olopatadine, rupatadine and terfenadine; ethanolamines such as carbinoxamine, clemastine, dimenhydrinate, diphenhydramine, doxylamine and phenyltoloxamine; ethylenediamines such as antazoline, pyrilamine and tripelennamine; and phenothiazines such as methdilazine and promethazine. Other exemplary histamine H1 blockers include, but are not limited to, doxepin, azelastine, emedastine and epinastine. Exemplary histamine H2 blockers include, but are not limited to, cimetidine, famotidine, nizatidine and ranitidine.

In an embodiment, wherein the human subject is ISM treatment naïve. In certain embodiments, the invention relates to a method for reducing the percentage of activated basophils, BTK phosphorylation (pBTK) in basophils and IgE-mediated IL-4 production from basophils in a human subject having at least one symptom associated with ISM or at least one mast cell mediator-related symptom by administering to the subject a BTK inhibitor (e.g. compound 128 or a pharmaceutically acceptable salt thereof), wherein administration of the BTK inhibitor to the subject reduces the percentage of activated basophils, pBTK in basophils and IgE-mediated IL-4 production from basophils to less than 60%, less than 50%, less than 40%, less than 30%, less than 20%, less than 10%, less than 5%, less than 4%, less than 3%, less than 2%, or less than 1% of the total basophil population and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g. compound 128 or a pharmaceutically acceptable salt thereof), wherein the percentage of activated basophils, pBTK in basophils and IgE-mediated IL-4 production from basophils in the subject is reduced to less than 60%, less than 50%, less than 40%, less than 30%, less than 20%, less than 10%, less than 5%, less than 4%, less than 3%, less than 2%, or less than 1% of the total basophil population, and wherein administration of the BTK inhibitor reduces or alleviates at least one symptom associated with ISM or at least one mast cell mediator-related symptom. In one embodiment, the human subject has a KIT D816V mutation. Methods for determining the percentage of activated basophils in a sample from a patient are known in the art and include assessing the percentage of basophils expressing cell surface CD63 or CD203c after allergen activation. Method for determining percentage of pBTK in basophils from a patient include calculating the pBTK levels normalized as a percentage of stimulated control after allergen activation. Method for determining the percentage of IgE-mediated IL-4 production in basophils from a patient include calculating the IL-4 levels normalized as a percentage of stimulated control after allergen activation.

In certain embodiments, the invention relates to a method for reducing the percentage of activated mast cells, pBTK in mast cells, chemotaxis of mast cells and FcεRI expression in mast cells in a human subject having at least one symptom associated with ISM or at least one mast cell mediator-related symptom by administering to the subject a BTK inhibitor (e.g. compound 128 or a pharmaceutically acceptable salt thereof), wherein administration of the BTK inhibitor to the subject reduces the percentage of activated mast cells, pBTK in mast cells, chemotaxis of mast cells and FcεRI expression in mast cells to less than 60%, less than 50%, less than 40%, less than 30%, less than 20%, less than 10%, less than 5%, less than 4%, less than 3%, less than 2%, or less than 1% of the total mast cell population and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g., compound 128 or a pharmaceutically acceptable salt thereof), wherein the percentage of activated mast cells, pBTK in mast cells, chemotaxis of mast cells and FcεRI expression in mast cells in the subject is reduced to less than 60%, less than 50%, less than 40%, less than 30%, less than 20%, less than 10%, less than 5%, less than 4%, less than 3%, less than 2%, or less than 1% of the total mast cell population, and wherein administration of the BTK inhibitor reduces or alleviates at least one symptom associated with ISM or at least one mast cell mediator-related symptom. In one embodiment, the human subject has a KIT D816V mutation. Methods for determining the percentage of activated mast cells in a sample from a patient are known in the art and include assessing the percentage of mast cells expressing cell surface CD63 normalized as a percentage of stimulated control after allergen activation. Method for determining percentage of pBTK in mast cells from a patient include calculating the pBTK levels normalized as a percentage of stimulated control after allergen activation. Method for determining percentage of mast cell chemotaxis from a patient include calculating the number of cells migrating to conditioned media made from mast cells activated with an allergen normalized as a percentage of stimulated control. Method for determining percentage of FcεRI expression in mast cells from a patient include calculating the FcεRI levels normalized as a percentage of stimulated control after allergen activation.

In certain embodiments, the invention relates to a method for inhibiting anti-IgE induced basophil activation in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject inhibits anti-IgE induced basophil activation to less than 60%, less than 50%, less than 40%, less than 30%, less than 20%, less than 10%, less than 5%, less than 4%, less than 3%, less than 2%, or less than 1% of the total basophil population and wherein administration of the BTK inhibitor to the subject reduces or alleviates at least one symptom associated with ISM or at least one mast cell mediator-related symptom. In certain embodiments, the invention relates to a method for inhibiting anti-IgE induced basophil activation, the method comprising administering a BTK inhibitor to the human subject (e.g., compound 128 or a pharmaceutically acceptable salt thereof), wherein the percentage of activated basophils in the subject is reduced to less than 60%, less than 50%, less than 40%, less than 30%, less than 20%, less than 10%, less than 5%, less than 4%, less than 3%, less than 2%, or less than 1% of the total basophil population, and wherein administration of the BTK inhibitor reduces or alleviates at least one symptom associated with ISM or at least one mast cell mediator-related symptom. In one embodiment, the human subject has a KIT D816V mutation.

In certain embodiments, the invention relates to a method for inhibiting an IgE-induced cytosolic $Ca^{2+}$ influx in the mast cells in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject inhibits an IgE-induced cytosolic $Ca^{2+}$ influx in the mast cells an increase of less than about 5%, an increase of less than about 10%, an increase of less than about 15%, an increase of less than about 20%, an increase of less than about 25%, an increase of less than about 30%, an increase of less than about 35%, an increase of less than about 40%, an increase of less than about 45%, or an increase of less than about 50%, and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g., compound 128 or a pharmaceutically acceptable salt thereof), wherein administration of the BTK inhibitor inhibits an IgE-induced cytosolic $Ca^{2+}$ influx in the mast cells of the human subject, and wherein inhibition of the IgE-induced cytosolic $Ca^{2+}$ influx reduces or alleviates at least one symptom associated with ISM or at least one mast cell mediator-related symptom. In certain embodiments, the IgE-induced cytosolic $Ca^{2+}$ influx in mast cells of the human subject is an increase of less than about 5%, an increase of less than about 10%, an increase of less than about 15%, an increase of less than about 20%, an increase of less than about 25%, an increase of less than about 30%, an increase of less than about 35%, an increase of less than about 40%, an increase of less than about 45%, or an increase of less than about 50%. In one embodiment, the human subject has a KIT D816V mutation. Methods for determining the percentage of cytosolic $Ca^{2+}$ influx in the mast cells in a sample from a patient include calculating the area under the curve (AUC) of the $Ca^{2+}$ influx profile and normalizing the AUC as a percentage of stimulated control after allergen activation.

In certain embodiments, the invention relates to a method of inhibiting IgE-induced calcium influx into the mast cells in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject reduces an IgE-induced cytosolic $Ca^{2+}$ influx in the mast cells an increase by at least about 30%, at least about 40%, at least about 50%, at least about 60%, at least about 70%, at least about 80%, at least about 85%, at least about 90%, at least about 95%, or at least about 99%, and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g., compound 128 or a pharmaceutically acceptable salt thereof), wherein administration of the BTK inhibitor inhibits an IgE-induced calcium influx into the mast cells of the human subject, and wherein inhibition of an IgE-induced calcium influx reduces or alleviates at least one symptom associated with ISM or at least one mast cell mediator-related symptom. In certain embodiments, an IgE-induced calcium influx in mast cells of the human subject is reduced by at least about 30%, at least about 40%, at least about 50%, at least about 60%, at least about 70%, at least about 80%, at least about 85%, at least about 90%, at least about 95%, or at least about 99%. In one embodiment, the human subject has a KIT D816V mutation. Methods for determining the percentage of cytosolic $Ca^{2+}$ influx in the mast cells in a sample from a patient include calculating the AUC of the $Ca^{2+}$ influx profile and normalizing the AUC as a percentage of stimulated control after allergen activation.

In certain embodiments, the invention relates to a method of inhibiting IgE-induced degranulation in the mast cells in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject reduces IgE-induced in the mast cells by at least about 30%, at least about 40%, at least about 50%, at least about 60%, at least about 70%, at least about 80%, at least about 85%, at least about 90%, at least about 95%, or at least about 99%, and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g., compound 128 or a pharmaceutically acceptable salt thereof), wherein administration of the BTK inhibitor inhibits IgE-induced degranulation in the mast cells of the human subject, and wherein inhibition of an IgE-induced degranulation reduces or alleviates at least one symptom associated with ISM or at least one mast cell mediator-related symptom. In certain embodiments, IgE-induced degranulation in mast cells of the human subject is reduced by at least about 30%, at least about 40%, at least about 50%, at least about 60%, at least about 70%, at least about 80%, at least about 85%, at least about 90%, at least about 95%, or at least about 99%. In one embodiment, the human subject has a KIT D816V mutation. Methods for determining the percentage of degranulation in mast cells in a sample from a patient include calculating the percentage of mast cells expressing cell surface CD63 and levels of mediators (e.g. histamine) released from granules normalized as a percentage of stimulated control after allergen activation.

In certain embodiments, the invention relates to a method of inhibiting IgE-mediated cytokine production from mast cells in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject reduces IgE-mediated cytokine production by at least about 30%, at least about 40%, at least about 50%, at least about 60%, at least about 70%, at least about 80%, at least about 85%, at least about 90%, at least about 95%, or at least about 99%, and wherein administration of the BTK inhibitor to the subject reduces or alleviates at least one symptom associated with ISM or at least one mast cell mediator-related symptom. In certain embodiments, the cytokine is IL-8, MCP-1, MIP-1a, IL-10, or IL13. In certain embodiments, the invention relates to a method for treating a human subject having ISM, the method comprising administering a BTK inhibitor to the human subject (e.g., compound 128 or a pharmaceutically acceptable salt thereof), wherein administration of the BTK inhibitor inhibits IgE-mediated cytokine production from the mast cells of the human subject, and wherein inhibition of an IgE-mediated cytokine production reduces or alleviates at least one symptom associated with ISM or at least one mast cell mediator-related symptom. In certain embodiments, the cytokine is IL-8, MCP-1, MIP-1a, IL-10, or IL13. In certain embodiments, IgE-mediated cytokine production in mast cells of the human subject is reduced by at least about 30%, at least about 40%, at least about 50%, at least about 60%, at least about 70%, at least about 80%, at least about 85%, at least about 90%, at least about 95%, or at least about 99%. In one embodiment, the human subject has a KIT D816V mutation. FcεRI, the receptor for IgE, is only expressed by mast cells and basophils. Therefore, IgE-mediated cytokine production would only be from mast cells and basophils. Methods for determining the percentage of cytokine production in mast cells in a sample from a patient include calculating the levels of cytokines produced normalized as a percentage of stimulated control after allergen activation.

In certain embodiments, the invention relates to a method of inhibiting IgE-induced histamine release from mast cells in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject reduces IgE-induced histamine release in the mast cells by at least about 30%, at least about 40%, at least about 50%, at least about 60%, at least about 70%, at least about 80%, at least about 85%, at least about 90%, at least about 95%, or at least about 99%, and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g., compound 128 or a pharmaceutically acceptable salt thereof), wherein administration of the BTK inhibitor inhibits IgE-induced histamine release from the mast cells of the human subject, and wherein inhibition of an IgE-induced histamine release from the mast cells reduces or alleviates at least one symptom associated with ISM or at least one mast cell mediator-related symptom. In certain embodiments, IgE-induced histamine release in mast cells of the human subject is reduced by at least about 30%, at least about 40%, at least about 50%, at least about 60%, at least about 70%, at least about 80%, at least about 85%, at least about 90%, at least about 95%, or at least about 99%. In one embodiment, the human subject has a KIT D816V mutation. Methods for determining the percentage of histamine release from mast cells in a sample from a patient include calculating the levels of histamine released from granules normalized as a percentage of stimulated control after allergen activation.

In certain embodiments, the invention relates to a method of inhibiting IgE-induced histamine release from basophil cells in a human subject having at least one symptom associated with ISM or at least one mast cell mediator-related symptom by administering to the subject a BTK inhibitor (e.g., compound 128 or a pharmaceutically acceptable salt thereof), wherein administration of the BTK inhibitor to the subject reduces IgE-induced histamine release from the basophil cells by at least about 30%, at least about 40%, at least about 50%, at least about 60%, at least about 70%, at least about 80%, at least about 85%, at least about 90%, at least about 95%, or at least about 99%, and wherein administration of the BTK inhibitor to the subject reduces or alleviates at least one symptom associated with ISM or at least one mast cell mediator-related symptom. In certain embodiments, the invention relates to a method for treating a human subject having ISM, the method comprising administering a BTK inhibitor to the human subject (e.g., compound 128 or a pharmaceutically acceptable salt thereof), wherein administration of the BTK inhibitor inhibits IgE-induced histamine release from the basophil cells of the human subject, and wherein inhibition of an IgE-induced histamine release from the basophil cells reduces or alleviates at least one symptom associated with ISM or at least one mast cell mediator-related symptom. In certain embodiments, IgE-induced histamine release in basophil cells of the human subject is reduced by at least about 30%, at least about 40%, at least about 50%, at least about 60%, at least about 70%, at least about 80%, at least about 85%, at least about 90%, at least about 95%, or at least about 99%. In one embodiment, the human subject has a KIT D816V mutation.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce release of tryptase by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce release of tryptase by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the BTK inhibitor comprises 1-(4-(((6-amino-5-(4-phenoxyphenyl) pyrimidin-4-yl)amino)methyl)-4-fluoropiperidin-1-yl)prop-2-en-1-one (Compound 128) or a pharmaceutically acceptable salt thereof.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce bone marrow mast cell burden by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the BTK inhibitor comprises 1-(4-(((6-amino-5-(4-phenoxyphenyl)pyrimidin-4-yl) amino)methyl)-4-fluoropiperidin-1-yl)prop-2-en-1-one (Compound 128) or a pharmaceutically acceptable salt thereof.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce bone marrow mast cell burden by about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the leukotrienes release from cells in the human subject. In some embodiments, the cells comprise mast cells. In some embodiments, the cells comprise basophils. In some embodiments, the leukotrienes release is IgE-induced. In some embodiments, the BTK inhibitor comprises 1-(4-(((6-amino-5-(4-phenoxyphenyl) pyrimidin-4-yl)amino)methyl)-4-fluoropiperidin-1-yl)prop-2-en-1-one (Compound 128) or a pharmaceutically acceptable salt thereof. In some embodiments, the amount of leukotrienes released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of leukotrienes released prior to the treatment.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the cytokine release from cells in the human subject. In some embodiments, the cells comprise mast cells. In some embodiments, the cells comprise basophils. In some embodiments, the cytokine release is IgE-induced. In some embodiments, the BTK inhibitor comprises 1-(4-(((6-amino-5-(4-phenoxyphenyl)pyrimidin-4-yl) amino)methyl)-4-fluoropiperidin-1-yl)prop-2-en-1-one (Compound 128) or a pharmaceutically acceptable salt thereof. In some embodiments, the amount of cytokine released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of cytokine released prior to the treatment. In some embodiments, the cytokine is IL-8, MCP-1, MIP-1a, IL-10, IL-13, or a combination thereof.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the tryptase release from cells in the human subject. In some embodiments, the cells comprise mast cells. In some embodiments, the cells comprise basophils. In some embodiments, the tryptase release is IgE-induced. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof. In some embodiments, the amount of tryptase released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of tryptase released prior to the treatment.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the prostaglandins release from cells in the human subject. In some embodiments, the cells comprise mast cells. In some embodiments, the cells comprise basophils. In some embodiments, the prostaglandins release is IgE-induced. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof. In some embodiments, the amount of prostaglandins released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of prostaglandins released prior to the treatment.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the kinins release from cells in the human subject. In some embodiments, the cells comprise mast cells. In some embodiments, the cells comprise basophils. In some embodiments, the kinins release is IgE-induced. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof. In some embodiments, the amount of kinins released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of kinins released prior to the treatment.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the serotonin release from cells in the human subject. In some embodiments, the cells comprise mast cells. In some embodiments, the cells comprise basophils. In some embodiments, the serotonin release is IgE-induced. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof. In some embodiments, the amount of serotonin released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of serotonin released prior to the treatment.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the heparin release from cells in the human subject. In some embodiments, the cells comprise mast cells. In some embodiments, the cells comprise basophils. In some embodiments, the heparin release is IgE-induced. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof. In some embodiments, the amount of heparin released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of heparin released prior to the treatment.

In certain embodiments, the invention relates to a method for treating a human subject having ISM, the method comprising administering a BTK inhibitor to the human subject (e.g., compound 128 or a pharmaceutically acceptable salt thereof), wherein the BTK inhibitor is administered in an amount sufficient to reduce the serine proteases release from cells in the human subject. In some embodiments, the cells comprise mast cells. In some embodiments, the cells comprise basophils. In some embodiments, the serine proteases release is IgE-induced. In some embodiments, the BTK inhibitor comprises 1-(4-(((6-amino-5-(4-phenoxyphenyl)pyrimidin-4-yl)amino)methyl)-4-fluoropiperidin-1-yl)prop-2-en-1-one (Compound 128) or a pharmaceutically acceptable salt thereof. In some embodiments, the amount of serine proteases released after treating with a BTK inhibitor is about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of serine proteases released prior to the treatment.

Symptoms of ISM

In some embodiments, the disclosure relates to a method of reducing or alleviating at least one symptom associated with ISM, such as fatigue, abdominal pain, diarrhea, nausea, skin spots, itching, flushing, brain fog, headache, dizziness, bone pain, or a combination thereof. In some embodiments, the severity of each symptom associated with ISM, such as fatigue, abdominal pain, diarrhea, nausea, skin spots, itching, flushing, brain fog, headache, dizziness, bone pain via a symptom assessment form (e.g. ISM-TSAF (Table 2) or SISM-TSAF (Table 3)) where patients rate the severity of symptoms experienced over the last 24 hours on a zero to ten score, with zero indicating an absence of the symptom and ten indicating extreme severity of such symptom. In some embodiments, the disclosure relates to a method of reducing or alleviating at least a symptom selected from fatigue, abdominal pain, diarrhea, nausea, skin spots, itching, flushing, brain fog, headache, dizziness, bone pain, or a combination thereof in a human subject with ISM comprising administering to the human subject an amount of a BTK inhibitor effective to reduce or alleviate the symptom. In an embodiment, the BTK inhibitor is compound 128.

In some embodiments, the disclosure relates to a method of reducing or alleviating at least one symptom associated with ISM, such as muscle pain, difficulty concentrating, runny nose, nasal congestion, wheezing, shortness of breath, throat itching, heart palpitations, diarrhea, or a combination thereof. In some embodiments, the disclosure relates to a method of reducing or alleviating at least one symptom selected from muscle pain, difficulty concentrating, runny nose, nasal congestion, wheezing, shortness of breath, throat itching, heart palpitations, diarrhea, or a combination thereof in a human subject with ISM comprising administering to the human subject an amount of a BTK inhibitor effective to reduce or alleviate the symptom. In some embodiments, the severity of each symptom associated with ISM, such as muscle pain, difficulty concentrating, runny nose, nasal congestion, wheezing, shortness of breath, throat itching, heart palpitations, diarrhea is quantified via symptom assessment form (e.g. ISM-TSAF (Table 2) or SISM-TSAF (Table 3)) where patients rate the severity of symptoms experienced over the last 24 hours on a zero to ten score, with zero indicating an absence of the symptom and ten indicating extreme severity of such symptom. In an embodiment, the BTK inhibitor is compound 128 or a pharmaceutically acceptable salt thereof.

In some embodiments, the invention relates to a method of reducing or alleviating at least one symptom associated with ISM, such as itching, skin redness and/or swelling, flushing, diarrhea and/or loose stools, fatigue and/or exhaustion, headache, muscle and/or joint pain, difficulty concentrating, or a combination thereof. In some embodiments, the disclosure relates to a method of reducing or alleviating at least one symptom selected from itching, skin redness and/or swelling, flushing, diarrhea and/or loose stools, fatigue and/or exhaustion, headache, muscle and/or joint pain, difficulty concentrating, or a combination thereof in a human subject with ISM comprising administering to the human subject an amount of a BTK inhibitor effective to reduce or alleviate the symptom. In an embodiment, the BTK inhibitor is compound 128 or a pharmaceutically acceptable salt thereof.

In an embodiment, the invention relates to a method of reducing the frequency and/or severity of anaphylactic reactions in an ISM patient comprising administration of a BTK inhibitor. In an embodiment, the anaphylactic reactions are allergen induced anaphylactic reactions. In an embodiment, the BTK inhibitor is compound 128 or a pharmaceutically acceptable salt thereof.

In some embodiments, the disclosure relates to a method of reducing or alleviating at least one symptom associated with ISM, such as fatigue, abdominal pain, diarrhea, nausea, skin spots, itching, flushing, brain fog, headache, dizziness, bone pain, muscle pain, difficulty concentrating, runny nose, nasal congestion, wheezing, shortness of breath, throat itching, heart palpitations or a combination thereof. In some embodiments, the severity of each symptom associated with ISM, such as fatigue, abdominal pain, diarrhea, nausea, skin spots, itching, flushing, brain fog, headache, dizziness, bone pain, muscle pain, difficulty concentrating, runny nose, nasal congestion, wheezing, shortness of breath, throat itching, heart palpitations via a symptom assessment form (e.g. ISM-TSAF (Table 2) or SISM-TSAF (Table 3)) where patients rate the severity of symptoms experienced over the last 24 hours on a zero to ten score, with zero indicating an absence of the symptom and ten indicating extreme severity of such symptom. In some embodiments, the disclosure relates to a method of reducing or alleviating at least a symptom selected from fatigue, abdominal pain, diarrhea, nausea, skin spots, itching, flushing, brain fog, headache, dizziness, bone pain, muscle pain, difficulty concentrating, runny nose, nasal congestion, wheezing, shortness of breath, throat itching, heart palpitations, or a combination thereof in a human subject with ISM comprising administering to the human subject an amount of a BTK inhibitor effective to reduce or alleviate the symptom. In an embodiment, the BTK inhibitor is compound 128 or a pharmaceutically acceptable salt thereof.

In some embodiments, the symptom persists for at least one day prior to administration of the BTK inhibitor, such as at least two days, at least three days, at least four days, at least five days, at least six days, or at least seven days prior to administration of the BTK inhibitor.

In some embodiments, the method further comprises assessing the severity of the symptom prior to administration of the BTK inhibitor. In some embodiments, the method further comprises assessing the severity of the symptom after administration of the BTK inhibitor. In some embodiments, severity of the symptom is determined by self-assessment. In some embodiments, severity of the symptom is determined by self-reporting.

In some embodiments, the severity of a symptom is assessed by assigning a numerical value (which may also be referred to as a score) to the severity of the symptom, for example, by assigning a value on a scale of zero to ten, wherein a value of zero indicates that a symptom is absent and a value of ten indicates that a symptom's severity is the most severe to the human subject. In some embodiments, a total symptom score is determined by summing the scores for each individual symptom. In some embodiments, the scores of two, three, four, five, six, seven, eight, nine, ten or eleven symptoms are summed to obtain a total symptom score. In some embodiments, a symptom score or a total symptom score is obtained by reporting a score (for example, on a scale of zero to 10) in response to one, two, three, four, five, six, seven, eight, nine, ten, or eleven of the following questions relating to the presence and severity of symptoms associated with ISM.

TABLE 2

Symptom Assessment Questionnaire
(ISM-TSAF)
Symptom (1) fatigue
(2) abdominal pain
(3) diarrhea TABLE 2-continued Symptom Assessment Questionnaire
(ISM-TSAF)
Symptom (4) nausea
(5) skin spots
(6) itching
(7) flushing
(8) brain fog
(9) headache
(10) dizziness
(11) bone pain In some embodiments, the human subject is considered symptomatic and has a total symptom score equaling a sum of the scores of each of the eleven questions in Table 2, wherein each question is scored on a scale of zero to ten with zero indicating the symptom is absent and ten indicating the symptom is the most severe, of at least 14, such at least 15, at least 16, at least 18, at least 20, at least 22, at least 24, at least 25, at least 26, at least 28, at least 30, at least 32, at least 34, at least 35, at least 36, at least 38, at least 40, at least 42, at least 44, at least 45, at least 46, at least 48, and/or at least 50.

In some embodiments, a symptom score or a total symptom score is obtained by reporting a score (for example, on a scale of zero to ten) in response to one, two, three, four, five, six, seven, eight, or nine questions regarding the severity of the following symptoms over the past 24 hours (Table 3 excluding question 9). In some embodiments, the symptoms of "runny nose", "nasal congestion", and "throat itching" are treated as allergic symptoms; the total allergic symptom score is the sum of the score on each of the allergic symptom. The symptoms of "wheezing", "shortness of breath", and "heart palpitation" are considered as respiratory symptoms; the total respiratory symptom score is the sum of the score on each of the respiratory symptom. In some embodiments, the total allergic symptom score is highly correlated with the total respiratory symptom score. In some embodiments, the reduction of the total allergic symptom score is indicative of that of the total respiratory symptom score. In some embodiments, the reduction of the total respiratory symptom score is indicative of that of total allergic symptom score. In some embodiments, the disclosure relates to administration of Compound 128 for treating ISM in a human in need thereof, wherein the total allergic symptom score or a total respiratory symptom score is reduced by at least 18%, such as at least 20%, at least 30%, at least 40%, at least 50%, such as at least 60%, at least 70%, at least 75%, at least 80%, and/or at least 90% compared to a baseline total allergic symptom score or total respiratory symptom score.

In some embodiments, the symptoms listed here may have corresponding medical terms, and they are interchangeable. For example, the medical term for "runny nose" is "rhinorrhea"; the medical term for "throat itching" is "pharyngeal pruritus"; the medical term for "wheezing" is "sibilant rhonchi"; the medical term for "shortness of breath" is "dyspnea"; the medical term for "difficulty concentrating" is "cognitive impairment" or "attention deficit"; the medical term for "muscle pain" is "myalgia"; the medical term for "itching" is "pruritus"; the medical term for "flushing" is "erythema"; the medical term for "headache" is "cephalalgia"; the medical term for "bone pain" is "ostealgia" or "osteodynia".

TABLE 3

Supplemental Symptom Assessment
Questionnaire (SISM-TSAF)
Symptom (1) muscle pain
(2) runny nose
(3) nasal congestion
(4) wheezing
(5) shortness of breath
(6) throat itching
(7) heart palpitations
(8) difficulty concentrating
(9) occasions of diarrhea In some embodiments, the human subject is considered symptomatic and has a total symptom score equaling a sum of the scores of each of questions 1-8 (excluding question 9) in Table 3, wherein each question 1-8 is scored on a scale of zero to ten with zero indicating the symptom is absent and ten indicating the symptom is the most severe, of at least 12, such at least 14, at least 15, at least 16, at least 18, at least 20, at least 22, at least 24, at least 25, at least 26, at least 28, at least 30, at least 32, at least 34, at least 35, at least 36, at least 38, at least 40, at least 42, at least 44, at least 45, at least 46, at least 48, and/or at least 50. In some embodiments, the total symptom score equaling a sum of the scores of each of questions 1-8 (excluding question 9) in Table 3 are highly correlated with the total symptom score calculated from the responses to the questions 1-11 in Table 2. In some embodiments, the total symptom score calculated based on the responses to the questions 1-8 (excluding question 9) in Table 3 serves as a proxy for the total symptom score calculated from the responses to the questions 1-11 in Table 2.

In some embodiments, a symptom is reduced if the symptom's score is reduced by at least 10%, such as at least 15%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, compared to a baseline score for the symptom. In some embodiments, the baseline score for a symptom is the symptom's score before administering a BTK inhibitor as described herein. In some embodiments, the disclosure relates to a reduction in a total symptom score. In some embodiments, a total symptom score is reduced if the total symptom score is reduced by at least 18%, such as at least 20%, at least 30%, at least 40%, at least 50%, such as at least 60%, at least 70%, at least 75%, at least 80%, and/or at least 90% compared to a baseline total symptom score. In some embodiments, a total symptom score is reduced if the total symptom score is reduced by at least 18% compared to a baseline total symptom score. In some embodiments, a total symptom score is reduced if the total symptom score is reduced by at least 20% compared to a baseline total symptom score. In some embodiments, a total symptom score is reduced if the total symptom score is reduced by at least 30% compared to a baseline total symptom score. In some embodiments, a total symptom score is reduced if the total symptom score is reduced by at least 40% compared to a baseline total symptom score. In some embodiments, a total symptom score is reduced if the total symptom score is reduced by at least at least 50% compared to a baseline total symptom score. In some embodiments, a total symptom score is reduced if the total symptom score is reduced by at least 60% compared to a baseline total symptom score. In some embodiments, a total symptom score is reduced if the total symptom score is reduced by at least 70% compared to a baseline total symptom score. In some embodiments, a total symptom score is reduced if the total symptom score is reduced by at least 75% compared to a baseline total symptom score. In some embodiments, a total symptom score is reduced if the total symptom score is reduced by at least 80% compared to a baseline total symptom score. In some embodiments, a total symptom score is reduced if the total symptom score is reduced by at least at least 90% compared to a baseline total symptom score. In some embodiments, the baseline total symptom score is the total symptom score before administering a BTK inhibitor as described herein. In some embodiments, the total symptom score refers to an average of daily total symptom score, such as a 7-day average of daily total symptom score, a 10-day average of daily total symptom score, a 14-day average of daily total symptom score, or a 21-day average of daily total symptom score. In some embodiments, the total symptom score refers to an average of daily total symptom score, such as a 7-day rolling average of daily total symptom score, a 10-day rolling average of daily total symptom score, a 14-day rolling average of daily total symptom score, or a 21-day rolling average of daily total symptom score. In some embodiments, a reduction in a symptom and/or in a total symptom score is obtained after administering a BTK inhibitor as described herein for a period of time of at least 8 weeks, such as at least 12 weeks, at least 16 weeks, at least 20 weeks, at least 24 weeks, and/or at least 30 weeks. In some embodiments, a reduction in a symptom and/or in a total symptom score is obtained after administering a BTK inhibitor as described herein for a period of time of at least 8 weeks, such as a period of 8 weeks. In some embodiments, a reduction in a symptom and/or in a total symptom score is obtained after administering a BTK inhibitor as described herein for a period of time of at least 12 weeks, such as a period of 12 weeks. In some embodiments, a reduction in a symptom and/or in a total symptom score is obtained after administering a BTK inhibitor as described herein for a period of time of at least 16 weeks, such as a period of 16 weeks. In some embodiments, a reduction in a symptom and/or in a total symptom score is obtained after administering a BTK inhibitor as described herein for a period of time of at least 20 weeks, such as a period of 20 weeks. In some embodiments, a reduction in a symptom and/or in a total symptom score is obtained after administering a BTK inhibitor as described herein for a period of time of at least 24 weeks, such as a period of 24 weeks. In some embodiments, a reduction in a symptom and/or in a total symptom score is obtained after administering a BTK inhibitor as described herein for a period of time of at least 30 weeks, such as a period of 30 weeks.

Pharmaceutical Compositions

In some embodiments, the disclosure provides pharmaceutical compositions comprising a BTK inhibitor compound selected from Table 1 or a pharmaceutically acceptable salt thereof for treating ISM. In some embodiments, the disclosure provides pharmaceutical compositions comprising a BTK inhibitor compound selected from Table 1 or a pharmaceutically acceptable salt thereof reducing or alleviating a symptom selected from fatigue, abdominal pain, diarrhea, nausea, skin spots, itching, flushing, brain fog, headache, dizziness, bone pain, or a combination thereof in a human subject with ISM. In some embodiments, the disclosure provides pharmaceutical compositions comprising a BTK inhibitor compound selected from Table 1 or a pharmaceutically acceptable salt thereof reducing or alleviating a symptom selected from muscle pain, difficulty concentrating, runny nose, nasal congestion, wheezing, shortness of breath, throat itching, heart palpitations, diarrhea, or a combination thereof in a human subject with ISM. In some embodiments, the disclosure provides pharmaceutical compositions comprising a BTK inhibitor compound selected from Table 1 or a pharmaceutically acceptable salt thereof reducing or alleviating a symptom selected from itching, skin redness and/or swelling, flushing, diarrhea and/or loose stools, fatigue and/or exhaustion, headache, muscle and/or joint pain, difficulty concentrating, or a combination thereof in a human subject with ISM.

The pharmaceutical compositions are typically formulated to provide a therapeutically effective amount of a BTK inhibitor compound selected from Table 1 or a pharmaceutically acceptable salt thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants. Where desired, other ingredients in addition to the BTK inhibitor or a pharmaceutically acceptable salt thereof may be mixed into a preparation or both components may be formulated into separate preparations for use in combination separately or at the same time.

In selected embodiments, the concentration of the BTK inhibitor or a pharmaceutically acceptable salt thereof provided in the pharmaceutical compositions of the disclosure is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v.

In selected embodiments, the concentration of the BTK inhibitor or a pharmaceutically acceptable salt thereof provided in the pharmaceutical compositions of the disclosure is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v.

In selected embodiments, the concentration of the BTK inhibitor or a pharmaceutically acceptable salt thereof is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v.

In selected embodiments, the concentration of the BTK inhibitor or a pharmaceutically acceptable salt thereof is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In selected embodiments, the amount of the BTK inhibitor or a pharmaceutically acceptable salt thereof is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of the BTK inhibitor or a pharmaceutically acceptable salt thereof is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g or 10 g.

The BTK inhibitor compounds in Table 1 and pharmaceutically acceptable salts thereof are effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting exemplary pharmaceutical compositions and methods for preparing the same.

Pharmaceutical Compositions for Oral Administration

In selected embodiments, the disclosure provides a pharmaceutical composition for oral administration comprising a BTK inhibitor compound selected from Table 1 or a pharmaceutically acceptable salt thereof, and a pharmaceutical excipient suitable for oral administration.

In selected embodiments, the disclosure provides a solid pharmaceutical composition for oral administration containing: (i) an effective amount of the BTK inhibitor or a pharmaceutically acceptable salt thereof, in combination and (ii) a pharmaceutical excipient suitable for oral administration. In selected embodiments, the composition further contains (iii) an effective amount of at least one additional active ingredient.

In selected embodiments, the pharmaceutical composition may be a liquid pharmaceutical composition suitable for oral consumption. Pharmaceutical compositions of the disclosure suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The disclosure further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The BTK inhibitor or a pharmaceutically acceptable salt thereof can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the disclosure to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present disclosure and to minimize precipitation of the compound of the present disclosure. This can be especially important for compositions for non-oral use, such as for compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Examples may include, but are not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the disclosure provides a pharmaceutical composition for injection comprising a BTK inhibitor compound selected from Table 1 or a pharmaceutically acceptable salt thereof, and a pharmaceutical excipient suitable for injection. Components and amounts of agents in the compositions are as described herein.

The forms in which the compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating the BTK inhibitor or a pharmaceutically acceptable salt thereof in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of the BTK inhibitor or a pharmaceutically acceptable salt thereof or pharmaceutical composition of these compounds can be effected by any method that enables delivery of the compounds to the site of action. These methods include oral routes, intraduodenal routes, parenteral injection (including intravenous, intra-arterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The disclosure also provides kits. The kits include a BTK inhibitor compound selected from Table 1 or a pharmaceutically acceptable salt thereof, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In an embodiment, the disclosure provides a kit comprising the BTK inhibitor or a pharmaceutically acceptable salt thereof for use in the treatment of ISM as described herein. In an embodiment, the disclosure provides a kit comprising the BTK inhibitor or a pharmaceutically acceptable salt thereof salt thereof for use in reducing or alleviating a symptom of ISM such as fatigue, abdominal pain, diarrhea, nausea, skin spots, itching, flushing, brain fog, headache, dizziness, bone pain, or a combination thereof as described herein. In an embodiment, the disclosure provides a kit comprising the BTK inhibitor or a pharmaceutically acceptable salt thereof salt thereof for use in reducing or alleviating a symptom of ISM such as muscle pain, difficulty concentrating, runny nose, nasal congestion, wheezing, shortness of breath, throat itching, heart palpitations, diarrhea, or a combination thereof as described herein. In an embodiment, the disclosure provides a kit comprising the BTK inhibitor or a pharmaceutically acceptable salt thereof salt thereof for use in reducing or alleviating a symptom of ISM such as itching, skin redness and/or swelling, flushing, diarrhea and/or loose stools, fatigue and/or exhaustion, headache, muscle and/or joint pain, difficulty concentrating, or a combination thereof as described herein.

Dosages and Dosing Regimens

The amount of a BTK inhibitor or a pharmaceutically acceptable salt thereof administered will be dependent on the human subject being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In some embodiments, a BTK inhibitor or a pharmaceutically acceptable salt thereof is administered in a single dose. Multiple daily doses are also embodied, for example, twice daily. Typically, such administration will be oral. However, other routes may be used as appropriate.

In some embodiments, a BTK inhibitor or a pharmaceutically acceptable salt thereof is administered in multiple doses for treating ISM. In some embodiments, a BTK inhibitor or a pharmaceutically acceptable salt thereof is administered in multiple doses for reducing or alleviating a symptom associated with ISM selected from fatigue, abdominal pain, diarrhea, nausea, skin spots, itching, flushing, brain fog, headache, dizziness, bone pain, or a combination thereof. In some embodiments, a BTK inhibitor or a pharmaceutically acceptable salt thereof is administered in multiple doses for reducing or alleviating a symptom associated with ISM selected from muscle pain, difficulty concentrating, runny nose, nasal congestion, wheezing, shortness of breath, throat itching, heart palpitations, diarrhea, or a combination thereof. In some embodiments, a BTK inhibitor or a pharmaceutically acceptable salt thereof is administered in multiple doses for reducing or alleviating a symptom associated with ISM selected from itching, skin redness and/or swelling, flushing, diarrhea and/or loose stools, fatigue and/or exhaustion, headache, muscle and/or joint pain, difficulty concentrating, or a combination thereof.

In an embodiment, a BTK inhibitor or a pharmaceutically acceptable salt thereof is administered in multiple doses. In an embodiment, dosing may be once, twice, three times, or four times per day. In an embodiment, dosing may be selected from the group consisting of once a day, twice a day, three times a day, or four times a day, once every other day, once weekly, twice weekly, three times weekly, four times weekly, biweekly, and monthly. In other embodiments, a BTK inhibitor or a pharmaceutically acceptable salt thereof is administered about once per day to about four times per day. In some embodiments a BTK inhibitor or a pharmaceutically acceptable salt thereof is administered once daily, while in other embodiments a BTK inhibitor or a pharmaceutically acceptable salt thereof is administered twice daily, and in other embodiments a BTK inhibitor or a pharmaceutically acceptable salt thereof is administered three times daily. In some embodiments a BTK inhibitor or a pharmaceutically acceptable salt thereof is administered three times a week, including every Monday, Wednesday, and Friday.

Administration of a BTK inhibitor or a pharmaceutically acceptable salts thereof may continue as long as necessary. In some embodiments, a BTK inhibitor or a pharmaceutically acceptable salt thereof is administered for more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. In some embodiments, a BTK inhibitor or a pharmaceutically acceptable salt thereof is administered for less than 28, 14, 7, 6, 5, 4, 3, 2, or 1 day. In some embodiments, a BTK inhibitor or a pharmaceutically acceptable salt thereof is administered for about 14 days, about 21 days, about 28 days, about 35 days, about 42 days, about 49 days, or about 56 days. In some embodiments, a BTK inhibitor or a pharmaceutically acceptable salt thereof is administered chronically on an ongoing basis—e.g., for the reducing or alleviating of chronic effects. In another embodiment the administration of a BTK inhibitor or a pharmaceutically acceptable salt thereof continues for less than about 7 days. In yet another embodiment the administration continues for more than about 6, 10, 14, 28 days, two months, three months, four months, five months, six months, seven months, eight months, nine months, ten months, eleven months or one year. In some embodiments, the administration continues for more than about one year, two years, three years, four years, or five years. In some embodiments, continuous dosing is achieved and maintained as long as necessary.

In some embodiments, an effective dosage of a BTK inhibitor or a pharmaceutically acceptable salt thereof is in the range of about 1 mg to about 600 mg, about 10 mg to about 500 mg, about 20 mg to about 450 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a BTK inhibitor or a pharmaceutically acceptable salt thereof is about 15 mg, about 25 mg, about 30 mg, about 50 mg, about 50 mg, about 75 mg, about 90 mg, about 100 mg, about 120 mg, about 125 mg, about 150 mg, about 175 mg, about 180 mg, about 200 mg, about 225 mg, about 240 mg, about 250 mg, about 275 mg, about 300 mg, about 325 mg, about 350 mg, about 360 mg, about 375 mg, about 400 mg, about 425 mg, about 450 mg, about 475 mg, about 480 mg, or about 500 mg. In some embodiments, an effective dosage of a BTK inhibitor or a pharmaceutically acceptable salt thereof is 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

In some embodiments, an effective dosage of a BTK inhibitor or a pharmaceutically acceptable salt thereof is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a BTK inhibitor or a pharmaceutically acceptable salt thereof is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a BTK inhibitor or a pharmaceutically acceptable salt thereof is administered at a dosage of 10 to 500 mg BID, including a dosage of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg BID.

In some embodiments, a BTK inhibitor or a pharmaceutically acceptable salt thereof is administered at a dosage of 10 to 600 mg QD, including a dosage of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg QD.

An effective amount of a BTK inhibitor or a pharmaceutically acceptable salt thereof may be administered in either single or multiple doses by any of the accepted modes of administration of agents having similar utilities, including buccal, sublingual, and transdermal routes, by intra-arterial injection, intravenously, parenterally, intramuscularly, subcutaneously or orally.

In some embodiments, a BTK inhibitor or a pharmaceutically acceptable salt thereof is administered to a subject intermittently, known as intermittent administration. By "intermittent administration" it is meant a period of administration of a therapeutically effective dose of a BTK inhibitor or a pharmaceutically acceptable salt thereof, followed by a time period of discontinuance, which is then followed by another administration period and so on. In each administration period, the dosing frequency can be independently selected from three times daily, twice daily, daily, once weekly, twice weekly, three times weekly, four times weekly, five times weekly, six times weekly or monthly. In an embodiment, the BTK inhibitor is a compound selected from Table 1 or a pharmaceutically acceptable salt thereof.

By "period of discontinuance" or "discontinuance period" or "rest period", it is meant to the length of time when discontinuing of the administration of a BTK inhibitor or a pharmaceutically acceptable salt thereof. The time period of discontinuance may be longer or shorter than the administration period or the same as the administration period. During the discontinuance period, other therapeutic agents other than a BTK inhibitor or a pharmaceutically acceptable salt thereof may be administered. The discontinuance period may be necessary to alleviate any toxic effects associated with a particular BTK inhibitor compound.

In an embodiment, a BTK inhibitor or a pharmaceutically acceptable salt thereof is administered to a human subject in need thereof for treating ISM and/or for reducing or alleviating a symptom of ISM for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, eleven weeks, three months, thirteen weeks, fourteen weeks, fifteen weeks, four months, and more days, in which a BTK inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject weekly; and the discontinuance period is about two weeks. In an embodiment, the first administration period and the second administration period are about four weeks, in which a BTK inhibitor or a pharmaceutically acceptable salt thereof is administered to a subject daily; and the discontinuance period is about two weeks. In an embodiment, the first administration period and the second administration period are about four weeks, in which a BTK inhibitor or a pharmaceutically acceptable salt thereof is administered to a subject weekly; and the discontinuance period is about two weeks. In an embodiment, the BTK inhibitor is a compound selected from Table 1 or a pharmaceutically acceptable salt thereof.

In an embodiment, a BTK inhibitor or a pharmaceutically acceptable salt thereof is administered to a subject in need thereof for treating ISM and/or for reducing or alleviating a symptom of ISM for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the BTK inhibitor is selected from any of the compounds in Table 1 or a pharmaceutically acceptable salt thereof. In an embodiment, the BTK inhibitor is orally administered at a dose of 100 mg twice a day.

Reduction of Mast Cell Activation

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the percentage of activated mast cells and/or basophils is reduced after administration of the BTK inhibitor.

In some embodiments, the percentage of activated mast cells and/or basophils in a human subject treated with a BTK inhibitor is reduced compared to the percentage of activated mast cells, and/or basophils in the human subject prior to the treatment. In some embodiments, the activated mast cells are assessed by the basophil activation tests (BAT) described in Example 1. In some embodiments, basophil activation is an indirect measure of mast cell activation. In some embodiments, basophil activation is a proxy for mast cell activation. In some embodiments, basophils can provide insights into hypersensitivity of mast cells without directly accessing mast cells.

In some embodiments, the percentage of activated mast cells and/or basophils after treatment is about 95%, about 90%, about 85%, about 75%, about 70%, about 65%, about 60%, about 55%, about 50%, about 45%, about 40%, about 35%, about 30%, about 25%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or about 1% of the mast cell and/or basophil population. The percentage of activated mast cells and/or basophils after treatment is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the mast cell and/or basophil population prior to the treatment. In some embodiments, the percentage of activated mast cells and/or basophils is assessed and calculated by a sample derived from a blood sample of the human subject. In some embodiments, the sample is or is derived from a tissue biopsy.

Mast cell and/or basophil activation can be determined by any appropriate method. Flow cytometry techniques can detect molecular cell surface markers associated with activated mast cells and/or basophils. The number of activated mast cells and/or basophils in the sample can be determined and a percentage of activated mast cells and/or basophils can be calculated. Mast cell and/or basophil activation can be determined by fluorescence activated cell sorting (FACS) techniques. In some embodiments, the activation cell marker is CD63. In some embodiments, the activation marker is CD203. Mast cell and/or basophil activation can be determined by appropriate ELISA assays, which detect expression of cell surface proteins associated with mast cell and/or basophil activation.

Reduction of $Ca^{2+}$ Release and Influx

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the concentration of cytosolic $Ca^{2+}$ in cells in the human subject after treatment is reduced compared to the concentration of cytosolic $Ca^{2+}$ in cells in the human subject prior to the treatment. In some embodiments, the cells comprise mast cells. In some embodiments, the cells comprise basophils.

In some embodiments, the concentration of cytosolic $Ca^{2+}$ in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the concentration of cytosolic $Ca^{2+}$ in untreated cells. In some embodiments, the treated cells and the untreated cells are mast cells of the human subject. In some embodiments, the treated cells and the untreated cells are basophils of the human subject.

Cytosolic $Ca^{2+}$ concentration in cells can be determined by any appropriate method including, but not limited to, multiphoton fluorescence imaging (MFI), flow cytometry, live cell imaging, and/or the use of $Ca^{2+}$ binding dyes. The binding dyes, which bind intracellular calcium in a quantifiable manner, may exhibit an increase in fluorescence intensity or a shift in emission wavelength upon calcium binding.

Reduction of Cytokine Release

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount of cytokine expressed and/or released from cells treated with the BTK inhibitor is reduced compared to the amount of cytokine expressed and/or released from cells untreated with the BTK inhibitor. In some embodiments, the untreated cells are part of a sample before treatment with a BTK inhibitor, and the treated cells are part of the sample after treatment with a BTK inhibitor. In some embodiments, the cells comprise mast cells. In some embodiments, the cells comprise basophils. In some embodiments, the cytokine release is IgE-induced.

In some embodiments, the amount of cytokine released by the cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of cytokine released by untreated cells.

Cytokine release can be determined by any appropriate method including, but not limited to, Cytometric Bead Array and/or ELISA, which can be used to detect protein expression associated with cytokine release. In some embodiments, the cytokine is IL-8, MCP-1, MIP-1a, IL-10, IL-13, or a combination thereof.

Reduction of Histamine Release

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount of histamine released from mast cells and/or basophils treated with the BTK inhibitor is reduced compared to the amount of histamine release from mast cells and/or basophils untreated with the BTK inhibitor. In some embodiments, the untreated mast cells and/or basophils are part of a sample before treatment with the BTK inhibitor, and the treated mast cells and/or basophils are part of the sample after treatment with the BTK inhibitor. In some embodiments, the histamine release is IgE-induced.

In some embodiments, the amount of histamine released by the mast cells and/or basophils treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount of histamine released by untreated mast cells and/or basophils.

Histamine release can be determined by any appropriate method including, but not limited to ELISA or fluorometric assays, which detects protein expression associated with histamine release.

Reduction of BTK Phosphorylation

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-BTK (pBTK) in cells treated with the BTK inhibitor is reduced compared to the amount or concentration of pBTK in cells untreated with the BTK inhibitor. In some embodiments, the phosphorylation site is residue Y223 of BTK. In some embodiments, the phosphorylation of BTK is induced by IgE. In some embodiments, the cells comprise mast cells. In some embodiments, the cells comprise basophils.

In some embodiments, the amount or concentration of pBTK in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pBTK in untreated cells.

The amount or concentration of pBTK can be determined by any appropriate method including, but not limited to, multi-parameter phospho-flow cytometry or Western Blot analysis Reduction of Phospho-Phospholipase C Gamma (PLC γ)

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-PLCγ (pPLCγ) in cells treated with the BTK inhibitor is reduced compared to the amount or concentration of pPLCγ in cells untreated with the BTK inhibitor. In some embodiments, the phosphorylation cite is residue S1248 of PLCγ1. In some embodiments, the phosphorylation site is residue Y1217 of the PLCγ2. In some embodiments, the phosphorylation of PLCγ is induced by IgE. In some embodiments, the cells comprise mast cells. In some embodiments, the cells comprise basophils.

In some embodiments, the amount or concentration of pPLCγ in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pPLCγ in untreated cells.

The amount or concentration of pPLCγ can be determined by any appropriate method including, but not limited to, multi-parameter phospho-flow cytometry or Western Blot analysis.

Reduction of Phospho-Protein Kinase C (PKC)

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-PKC (pPKC) in cells treated with the BTK inhibitor is reduced compared to the amount or concentration of pPKC in cells untreated with the BTK inhibitor. In some embodiments, the phosphorylation site is residue S643/676 of the PKC. In some embodiments, the phosphorylation of PKC is induced by IgE. In some embodiments, the cells comprise mast cells. In some embodiments, the cells comprise basophils.

In some embodiments, the amount or concentration of pPKC in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pPKC in untreated cells.

The amount of pPKC can be determined by any appropriate method including, but not limited to, multi-parameter phospho-flow cytometry or Western Blot analysis.

Reduction of Phospho-AKT (pAKT)

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-AKT (pAKT) in cells treated with the BTK inhibitor is reduced compared to the amount or concentration of pAKT in cells untreated with the BTK inhibitor. In some embodiments, the phosphorylation site is residue S473 of the AKT. In some embodiments, the phosphorylation of AKT is induced by IgE. In some embodiments, the cells comprise mast cells. In some embodiments, the cells comprise basophils.

In some embodiments, the amount or concentration of pAKT in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pAKT in untreated cells.

The amount or concentration of pAKT can be determined by any appropriate method including, but not limited to, multi-parameter phospho-flow cytometry or Western Blot analysis.

Reduction of Phospho-S6 (pS6)

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-S6 (pS6) in cells treated with the BTK inhibitor is reduced compared to the amount or concentration of pBTK in cells untreated with the BTK inhibitor. In some embodiments, the untreated cells are part of a sample before treatment with the BTK inhibitor, and the treated cells are part of the sample after treatment with the BTK inhibitor. In some embodiments, the phosphorylation site is residue S235/236 of the S6. In some embodiments, the phosphorylation of S6 is induced by IgE. In some embodiments, the cells comprise mast cells. In some embodiments, the cells comprise basophils.

In some embodiments, the amount or concentration of pS6 in cells treated with the BTK inhibitor reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pS6 in untreated cells.

The amount or concentration of pS6 can be determined by any appropriate method including, but not limited to, multi-parameter phospho-flow cytometry or Western Blot analysis, which detect the amount of a protein expressed in cells.

Reduction of Phospho-P38 (pP38)

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-P38 (pP38) in cells treated with the BTK inhibitor is reduced compared to the amount or concentration of pBTK in cells untreated with the BTK inhibitor. In some embodiments, the untreated cells are part of a sample before treatment with the BTK inhibitor, and the treated cells are part of the sample after treatment with the BTK inhibitor. In some embodiments, the phosphorylation site is residue T180/Y182 of the P38. In some embodiments, the phosphorylation of P38 is induced by IgE. In some embodiments, the cells comprise mast cells. In some embodiments, the cells comprise basophils.

In some embodiments, the amount or concentration of pP38 in cells in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pP38 in untreated cells.

The amount or concentration of pP38 can be determined by any appropriate method including, but not limited to, multi-parameter phospho-flow cytometry or Western Blot analysis.

Reduction of Phosphor-ERK (pERK)

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount or concentration of phospho-ERK (pERK) in cells treated with the BTK inhibitor is reduced compared to the amount or concentration of pBTK in cells untreated with the BTK inhibitor. In some embodiments, the phosphorylation site is residue T202/Y204 of ERK. In some embodiments, the phosphorylation of ERK is induced by IgE. In some embodiments, the cells comprise mast cells. In some embodiments, the cells comprise basophils.

In some embodiments, the amount or concentration of pERK in cells in cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount or concentration of pERK in untreated cells.

The amount or concentration of pERK can be determined by any appropriate method including, but not limited to, multi-parameter phospho-flow cytometry or Western Blot analysis.

Reduction of Cell Surface Expression of CD63

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount of CD63 expressed on the surface of cells treated with the BTK inhibitor is reduced compared to the amount of CD63 expressed on the surface of cells untreated with the BTK inhibitor. In some embodiments, the cells comprise mast cells. In some embodiments, the cells comprise basophils. In some embodiments, the cell surface expression of CD63 is induced by IgE.

In some embodiments, the amount of CD63 expressed on the surface of cells treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount of CD63 expressed on the surface of untreated cells.

The amount of surface-expressed CD63 can be determined by any appropriate method including, but not limited to, Western Blot analysis that detects protein expression, flow cytometry techniques that detect labeled cell surface proteins (Wang et al., Flow cytometric quantification of CD63 in exosomes derived from human serum, *Analytical Biochemistry*, 2018, 553, 78-85; Gyimesi et al., Basophil CD63 expression assay on highly sensitized atopic donor leucocytes—a useful method in chronic autoimmune urticaria, *British Journal of Dermatology*, 2004, 151(2), 388-396; Ebo et al., Basophil activation test by flow cytometry: Present and future applications in allergology, Cytometry Part B 2008; 74B: 201-210), ELISA techniques that detect extracellular vesicles (Li et al., Progress in exosome isolation techniques and their applications to clinical studies. *Theranostics*, 2017, 7(3), 789-804), Quantitative Polymerase Chain Reaction (qPCR) techniques that detect CD63 mRNA expression levels; or fluorescence activated cell sorting (FACS) techniques that detects labeled cell surface proteins. In some embodiments, the CD63 expression is detected using an anti-CD63 antibody. In some embodiments, the anti-CD63 antibody is selected from the group consisting of: anti-CD63 Chemicon (Milipore); RFAC4 (e.g. Millipore); anti-CD63 AHN16.1/46-4-5 (e.g. Santa Cruz); anti-CD63 3H1626 (e.g. Santa Cruz); anti-CD63 LP9 (e.g. Santa Cruz); anti-CD63 BEM-1 (e.g. Santa Cruz); and anti-CD63 460305 (e.g. R&D Systems); anti-CD63 Santa Cruz A H 16.1/46-4-5 (e.g. Santa Cruz); anti-CD63 Santa Cruz 3H 1626 (e.g. Santa Cruz); anti-CD63 R & D systems 460305 (e.g. R&D Systems); and combinations thereof. In some embodiments, the anti-CD63 antibody is a monoclonal antibody. In some embodiments, the anti-CD63 antibody is a polyclonal antibody. In some embodiments, the anti-CD63 antibody is a murine anti-CD63 antibody (Clone H5C6, Clone TEA3/18, or Clone MEM-259), rabbit anti-CD63 antibody, a rat anti-CD63 antibody (Clone NVG-2), or human anti-CD63 recombinant antibody.

Reduction of Cell Surface Expression of CD203

In some embodiments, the invention encompasses a method of treating indolent systemic mastocytosis (ISM) in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof. In some embodiments, the amount of CD203 expressed on the surface of cells treated with the BTK inhibitor is reduced compared to the amount of CD203 expressed on the surface of cells untreated with the BTK inhibitor. In some embodiments, the cells comprise mast cells. In some embodiments, the cells comprise basophils. In some embodiments, the cell surface expression of CD203 is induced by IgE.

In some embodiments, the amount of CD203 expressed treated with the BTK inhibitor is reduced by about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1%, or less than about 1% of the amount of CD203 expressed on the surface of untreated cells.

The amount of surface-expressed CD203 can be determined by any appropriate method including, but not limited to, Western Blot analysis, flow cytometry techniques that detect labeled cell surface proteins (Ebo et al., Basophil activation test by flow cytometry: Present and future applications in allergology. *Cytometry Part B* 2008; 74B: 201-210), ELISA techniques that detect extracellular vesicles (Li et al., Progress in exosome isolation techniques and their applications to clinical studies. *Theranostics*, 2017, 7(3), 789-804), Quantitative Polymerase Chain Reaction (qPCR) techniques that detect CD203 mRNA expression levels; or fluorescence activated cell sorting (FACS) techniques that detects labeled cell surface proteins.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Basophil Activation Test (BAT)

Figures 2A, 2B:
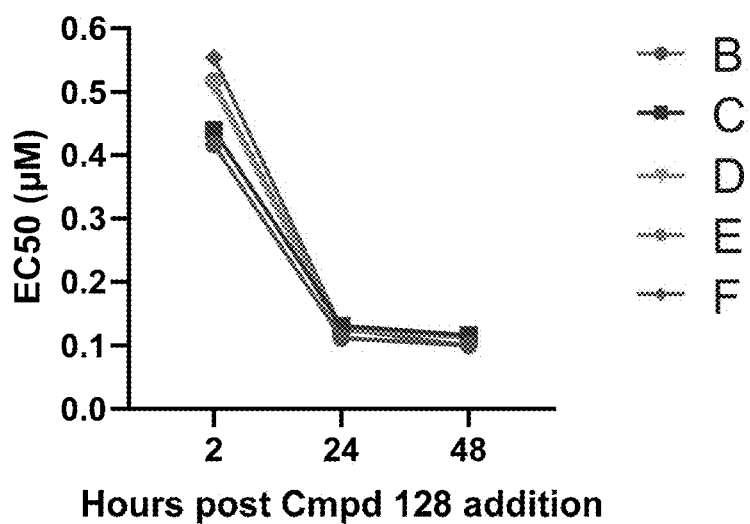
FIG. 2A is a summary graph showing potency of basophil activation inhibition over different incubation times after BTK inhibitor (Compound 128) addition.
FIG. 2B shows $EC_{50}$ and $EC_{90}$ over time after BTK inhibitor (Compound 128) addition.

The BAT was conducted as set forth in Santos (2021) Allergy, 76:2420-2432. Blood from six healthy donors was drawn and Compound 128 was added at various concentrations (10 µM, 3.16 µM, 1 µM, 0.3 µM, 0.1 µM, 0.03 µM, or 0 µM). Blood samples were gently rocked at room temperature for 2 hours, 24 hours, or 48 hours. The BAT assay using the Flow Cast Basophil Activation Kit (Buhlmann Diagnostics; Catalog # B—CCR-STCON) was then conducted following manufacturer instructions by (1) stimulating the blood with anti-FcεR stimulation control in stimulation buffer with IL-3 and staining cells for CCR3 and CD63 for 15 minutes at 37° C., (2) lysing red blood cells and fixing cells with Lysing Reagent at room temperature for 10 minutes, (3) washing cells with Wash Buffer, and (4) acquiring data on a flow cytometer. Activated basophils were defined as CCR3+, low side scatter and CD63+. Percent of activated basophils was calculated as number of activated basophils over the total number of basophils. A four-parameter logistic regression was applied to determine the $EC_{50}$ and $EC_{90}$. FIG. 1 shows the percent of activated basophils (CD63+). The results demonstrated that Compound 128 more potently inhibits basophil activation after longer drug exposures. FIG. 2 shows the potency of basophil activation inhibition over time after Compound 128 addition. The results demonstrated that Compound 128 inhibits anti-FcεR induced basophil activation and Compound 128 potency increased approximately 4-fold after 24 hours drug exposure. The average $EC_{50}$ calculated for Compound 128 after a 2-hour, 24-hour and 48-hour drug exposure was 0.5, 0.12 and 0.1 µM, respectively.

Example 2: Phospho-BTK (pBTK) Test

Figure 3:
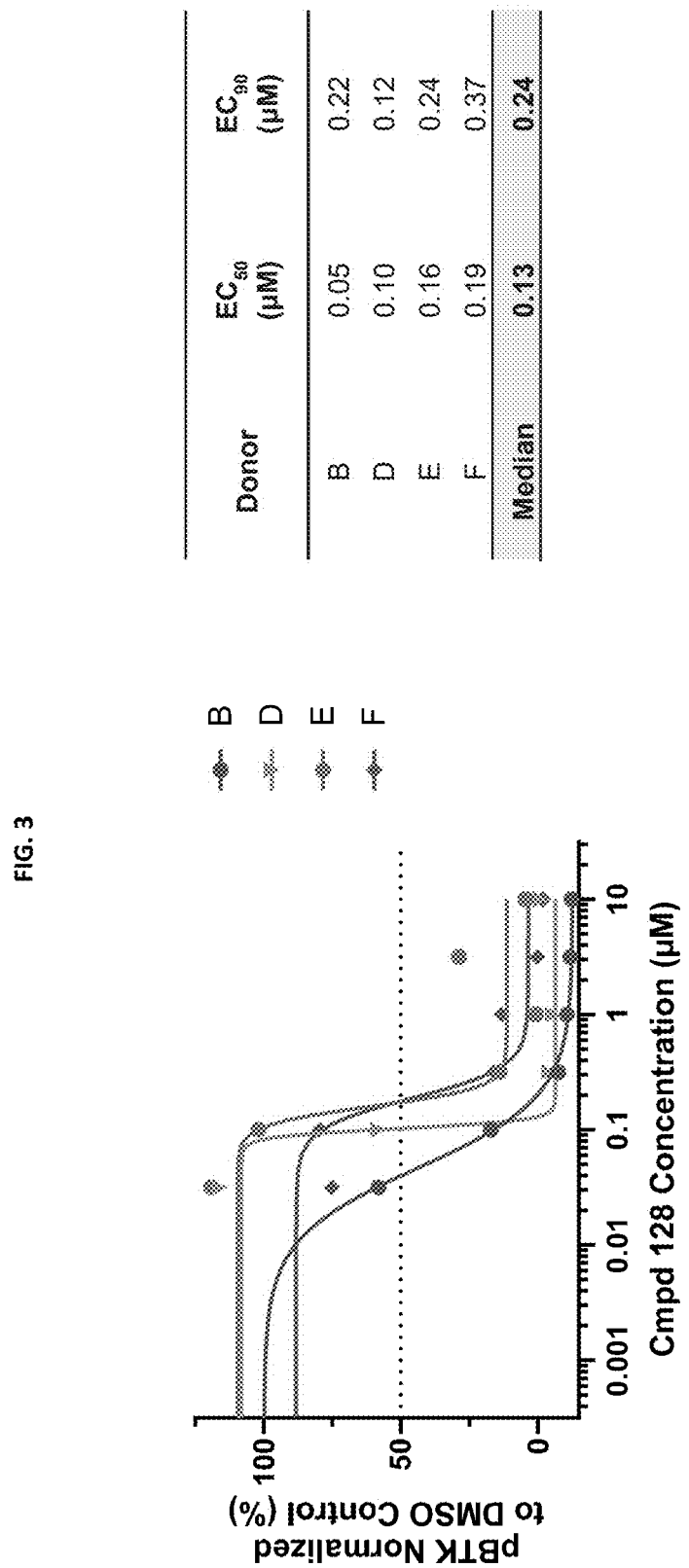
FIG. 3 is a graph showing percent of phosphorylated BTK (pBTK) normalized to DMSO (vehicle) control in basophils, after exposure to different BTK inhibitor (Compound 128) concentrations for 24 hours.
Figure 4:
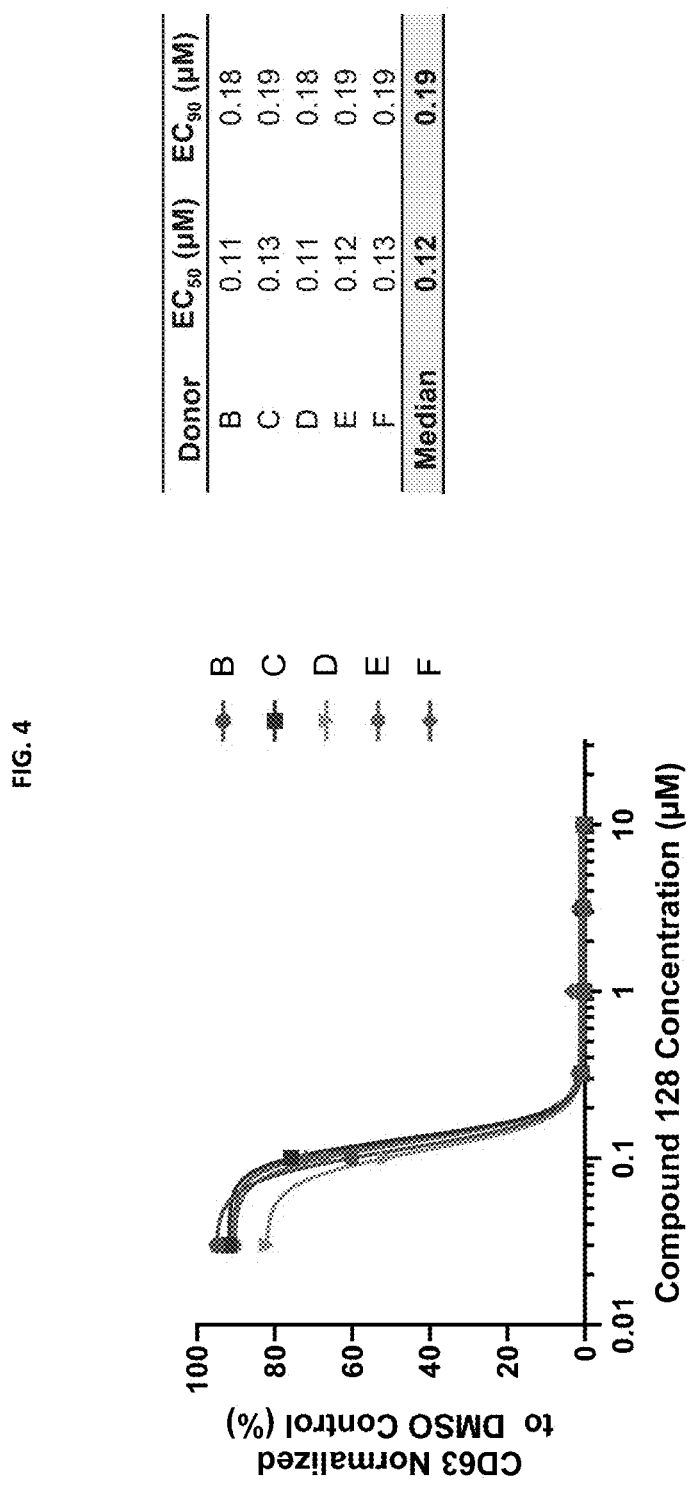
FIG. 4 is a graph showing percent of activated basophils (CD63+) normalized to DMSO (vehicle) control in basophils, after exposure to different BTK inhibitor (Compound 128) concentrations for 24 hours.

Blood from four healthy donors was drawn and Compound 128 was added at various concentrations (10 µM, 3.16 µM, 1 µM, 0.3 µM, 0.1 µM, 0.03 µM, or 0 µM). Blood samples were gently rocked at room temperature for 24 hours. The pBTK test was then conducted by (1) stimulating the blood with anti-FcεR stimulation control from Flow Cast Basophil Activation Kit and staining cells for CCR3 (Becton Dickinson) and a near-IR dead cell stain (nIR; Invitrogen) for 15 minutes at 37° C., (2) lysing red blood cells and fixing cells with Phosflow Lyse/Fix Buffer (Becton Dickinson) at 37° C. for 10 minutes, (3) washing once with 1× phosphate-buffered saline (PBS), (4) washing twice with Perm/Wash buffer (Becton Dickinson), (5) permeabilizing cells with Perm/Wash buffer on ice for 15 minutes, (6) staining cells for rabbit anti-human pBTK (Abcam) for 30 minutes on ice, (7) washing twice with Perm/Wash buffer, (8) staining with goat anti-rabbit secondary antibody (Invitrogen) for 30 minutes on ice, (9) washing twice with Perm/Wash buffer, and (10) acquiring data on a flow cytometer. Live basophils were defined as nIR−, CCR3+ and low side scatter. The median fluorescence intensity of phosphorylated BTK was measured and percent of stimulated control was calculated. A four-parameter logistic regression was applied to determine the $EC_{50}$ and $EC_{90}$. FIG. 3 shows the percent of pBTK (Y223) normalized to DMSO control for all four donors gated on CCR3+ basophils. The average $EC_{50}$ (n=4) calculated for Compound 128 was 0.13 µM. FIG. 4 shows the percent of CD63 normalized to DMSO control for donor B gated on CCR3+ basophils that was measured according to BAT assay method in Example 1. The percent of stimulated control of activated mast cells (CD63+) was calculated. A four-parameter logistic regression was applied to determine the $EC_{50}$ and $EC_{90}$. The average $EC_{50}$ (n=4) calculated for Compound 128 was 0.12 µM. The results demonstrated that Compound 128 inhibits anti-FcεR induced pBTK and basophil activation.

Example 3: Comparison of BTK Inhibitors by BAT

Figure 5A:
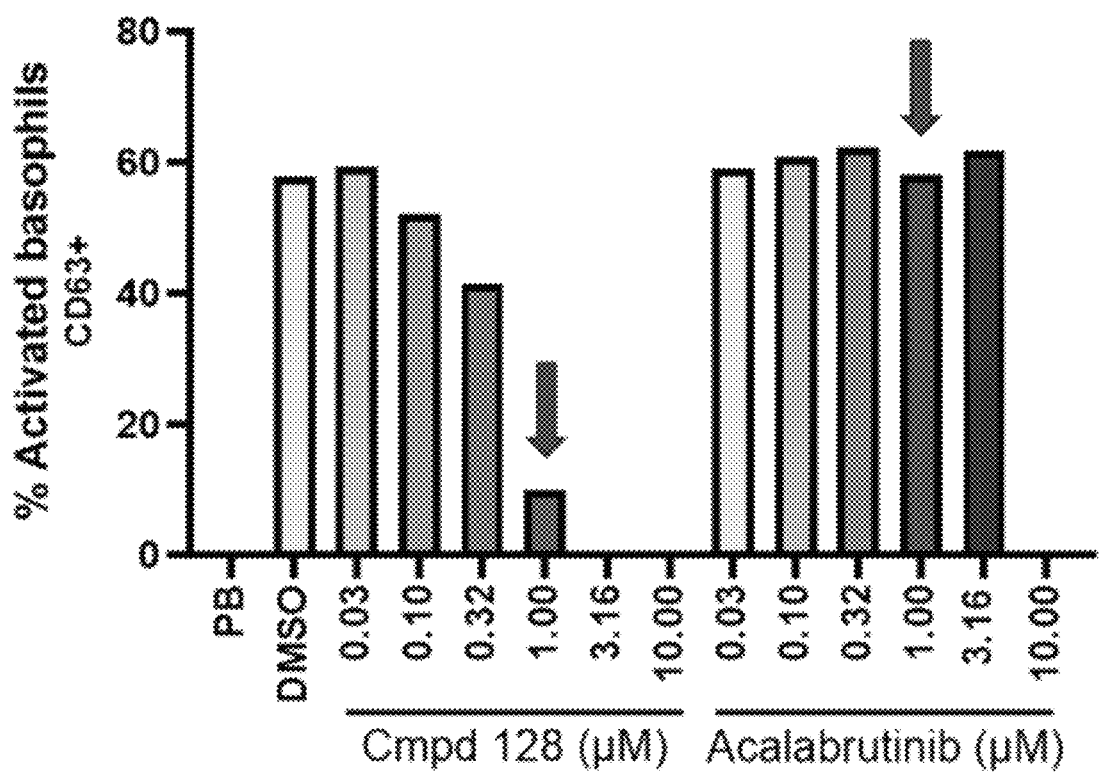
FIG. 5A is a graph showing percent of activated basophils (CD63+) after exposure to different BTK inhibitors (compound 128 or Acalabrutinib) at different concentrations using stimulation control with IL-3.
Figure 5B:
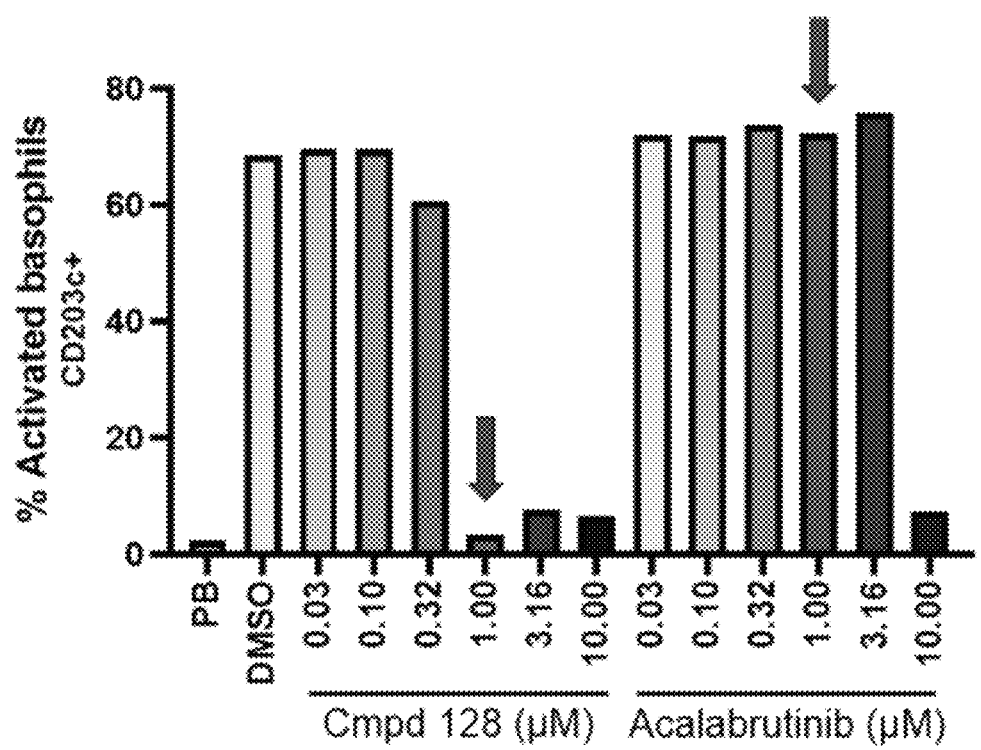
FIG. 5B is a graph showing percent of activated basophils (CD203c+) after exposure to different BTK inhibitors at different concentrations using stimulation control without IL-3.

Blood from a healthy donor was drawn and Compound 128 or acalabrutinib was added at various concentrations (10 µM, 3.16 µM, 1 µM, 0.3 µM, 0.1 µM, 0.03 µM, or 0 µM). Blood samples were gently rocked at room temperature for 2 hours. The BAT assay measuring CD63 used the Flow Cast Basophil Activation Kit method and percent activated basophils was calculated as described in Example 1. The BAT assay measuring CD203c using the Flow Cast Basophil Activation Kit and CD203c Reagent Set (Buhlmann Diagnostics; Catalog # B-CCR-203SET) was then conducted by (1) stimulating the blood with anti-FcεR stimulation control in stimulation buffer without IL-3 and staining cells for CCR3 and CD203c for 15 minutes at 37° C., (2) lysing red blood cells and fixing cells with Lysing Reagent at room temperature for 10 minutes, (3) washing cells with Wash Buffer, and (4) acquiring data on a flow cytometer. Thus, antibody staining correlates directly with basophil activation. Activated basophils were also defined as CCR3+, low side scatter and CD203c+. FIG. 5A shows the percent of activated basophils (CD63+) using stimulation buffer with IL-3. FIG. 5B shows the percent of activated basophils (CD203c+) using stimulation control with IL-3. The results demonstrated that Compound 128 fully inhibits basophil activation at a concentration of 1 µM, whereas in contrast, acalabrutinib had no effect on basophil activation at the same concentration.

Example 4: Constitutive KIT Activation Results in "Twitchy" Mast Cells

Figure 6:
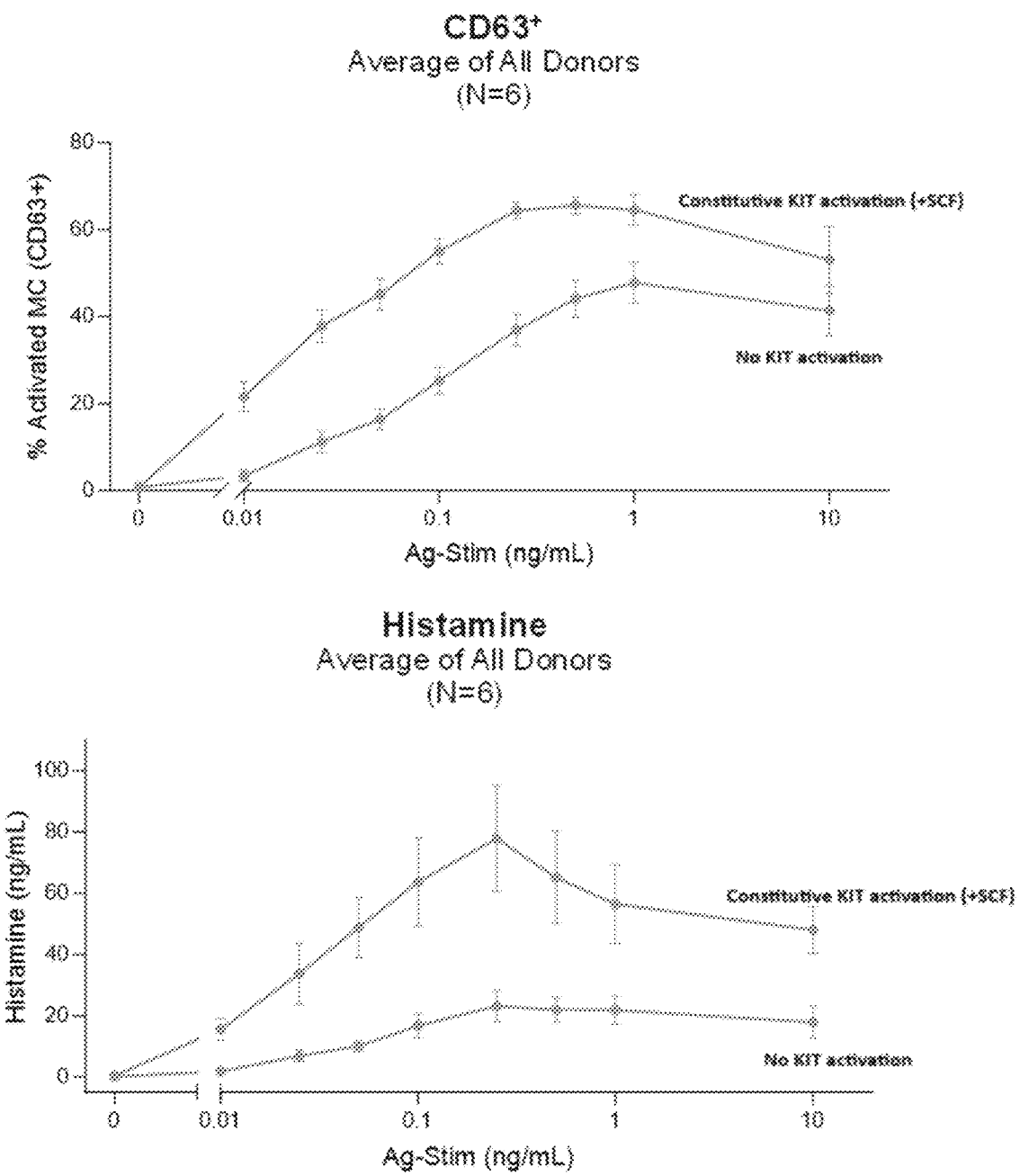
FIG. 6 are graphs showing that constitutive KIT activation results in mast cells that are "twitchy" meaning more sensitive to antigen (Ag) stimulation, compared to mast cells without KIT activation.

Human mast cells were derived from bone marrow CD34+ cells from six healthy donors for up to eight weeks by culturing CD34+ cells in StemSpan SFEM II (Stem Cell Technologies) supplemented with stem cell factor (SCF; 100 ng/mL; R&D System), IL-6 (R&D Systems), IL-3 (R&D Systems) and 1% penicillin/streptomycin (P/S; Gibco) for the first 10 days and in StemSpan SFEM II supplemented with SCF and IL-6 and 1% P/S for the remaining time in culture. Sensitization and stimulation of cells were conducted by (1) sensitizing with IgE specific for 4-hydroxy-3-nitrophenylacetyl hapten (NP-IgE; 0.1 µg/mL; Sertoec) for 18 hours in the presence or absence of SCF (100 ng/mL) to mimic mast cells in ISM and healthy donors, respectively, and (2) stimulating with NP-bovine serum albumin (NP-BSA or antigen; 0.1 µg/mL; Biosearch Technologies) for 15 minutes. Supernatant was collected and histamine levels were measured using a Histamine ELISA kit (Eagle Biosciences). Cells were washed twice with 1×PBS containing 0.5% BSA (FACS buffer), stained for CD63 (Becton Dickinson), FcεRIα (Becton Dickinson), CD117 (Kit receptor; Beckman Coulter) and near-IR dead cell stain (nIR; Invitrogen) for 30 minutes on ice, washed twice with FACS buffer and data was acquired on a flow cytometer. Live activated mast cells were defined as nIR−, FcεRIα+, CD117+ and CD63+. Percent of activated mast cells was calculated as number of activated mast cells over the total number of mast cells. FIG. 6 shows the percent activated mast cells (CD63+) and histamine levels when cells have continuous KIT activation and no KIT activation. The results demonstrate that the cells simulating the ISM condition are more sensitive to antigen-induced degranulation compared to cells simulating a healthy condition.

Figure 7:
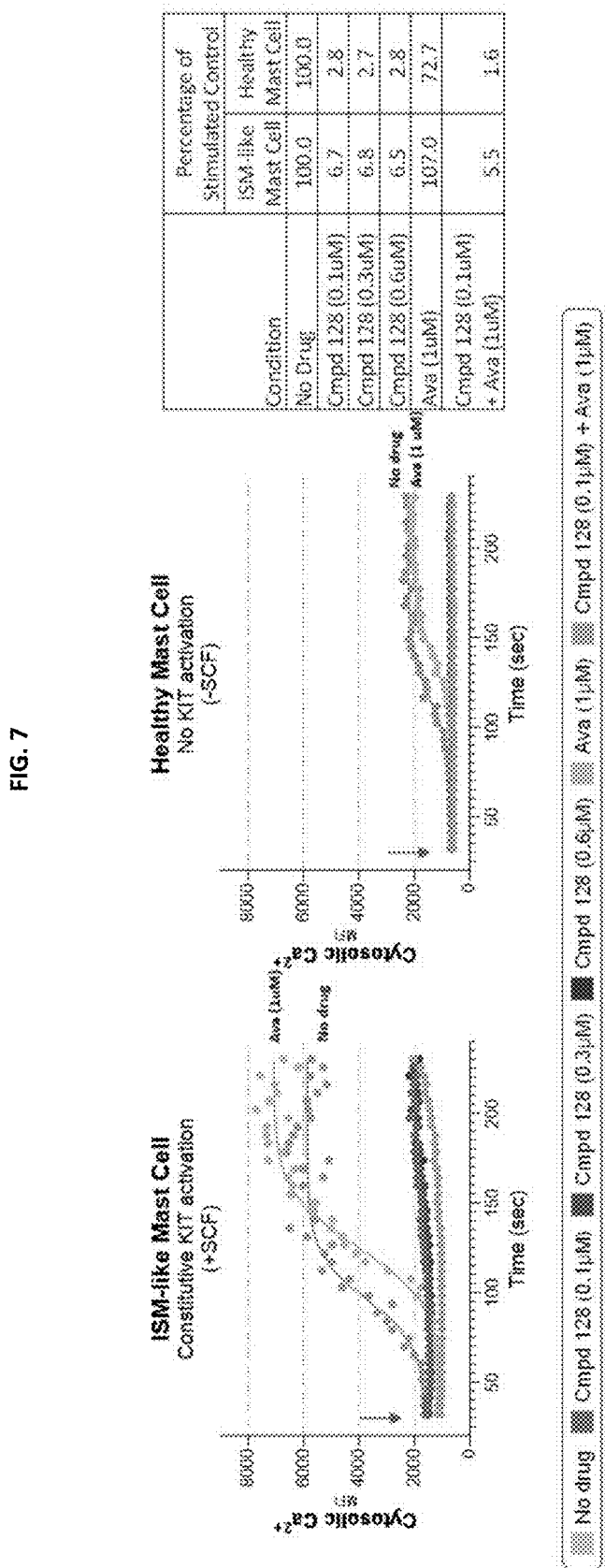
FIG. 7 are graphs showing that a BTK inhibitor inhibits antigen-triggered calcium signaling (a precursor event to degranulation) in human mast cells and that mast cells stimulated in Stem Cell Factor (SCF) containing media (ISM-like) influx higher levels of calcium than healthy mast cells (without SCF).

Example 5: Inhibition of Calcium Signaling in Human Mast Cells Through BTK Inhibition Compound 128 Inhibits Calcium Signaling in Human Mast Cells. Human mast cells were differentiated from bone marrow CD34+ cells from a healthy donor, cultured and sensitized as set forth in Example 4. Using Calcium Flux Assay Kit (Abcam), cells were stained with a 520 AM dye in Assay Buffer for 30 minutes and resuspended in mast cell culture media. Cells were then (1) treated with Compound 128, avapritinib or the combination of Compound 128 and avapritinib for 2 hours, (2) stimulated with NP-BSA (antigen; 0.1 µg/mL) for 3.5 minutes and (3) data was acquired for the duration of the stimulation. The median fluorescence intensity of cytosolic calcium was measured across the stimulation time period and graphed to represent the calcium influx profile. The area under the curve (AUC) of the calcium influx profile was calculated and normalized as a percent of stimulated control. FIG. 7 shows the calcium influx profile and percent of stimulated control across different drug conditions in an ISM-like mast cell or healthy mast cell. Black arrows show the addition of NP-BSA (0.5 ng/mL). The results demonstrate that a BTK inhibitor (Compound 128 or a pharmaceutically acceptable salt thereof) blocks calcium influx in mast cells in both ISM-like (+SCF) and healthy (−SCF) mast cells with less than 7% and 3% of mast cells undergoing calcium influx, respectively. The ISM-like mast cells (+SCF) show higher calcium levels in response to IgE-mediated antigen exposure.

Abbreviations: Ava, avapritinib; MFI, mean fluorescence intensity; SCF, stem cell factor; sec, seconds.

Example 6: Inhibition of "Twitchy" Mast Cells Through BTK Inhibition

Figure 8:
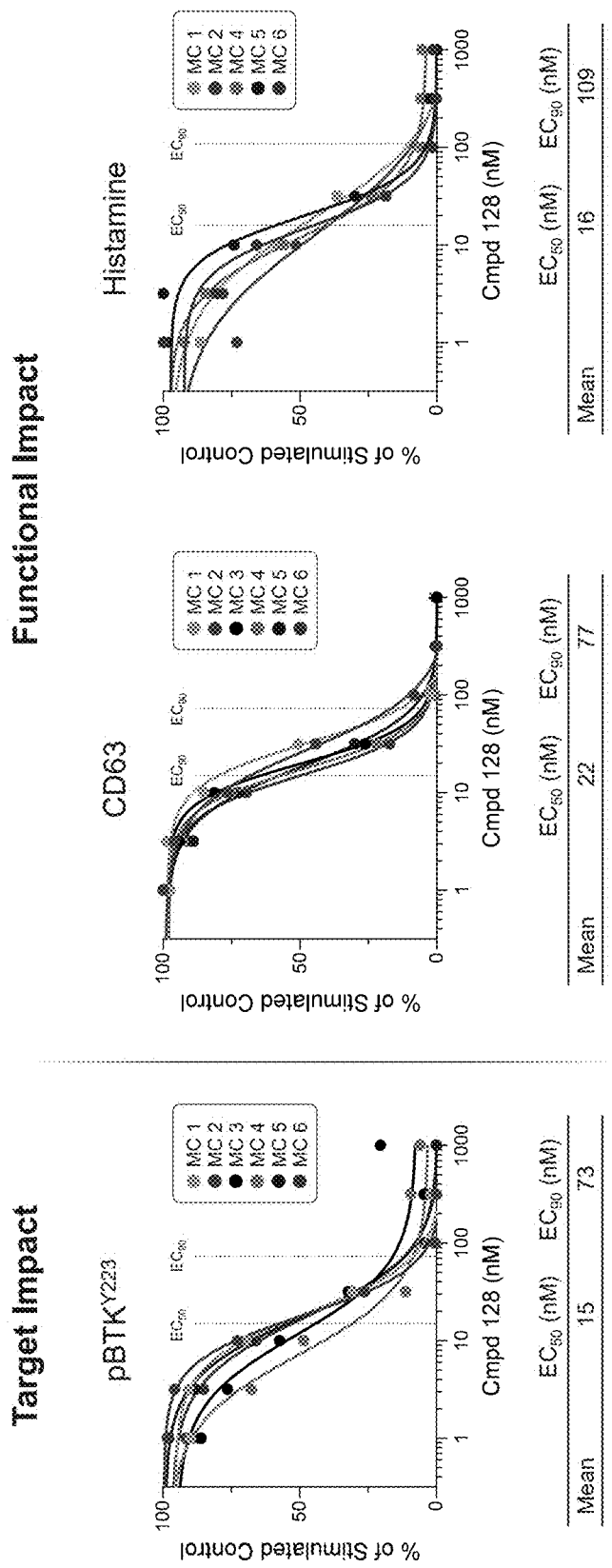
FIG. 8 are graphs showing that a BTK inhibitor can inhibit IgE-mediated BTK phosphorylation and the downstream degranulation readouts in "twitchy" mast cells (+SCF conditions) from multiple donors.

Human mast cells were differentiated from bone marrow CD34+ cells from six healthy donors, cultured and sensitized as set forth in Example 4. Human mast cells were cultured, sensitized and stimulated in ISM-like conditions as set forth in Example 4 and were treated with Compound 128 for two hours prior to stimulation. For pBTK test, cells were (1) stained for rabbit anti-human pBTK, FcεRIα and CD117 overnight at 4° C., (2) washed twice with FACS buffer, (3) stained with goat anti-rabbit secondary antibody for 30 minutes on ice, (4) washed twice with FACS buffer and (5) data was acquired on a flow cytometer. Mast cells were defined as FcεRIα+ and CD117+. The median fluorescence intensity of phosphorylated BTK was measured. CD63 and histamine levels in these cells were measured and percent activated mast cells were calculated as set forth in Example 4. The percent of stimulated control for pBTK, activated mast cells (CD63+) and histamine levels was calculated. A four-parameter logistic regression analysis was performed on the percent of stimulated controls to determine the $EC_{50}$ and $EC_{90}$. FIG. 8 shows the percentage of stimulated control potency curves for antigen-induced BTK phosphorylation and degranulation (CD63 and histamine). The results demonstrate that compound 128 potently inhibits IgE-mediated BTK phosphorylation and degranulation in ISM-like mast cells.

Figure 9:
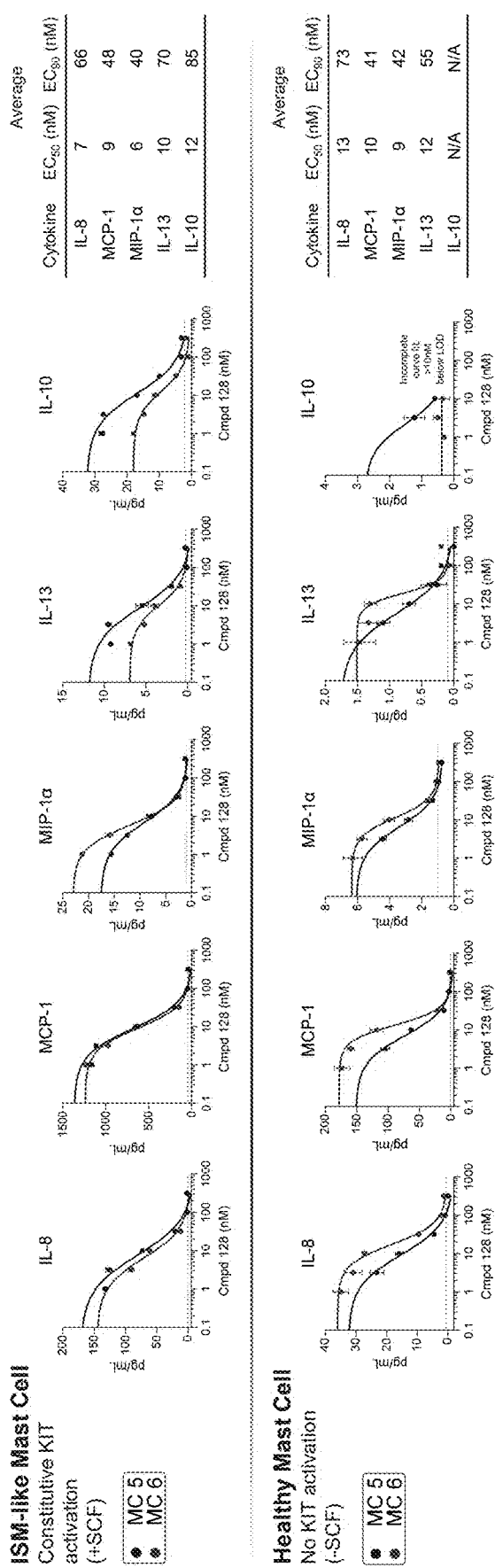
FIG. 9 are graphs showing that a BTK inhibitor can inhibit cytokine production from antigen stimulated mast cells when KIT is activated (+SCF) or when KIT is not activated (−SCF).

Example 7: Inhibition of Cytokine Production in "Twitchy" Mast Cells Through BTK Inhibition Human mast cells were differentiated from bone marrow CD34+ cells from two healthy donors, cultured and sensitized in ISM-like and healthy mast cell conditions as set forth in Example 4, treated with Compound 128 for two hours and stimulated with antigen for four hours. Supernatant was collected and cytokine levels were measured using the BD Cytometric Bead Array (CBA) human soluble protein master buffer kit (Becton Dickinson) and BD CBA human soluble protein flex sets for IL-8, MCP-1, MIP-1α, IL-13 and IL-10 (Becton Dickinson). A four-parameter logistic regression analysis was performed on the cytokine levels to determine the $EC_{50}$ and $EC_{90}$. FIG. 9 shows the potency curves for antigen-induced cytokine production in ISM-like and healthy mast cell conditions. The results demonstrate that IgE-mediated cytokine production is greater in ISM-like mast cells than healthy mast cells and this greater cytokine production is inhibited in the presence of Compound 128. Abbreviations: IL, interleukin; ISM, indolent systemic mastocytosis; MCP-1, monocyte chemoattractant protein 1; MIP-1a, macrophage inflammatory protein-1 alpha; unstim, unstimulated levels.

Example 8: Clinical Study to Evaluate Efficacy of BTK Inhibitors in Indolent Systemic Mastocytosis Patients Who are Resistant to Best Available Therapy Efficacy of Compound 128 will be evaluated among adult subjects diagnosed with ISM as defined by WHO diagnostic criteria. The subjects have moderate-to-severe symptoms based on minimum mean total symptom scores (TSS) of ISM-TSAF over the 14-day eligibility screening period for assessment of TSS of ISM-TSAF. Minimum baseline TSS of ISM-TSAF for eligibility is ≥28. Subjects will receive either 50, 75, 100 or 150 mg BID of Compound 128 plus best supportive care. Subject will be treated for twenty-four weeks and will be evaluated at twelve weeks and twenty-four weeks. Evaluation will be based on the 14-day rolling average TSS of ISM-TSAF or SISM-TSAF. The TSS of ISM-TSAF is based on patient reporting on eleven separate symptoms, measuring the severity of a broad range of mastocytosis-related symptoms over the prior 24 hours, based on a score from zero (no symptoms) to ten (worst possible symptoms experienced) scale for a TSS between 0-110. The eleven symptoms to be scored by the subject are fatigue, abdominal pain, diarrhea, skin spots, itching, flushing, brain fog, headache, dizziness and bone pain. The TSS of SISM-TSAF is based on patient reporting on nine separate symptoms based on a score from zero (no symptoms) to ten (worst possible symptoms experienced). The nine symptoms to be scored by the subject are muscle pain, runny nose, nasal congestion, wheezing, shortness of breath, throat itching, heart palpitations, difficulty concentrating, and diarrhea. The first eight items measure the severity of a broad range of mastocytosis-related symptoms over the prior 24 hours. Each of the first eight symptom is assessed on a 0 (None) to 10 (Worst Imaginable) scale for a TSS between 0-80. The 9th item measures incidence of diarrhea over the prior 24 hours. Endpoints will also be based on mean change in TSS of ISM-TSAF or SISM-TSAF based on 14-day average of patient-reported severity of ISM symptoms; mean change in serum tryptase level, KIT D816V VAF, change in best supportive care medications and change in number of anaphylactic episodes.

Figure 23:
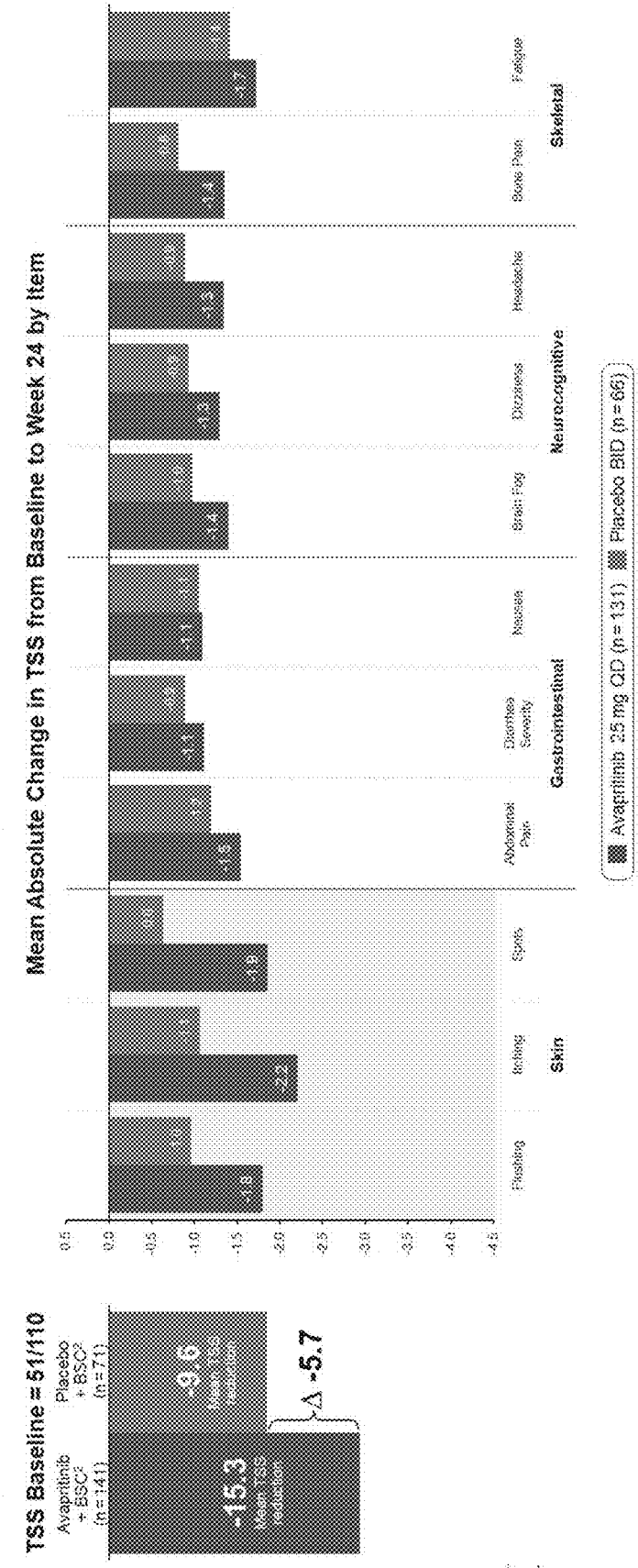
FIG. 23 shows the change in total symptom score based on the ISM-SAF survey for ISM patients after treatment with avapritinib 25 mg QD at Week 24. The total symptom score is reduced by 5.7 points, compared to the placebo.
Figure 24:
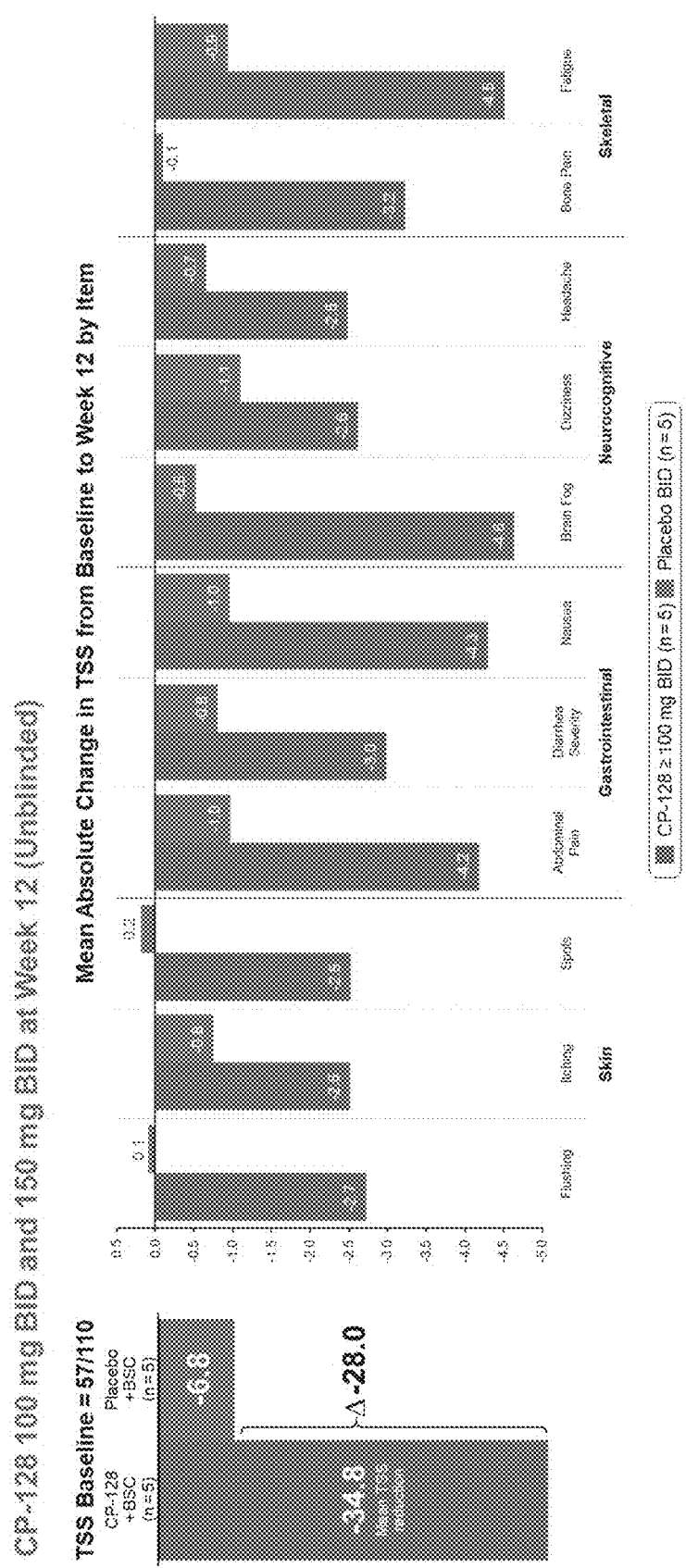
FIG. 24 shows the change in total symptom score based on the ISM-TSAF survey (Tabe 2) for ISM patients after treatment with Compound 128 100 mg BID or 150 mg BID at Week 12. The total symptom score is reduced by 28.0 points, compared to the placebo.
Figure 25:
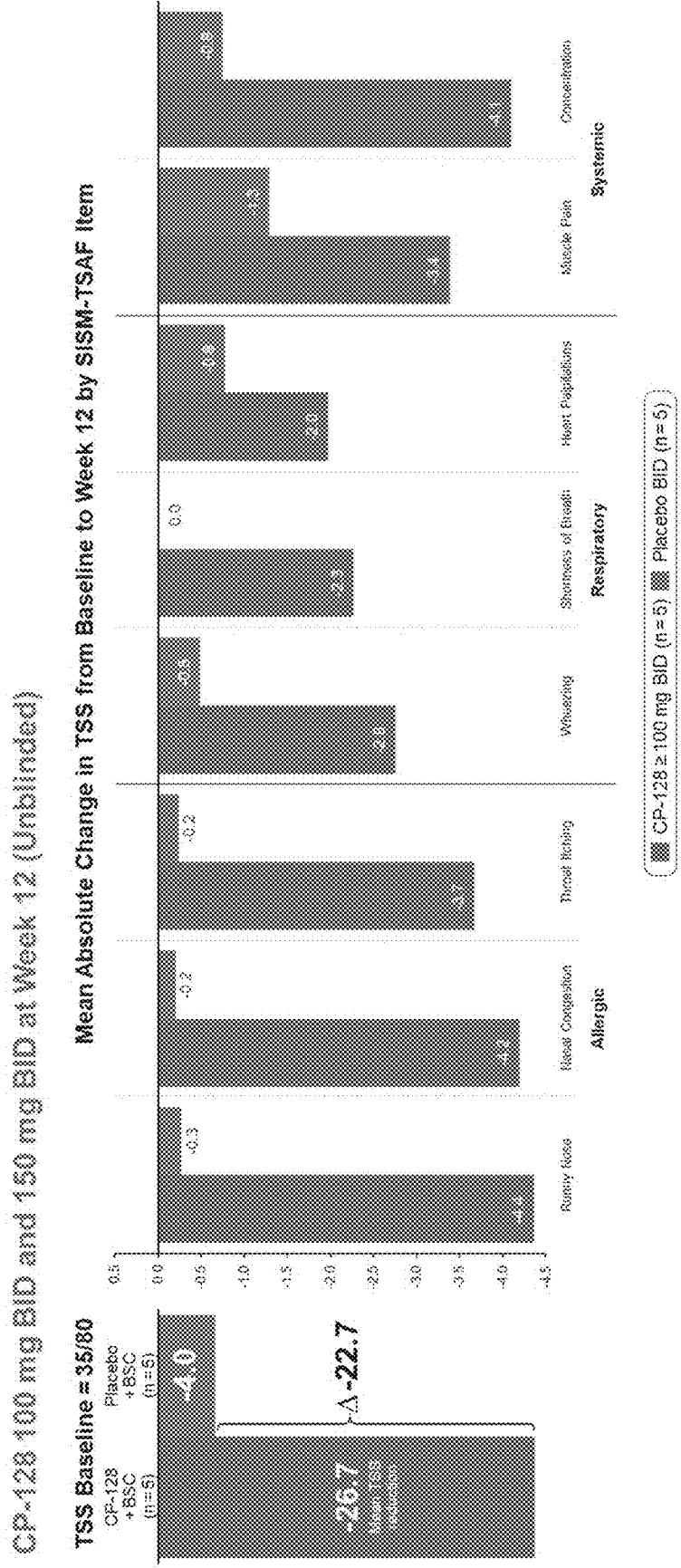
FIG. 25 shows the change in total symptom score based on the SISM-TSAF survey (Table 3) for ISM patients after treatment with Compound 128 100 mg BID or 150 mg BID at Week 12. The total symptom score is reduced by 22.7 points, compared to the placebo.
Figure 28:
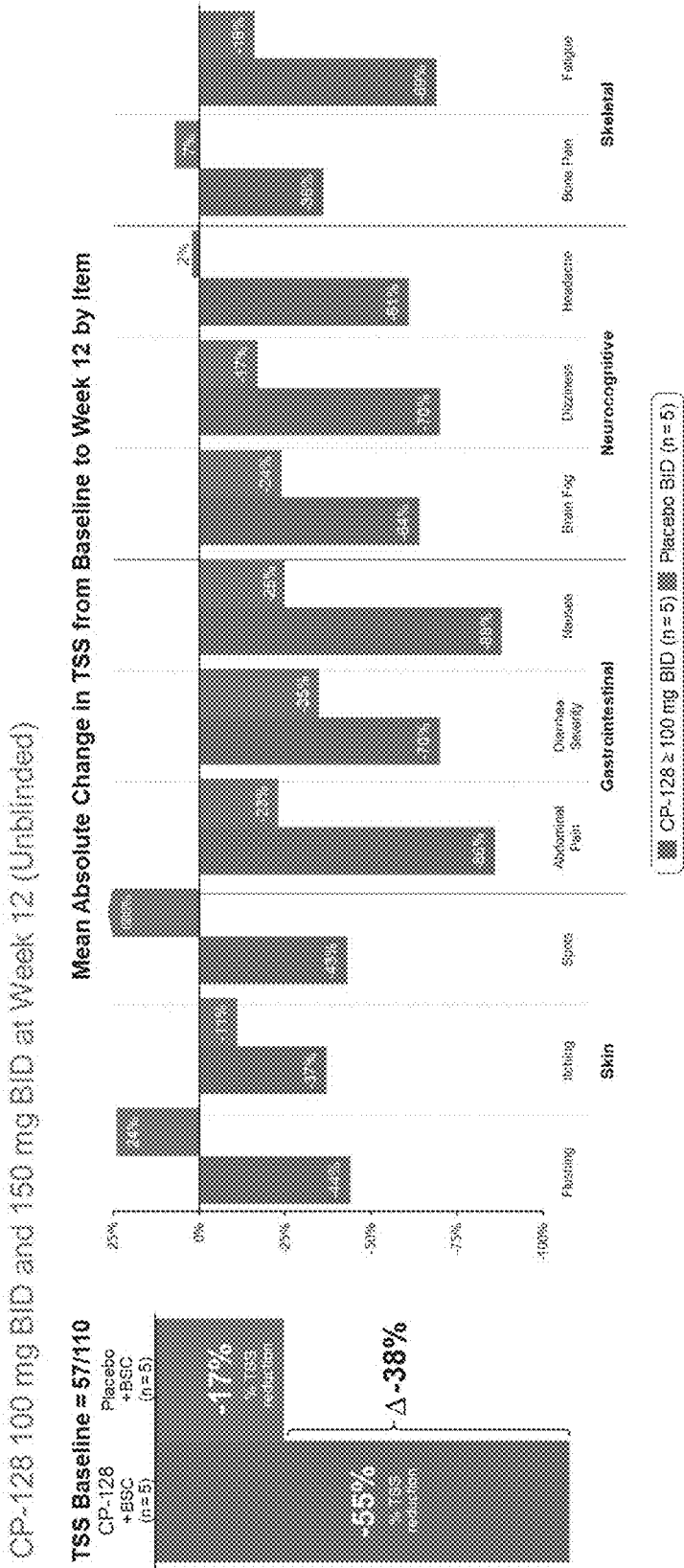
FIG. 28 shows the average reduction of total symptom score for ISM patients after 12-week treatment with Compound 128 100 mg BID or 150 mg BID. The average reduction of total symptom score is 55% compared to the baseline.
Figure 29:
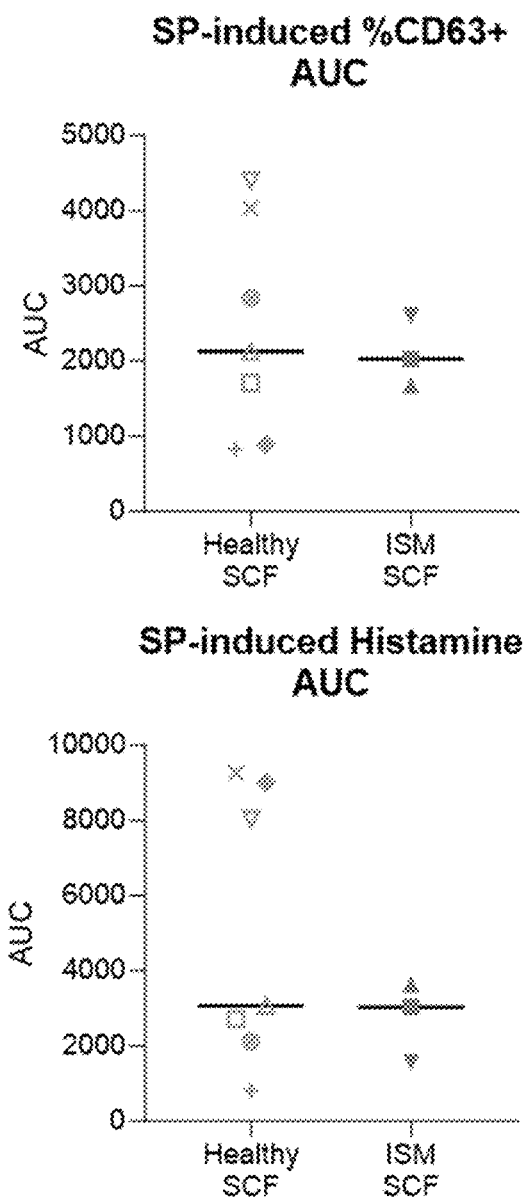
FIG. 29 shows that ISM mast cells are not more sensitive to MRGPR2 agonist SP stimulation compared to healthy mast cells.
Figure 30:
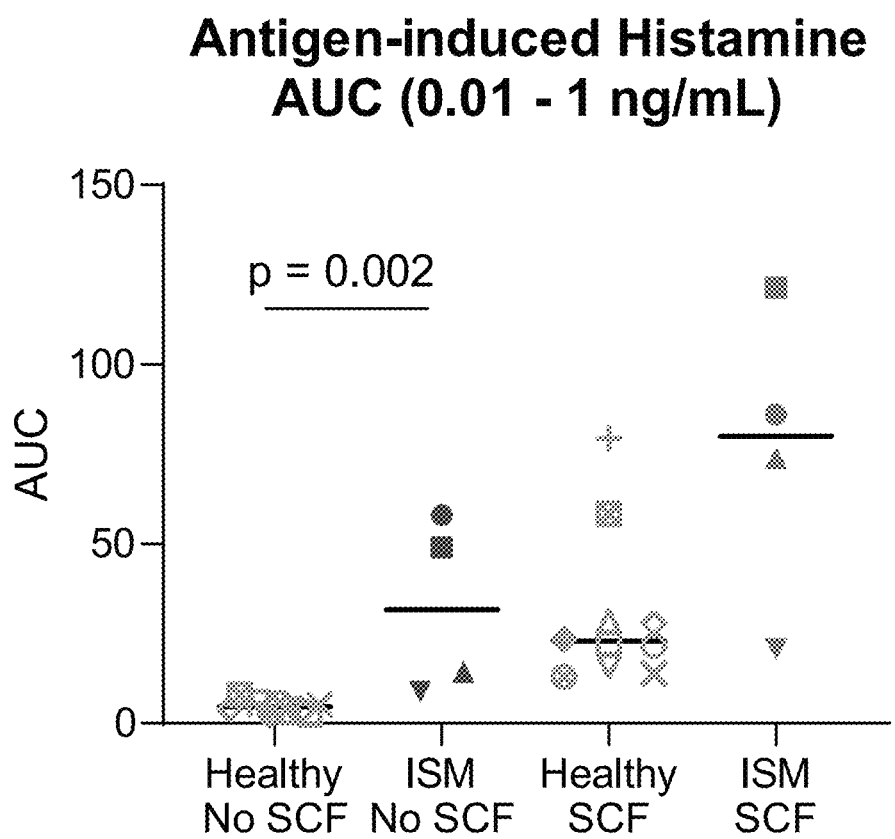
FIG. 30 shows that ISM mast cells are more sensitive to antigen stimulation compared to healthy mast cells.

Five ISM patients have been treated with Compound 128 at 100 mg or 150 mg BID. At week 12, the TSS of ISM-TSAF is reduced by 28 points compared to the placebo group (FIG. 24), and the TSS of SISM-TSAF is reduced by 22.7 points, compared to the placebo (FIG. 25). In contrast, avapritinib 25 mg QD reduced the TSS of ISM-TSAF by 5.7 points at week 24 (FIG. 23). The average reduction of total symptom score of ISM-TSAF is 55% compared to the baseline while the average reduction of total symptom score of ISM-TSAF is 38% compared to the placebo group (FIG. 28).

Figure 26:
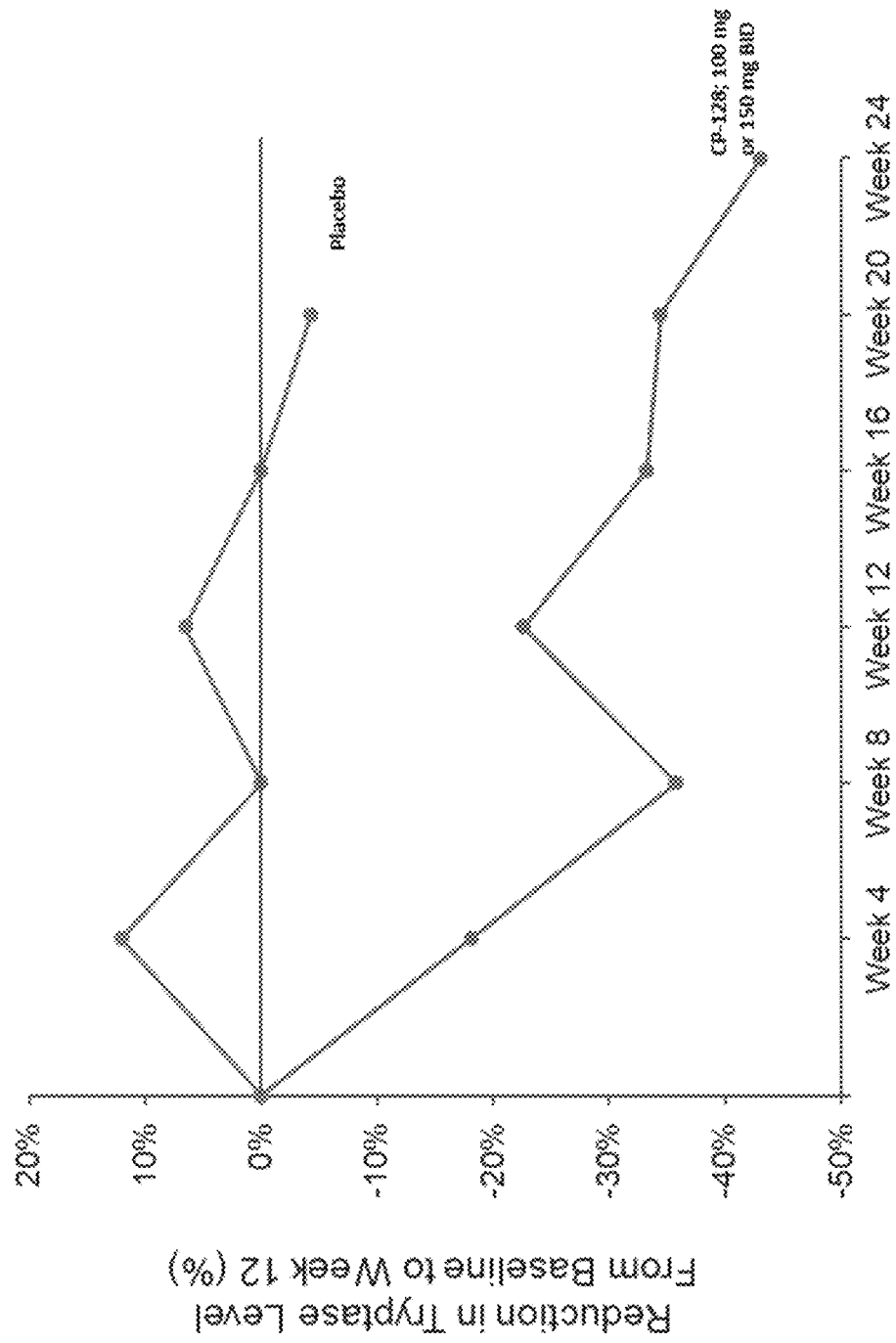
FIG. 26 shows the reduction in serum tryptase for ISM patients after treatment with Compound 128 100 mg BID or 150 mg BID.
Figure 27:
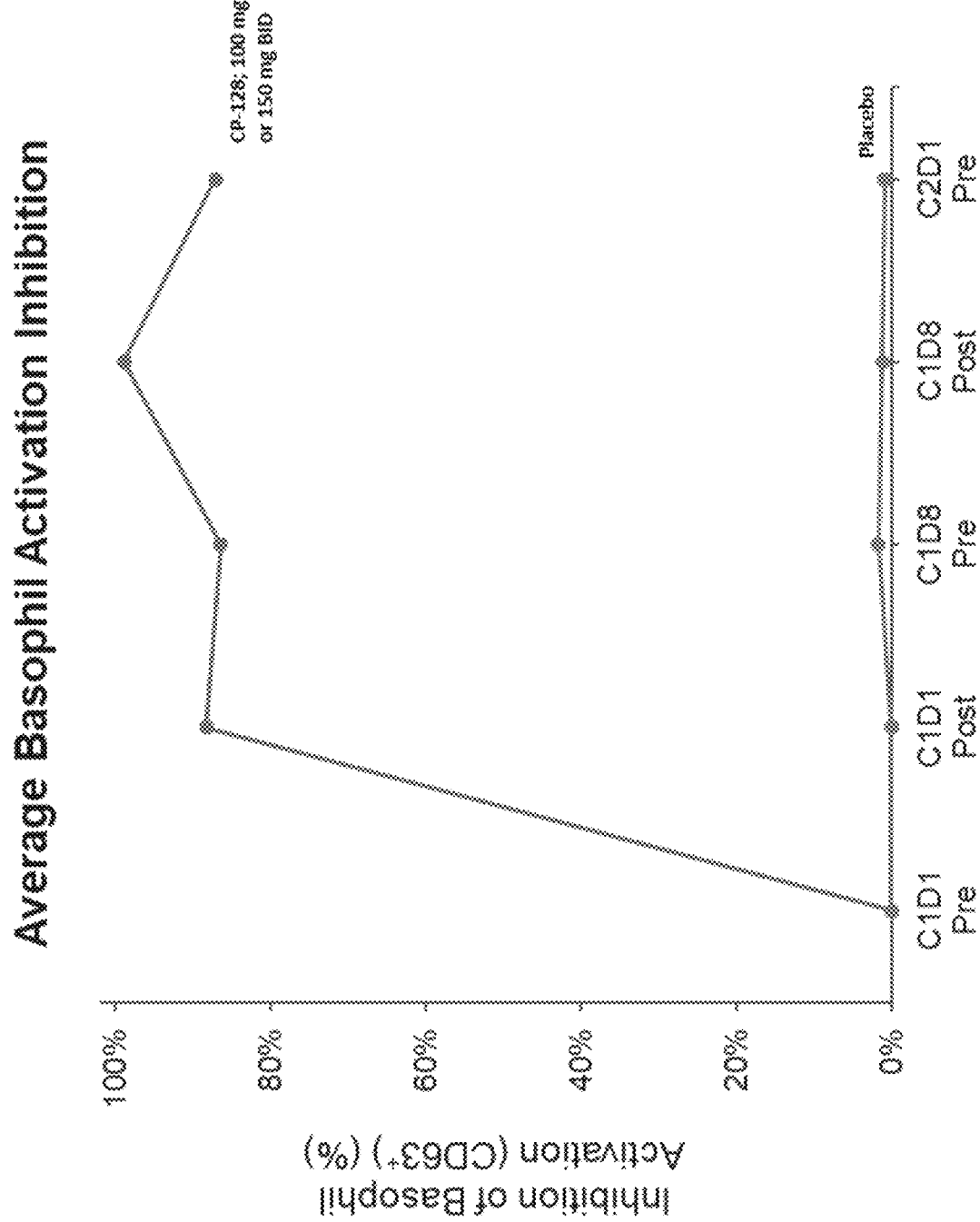
FIG. 27 shows the average basophil activation inhibition for ISM patients after treatment with Compound 128 100 mg BID or 150 mg BID. C1D1 refers treatment cycle one, day one; C1D8 refers to treatment cycle one, day eight; C2D1 refers to treatment cycle 2, day one. Pre refers to predose (30 minutes before the morning dose). Post refers to two hours after the morning dose.

Also, blood samples were collected at the following timepoints: Cycle 1, Day 1: pre-dose (within 30 minutes prior to the morning dose), 0.5, 1.0, 2.0, 3.0, 4.0, and 6.0 hours (±15 minutes) post-morning dose. Cycle 1, Day 8: pre-dose (within 30 minutes prior to the morning dose) and 2 hours (±15 minutes) post-morning dose. Serum tryptase tests were conducted according to Example 14. The average reduction in serum tryptase is shown in FIG. 26, demonstrating that Compound 128 at 100 mg or 150 mg BID is effective in reducing serum tryptase levels. The inhibition of basophil activation was also evaluated following the procedures illustrated in Example 1, as shown in FIG. 27, demonstrating that Compound 128 at 100 mg or 150 mg BID is effective in inhibiting basophil activation.

Example 9: Inhibition of ISM-Like Mast Cell Chemotaxis Through BTK Inhibition

Figure 11:
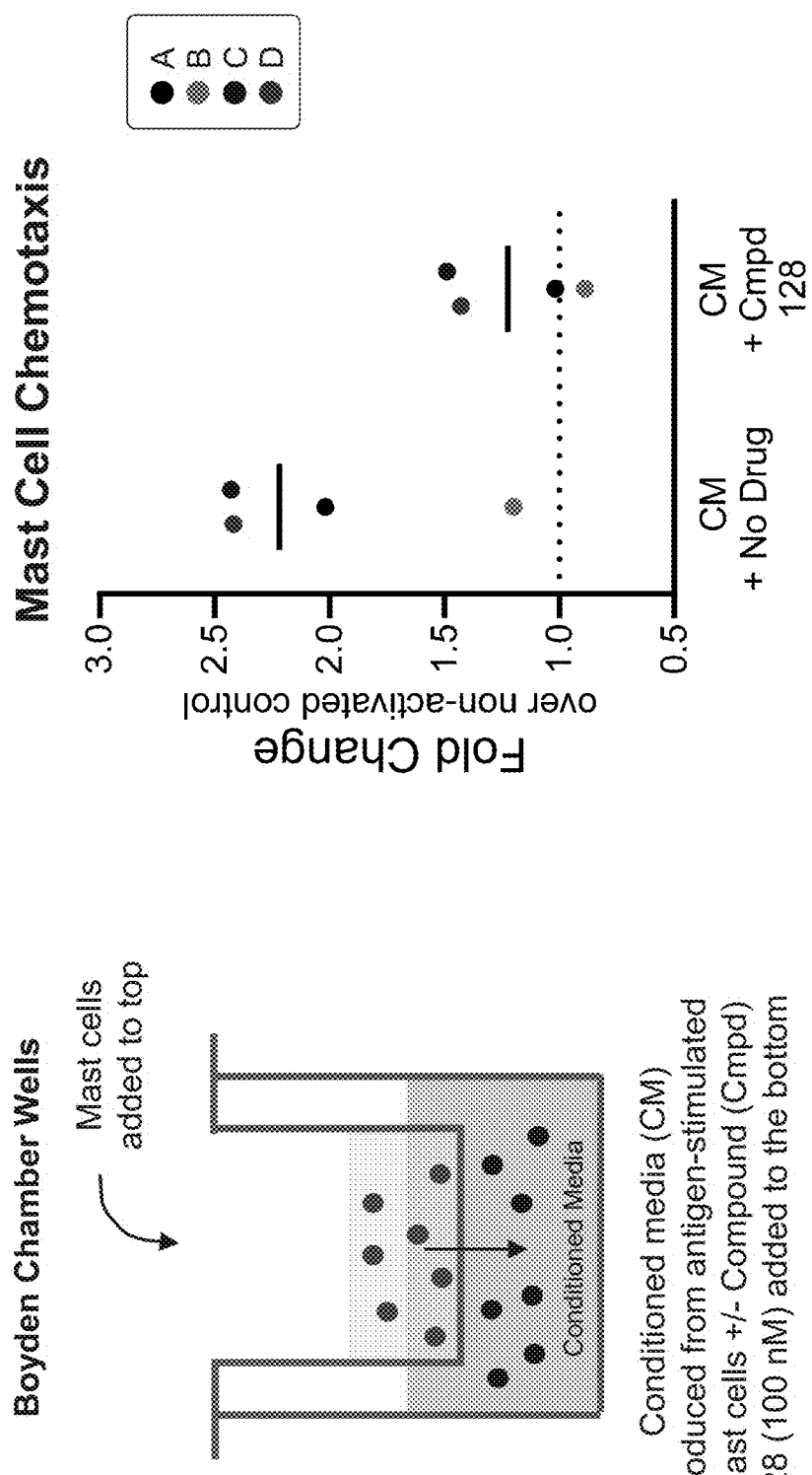
FIG. 11 is a graph showing inhibition of mast cell chemotaxis by blocking chemokine production with Compound 128.

Human mast cells were differentiated from bone marrow CD34+ cells from four healthy donors as set forth in Example 4. Cells were used to produce conditioned media in ISM-like conditions. Conditioned media was the supernatant collected from mast cells cultured with stem cell factor (100 ng/mL), sensitized with NP-IgE (0.1 µg/mL) for 18 hours, treated with Compound 128 for two hours, and stimulated with NP-BSA (antigen; 0.1 µg/mL) for four hours. Migration of mast cells in the top chamber on Transwell 8 µM inserts (Corning) towards the antigen-stimulated conditioned media in the bottom chamber was quantified after four hours using the CellTiter-Glo™ Luminescent Cell Viability Assay Kit (Promega). The amount of luminescence is correlated with live cell numbers. Fold change over the non-activated control was calculated. FIG. 11 shows the fold change over non-activated control of mast cell chemotaxis. The results demonstrate that the chemoattractant activity of mast cells is inhibited by Compound 128. This suggests that mast cell migration towards sites of inflammation should be suppressed by Compound 128.

Example 10: Modulating FcεRI Expression Through BTK Inhibition

Figure 12A:
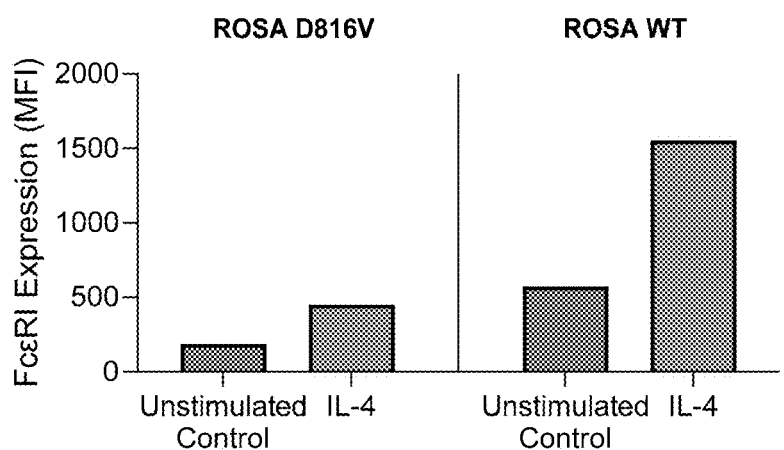
FIG. 12A is a graph showing upregulation of FcεRI expression with IL-4 in ROSA D816V mutant and wildtype cells.
Figure 12B:
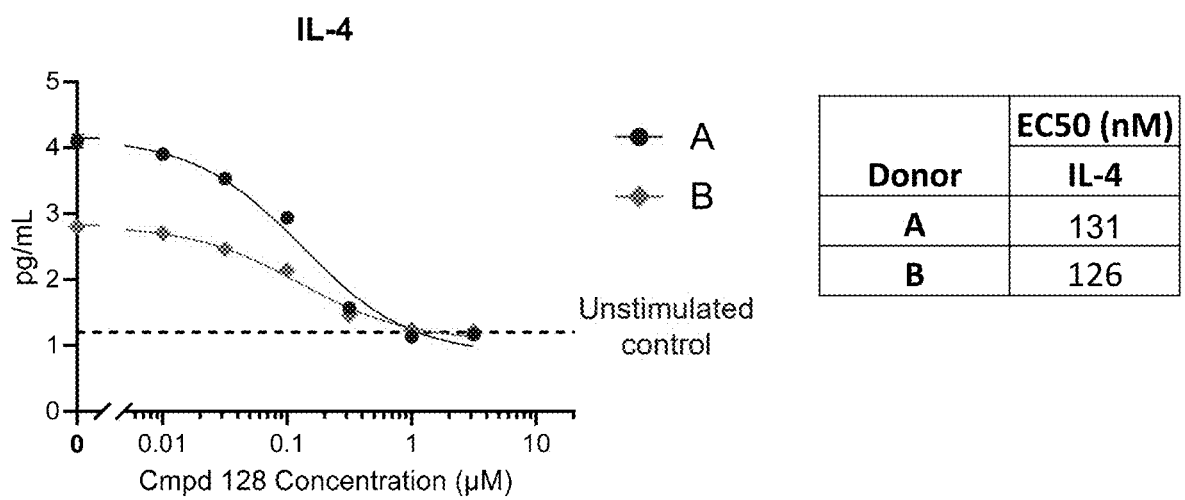
FIG. 12B is a graph showing Compound 128 inhibition of anti-IgE induced IL-4 production from basophils in whole blood.

Human mast cells lines, ROSA with wildtype KIT and ROSA (healthy cells) with D816V KIT mutation (ISM-like cells), were licensed from CRNS Innovation and cultured with or without stem cell factor (100 ng/mL), respectively (FIG. 12A). ROSA cells were stimulated with IL-4 (20 ng/mL; R&D Systems) for 18 hours, stained for FcεRIα (Becton Dickinson) for 30 minutes on ice, washed twice with FACS buffer and data was acquired on a flow cytometer. The median fluorescence intensity of FcεRIα was measured. FIG. 12A shows the IL-4 induced FcεRI expression in ROSA cells. The results demonstrate that IL-4 can upregulate FcεRI expression in ISM and healthy mast cells. Whole blood from a healthy donor was treated with Compound 128 for two hours and the basophils were stimulated with anti-IgE (1 µg/mL; Beckman Coulter) for six hours (FIG. 12B). Plasma was collected and IL-4 levels were measured using the BD CBA human soluble protein master buffer kit and BD CBA human soluble protein flex set for IL-4 (Becton Dickinson). A four-parameter logistic regression analysis was performed on the cytokine levels to determine the $EC_{50}$ and $EC_{90}$. FIG. 12B shows the potency curves for anti-IgE induced IL-4 production in healthy basophils from whole blood. The results demonstrate that IgE-mediated IL-4 production is potently inhibited in the presence of Compound 128. Therefore, Compound 128 may indirectly effect FcεRI expression by the reduction of IL-4 levels.

Figure 13:
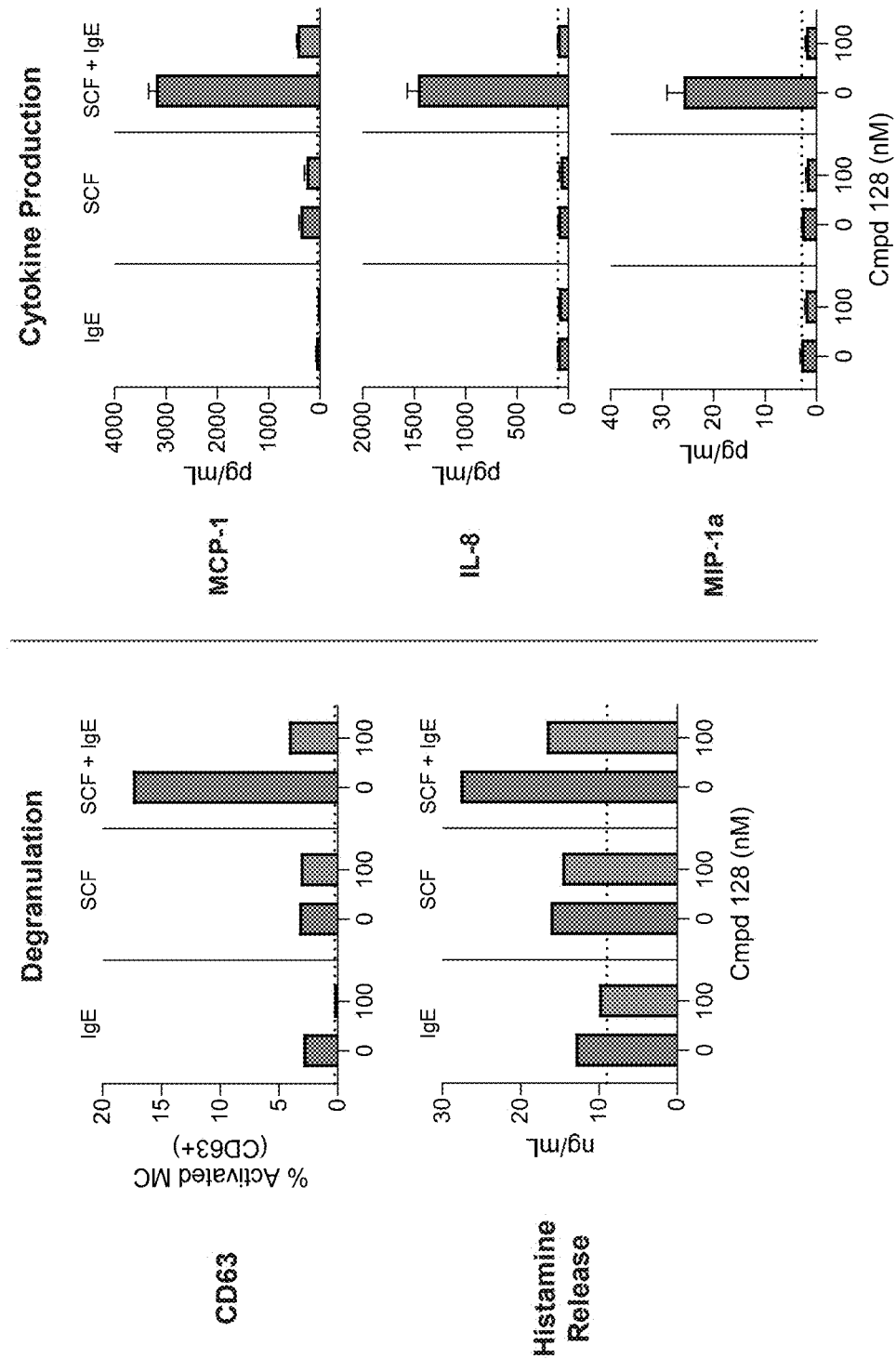
FIG. 13 are graphs showing Compound 128 inhibition of monomeric IgE-mediated (without antigen) degranulation and cytokine production in mast cells.

Example 11: Inhibition of Monomeric IgE-Mediated Degranulation and Cytokine Production in "Twitchy" Mast Cells Through BTK Inhibition Mast cells from a healthy donor were starved of SCF for 18 hours and treated with Compound 128 for 2 hours. Mast cells were stimulated with SCF (100 ng/mL) or myeloma IgE (3 µg/mL; Millipore Sigma) alone or in combination for 30 minutes (CD63 and Histamine) or 24 hours (cytokine production), respectively. For the histamine and cytokine test, supernatant was collected and the levels of histamine and cytokines were measured as set forth in Example 4 for histamine and Example 7 for cytokines. For the CD63 test, the cells were stained for CD63, data was acquired on a flow cytometer and percent activated mast cells calculated as set forth in Example 4. FIG. 13 shows monomeric IgE- and SCF-induced percent activated mast cells (CD63+), histamine levels and cytokine levels. The results demonstrate that monomeric IgE with SCF synergistically increased degranulation (CD63 expression and histamine levels) and cytokines levels in mast cells. The monomeric IgE contribution to degranulation and cytokine production is inhibited by Compound 128.

Example 12: Inhibition of Basophil Activation in ISM Patients

Patients with Indolent Systemic Mastocytosis (NCT04655118) were randomized to 50, 75, 100 or 150 mg BID dosing of Compound 128 or placebo. On a 28-day cycle, blood samples were collected prior to morning dose (pre) or 2 hours after dosing (2 h post). Pre-samples were collected at Cycle 1, Day 1 (C1D1), C1D8 and C2D1. Predose for C1D8 and C2D1 is approximately 12 hours since their last dose of Compound 128 or placebo. Post samples were collected at C1D1 and C1D8.

Figure 14:
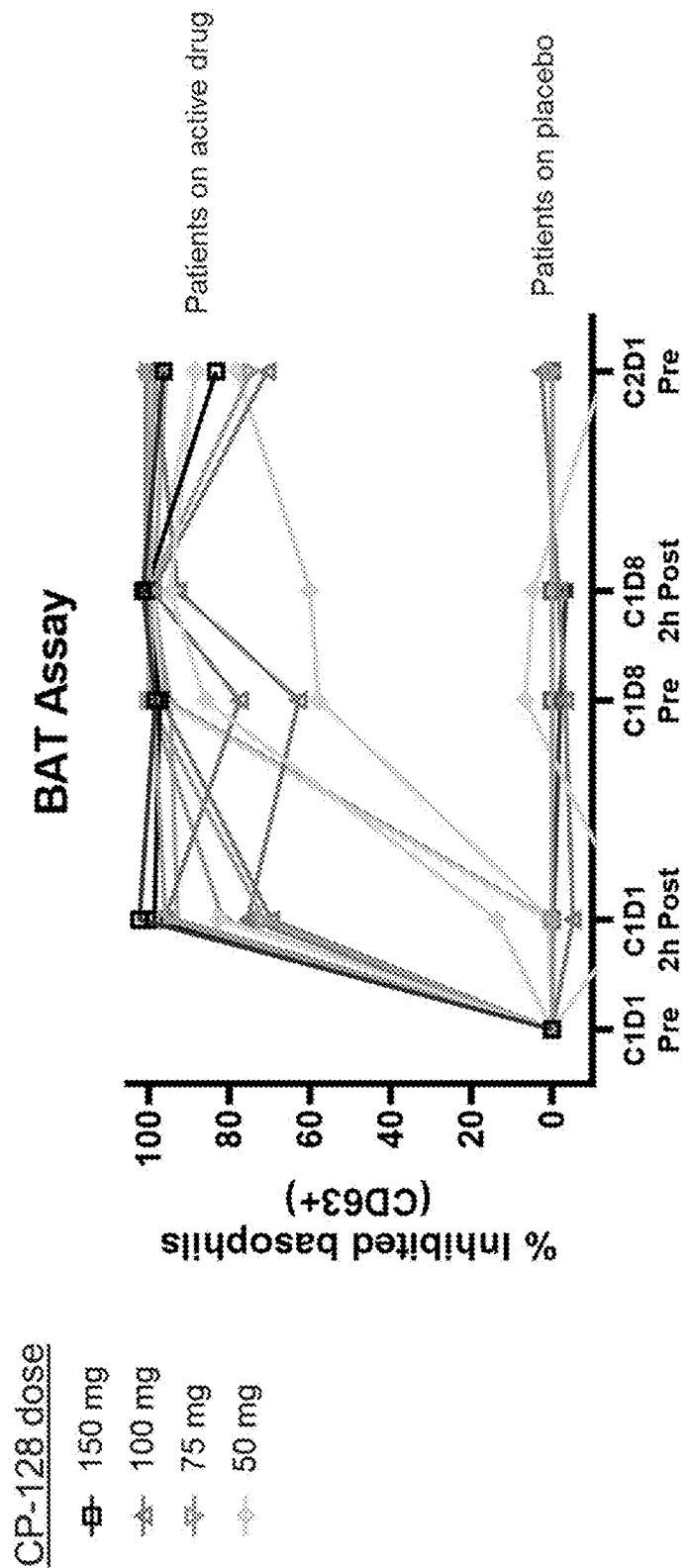
FIG. 14 is a graph showing inhibition of basophils for CD63 activation in ISM patients at 50 mg, 75 mg, 100 mg, and 150 mg BID dose compared to the patients on placebo.

The BAT assay measuring CD63 used the Flow Cast Basophil Activation Kit method and percent activated basophils were calculated as described in Example 1. Percent inhibition of CD63 activation was calculated as (100−(Sample condition−Unstimulated DMSO control)/(Stimulated DMSO control−Unstimulated DMSO control)×100). FIG. 14 shows the percent of inhibited basophils for CD63 activation in ISM patients. In general, the results demonstrate that greater inhibition of basophil activation is achieved in ISM patients with greater dosing of Compound 128.

Figure 15A:
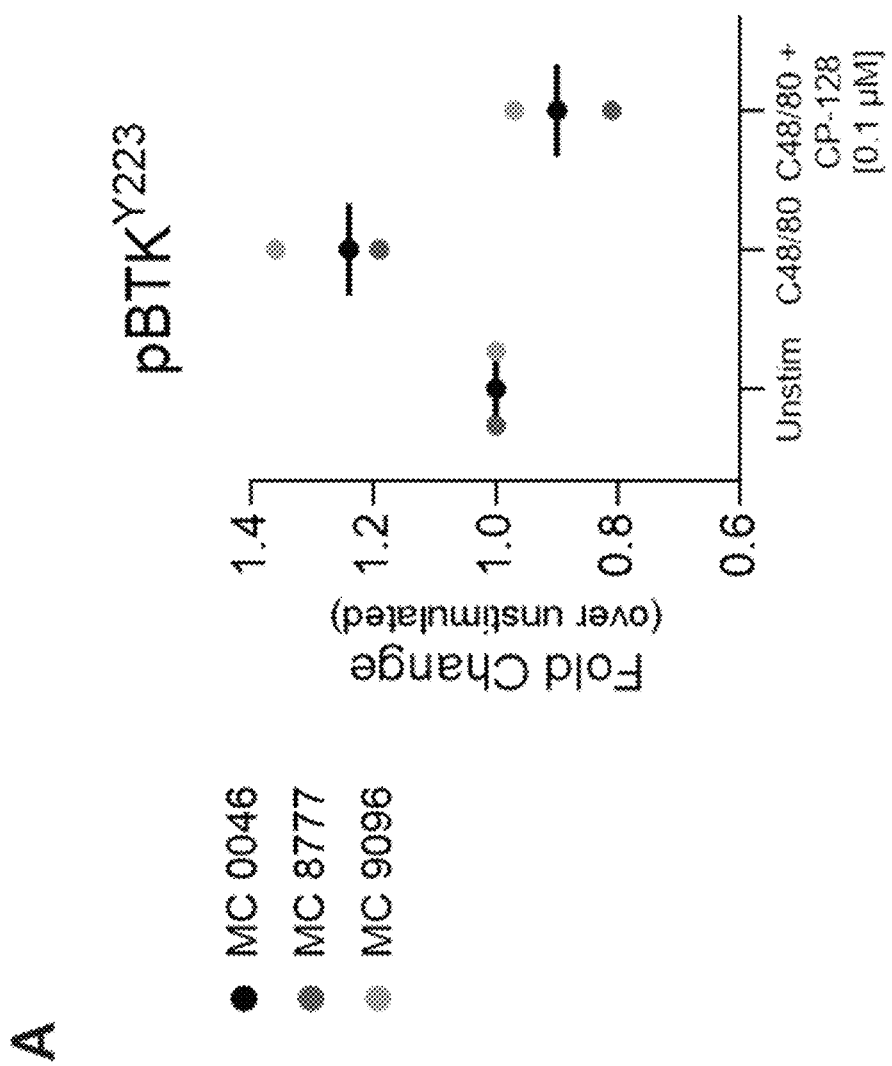
FIGS. 15A-C shows Compound 128 inhibits MRGPRX2-mediated cytokine Production in ISM-like Mast Cells.
Figure 15B:
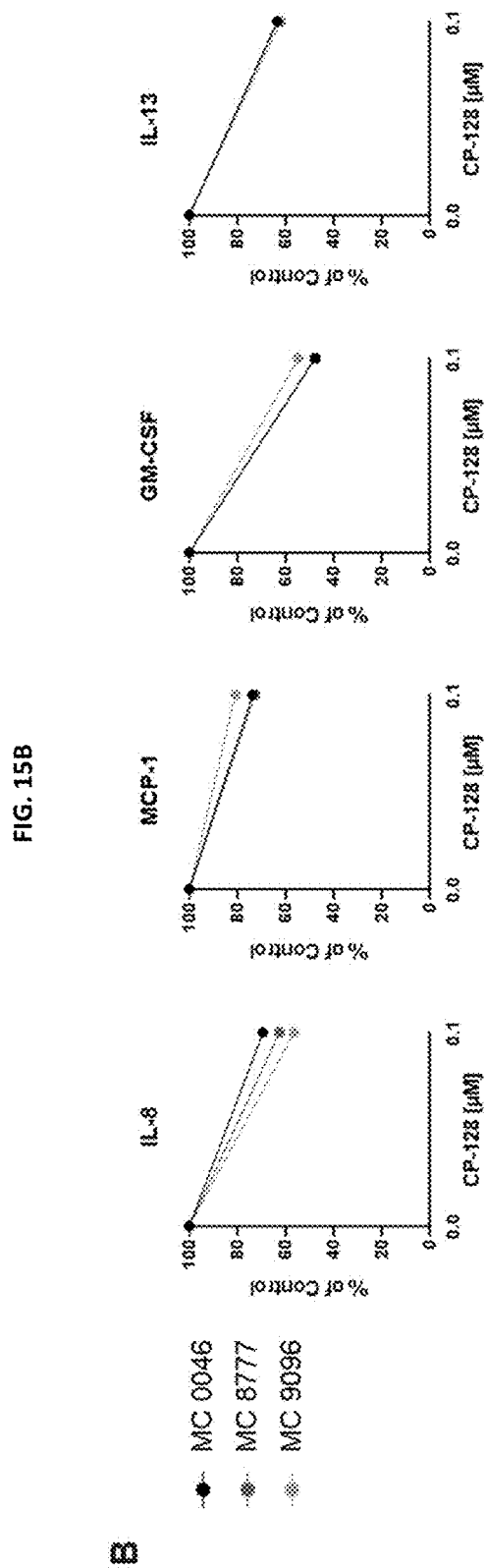
Figure 15C:
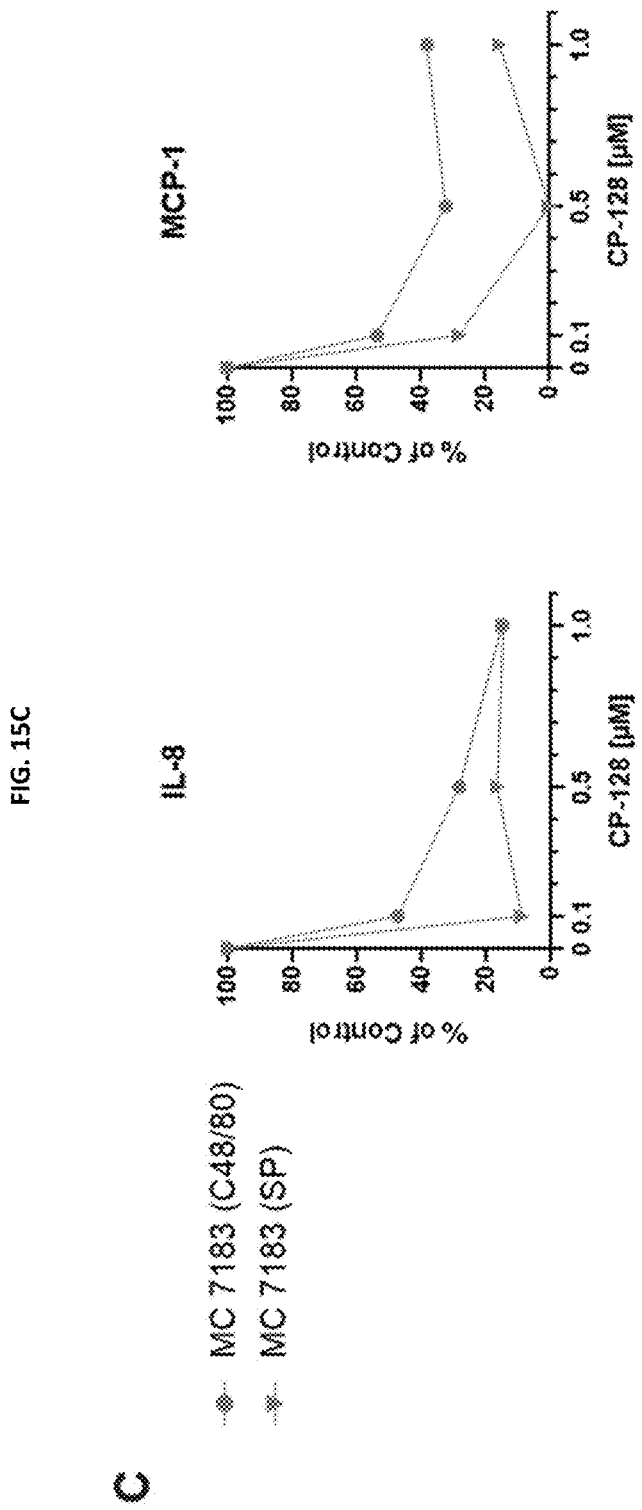
Figure 16:
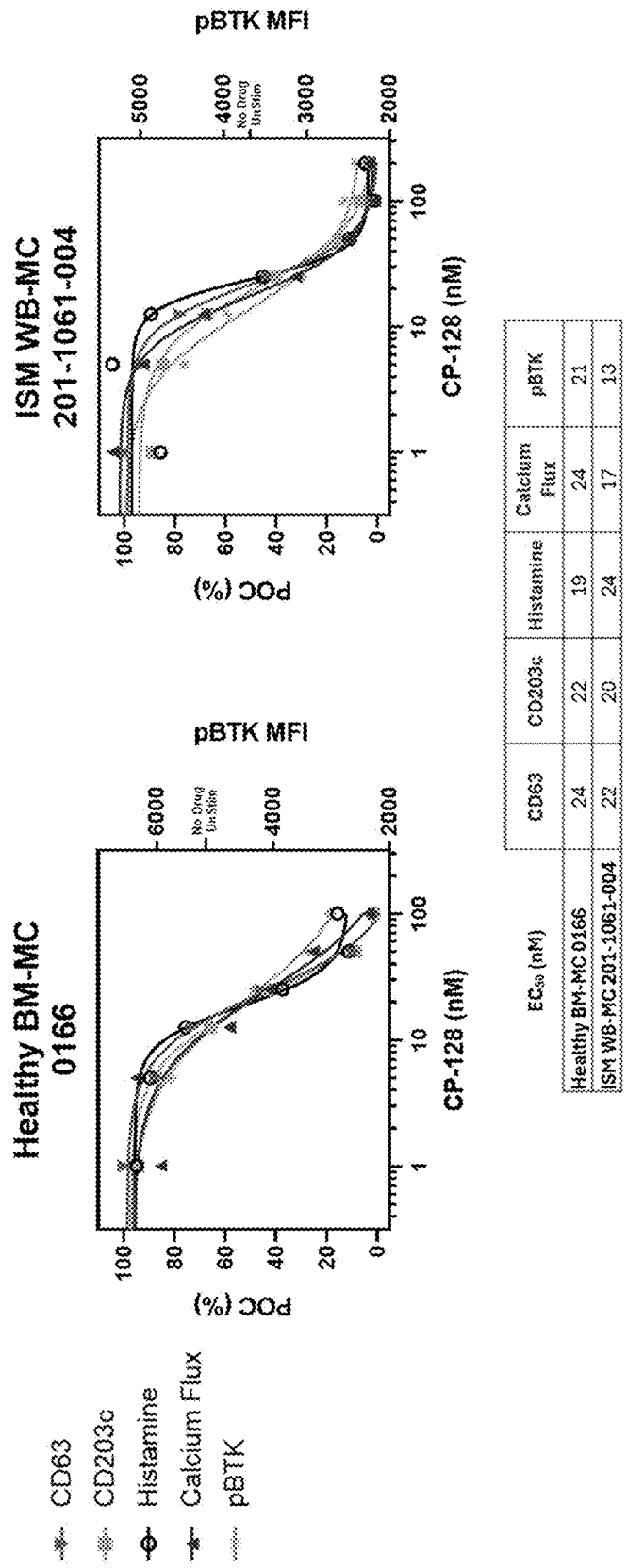
FIG. 16 shows Compound 128 is equipotent across healthy mast cells and ISM mast cells. Healthy BM-MC donor 0166 and ISM WB-MC 1061-004 17 Jan. 2024 and 17 Oct. 2024. Experiments performed in the presence of SCF. Sensitization and Stimulation: NP-IgE (100 ng/mL) 18 hrs, NP-BSA (0.5 ng/mL) for 15 min at 37° C. (CD63, CD203, pBTK and histamine) or 4 min at RT (Calcium Flux).
Figure 17:
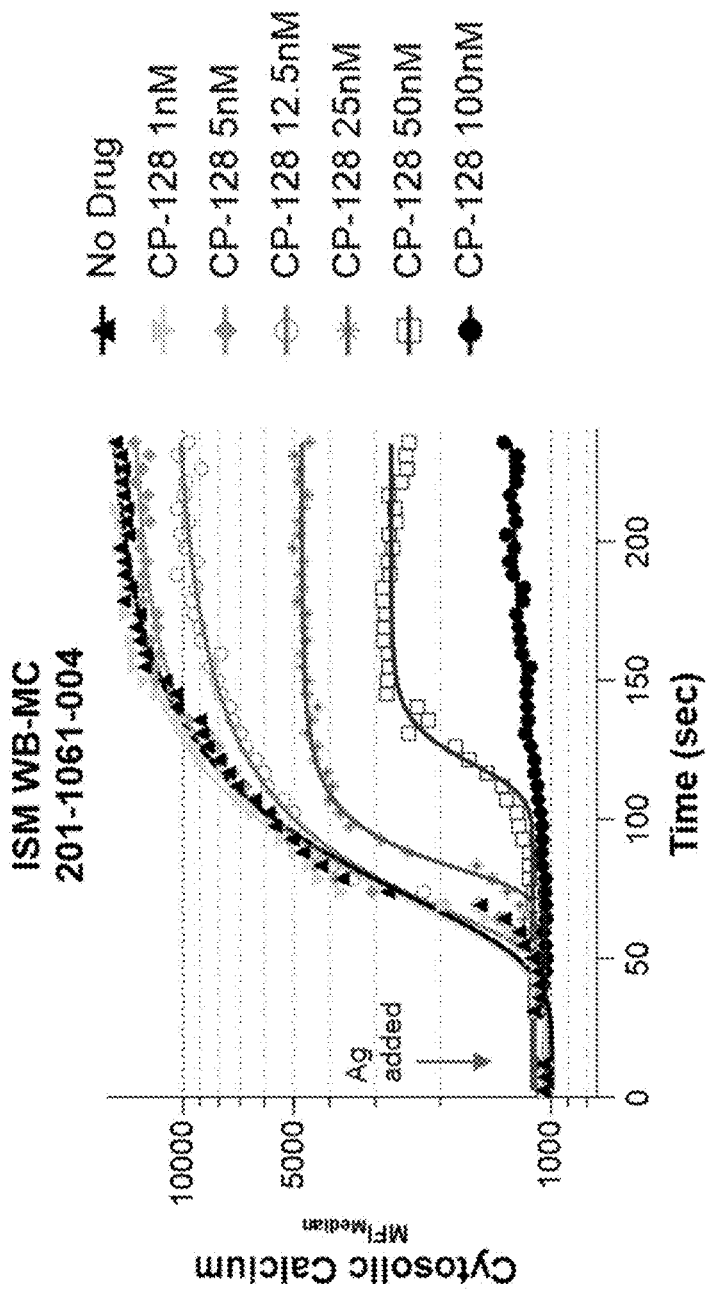
FIG. 17 shows Compound 128 potently inhibits IgE-mediated calcium influx in ISM patient. Mast cell from an ISM patient was treated with Compound 128 at 50 mg, 75 mg, 100 mg, and 150 mg BID dose prior to antigen (Ag) stimulation. ISM 3-2 mast cell donor MC 1061-004 C1D8 D39. Experiments performed in the presence of SCF. Sensitization and Stimulation: NP-IgE (100 ng/mL) 18 hrs, Arrow shows the addition of NP-BSA (0.5 ng/mL): Abbreviations: m, minutes; MC, mast cell; MFI, mean fluorescence intensity; SCF, stem cell factor; sec, second. Percent of Control (POC) based on Area-under-Curve above baseline (1st value).
Figure 18A:
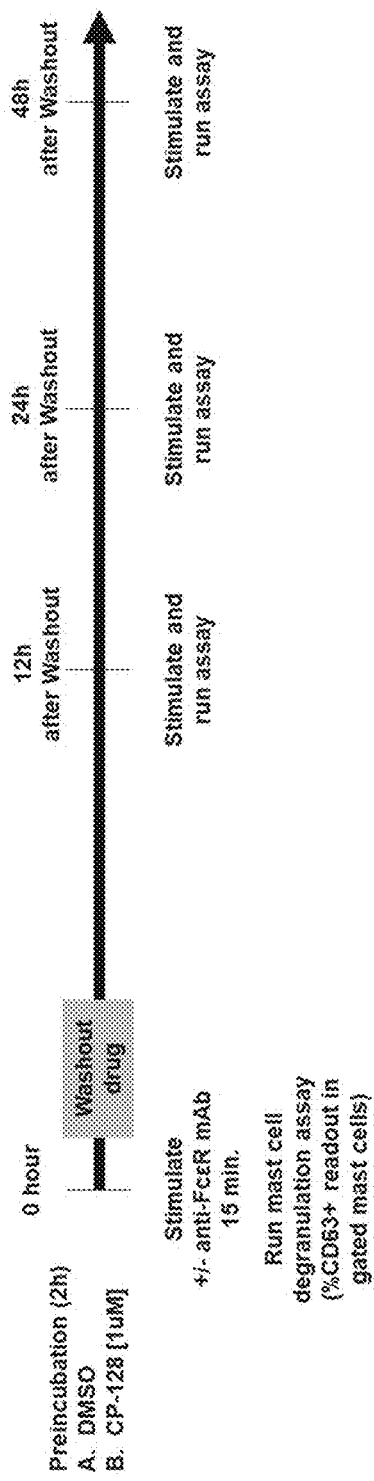
FIG. 18A shows experimental design used to assess mast cells' recovery of degranulation ability.
Figure 18B:
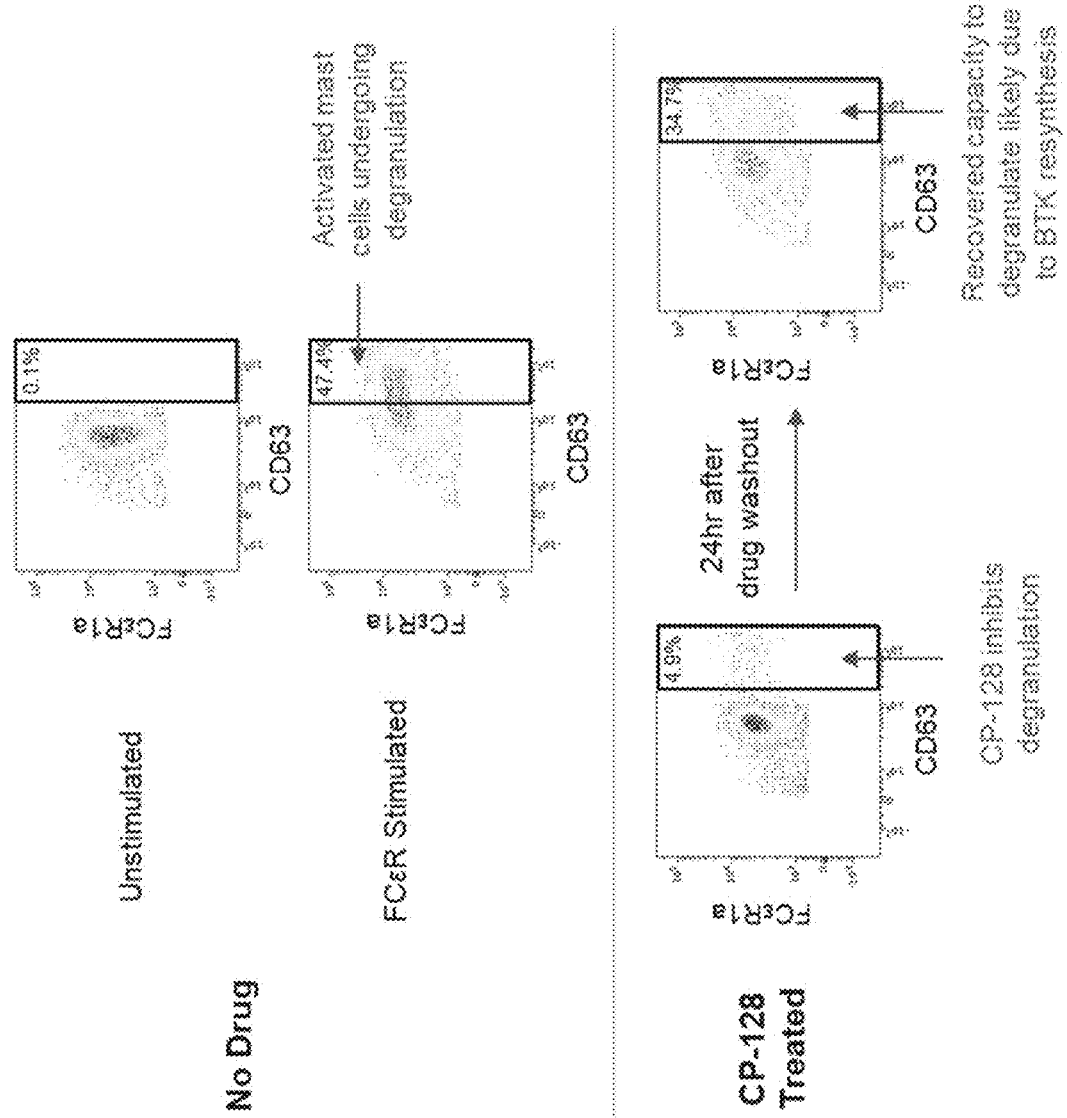
FIG. 18B shows flow cytometry of degranulation inhibited with Compound 128 is restored within 24 hours.
Figure 18C:
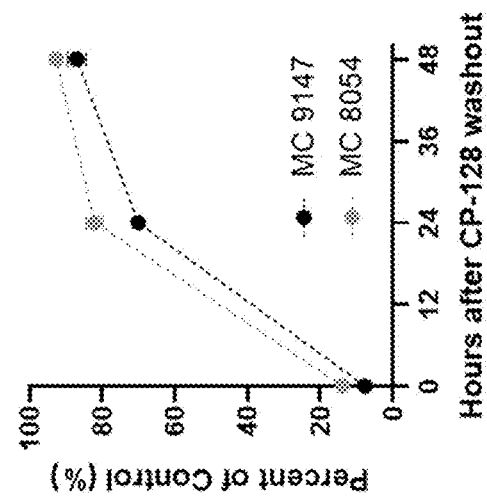
FIG. 18C shows quantification of return of function over time with degranulation returning.
Figure 18C:
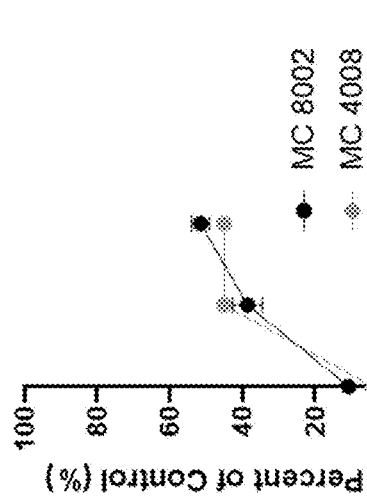
Figure 18D:
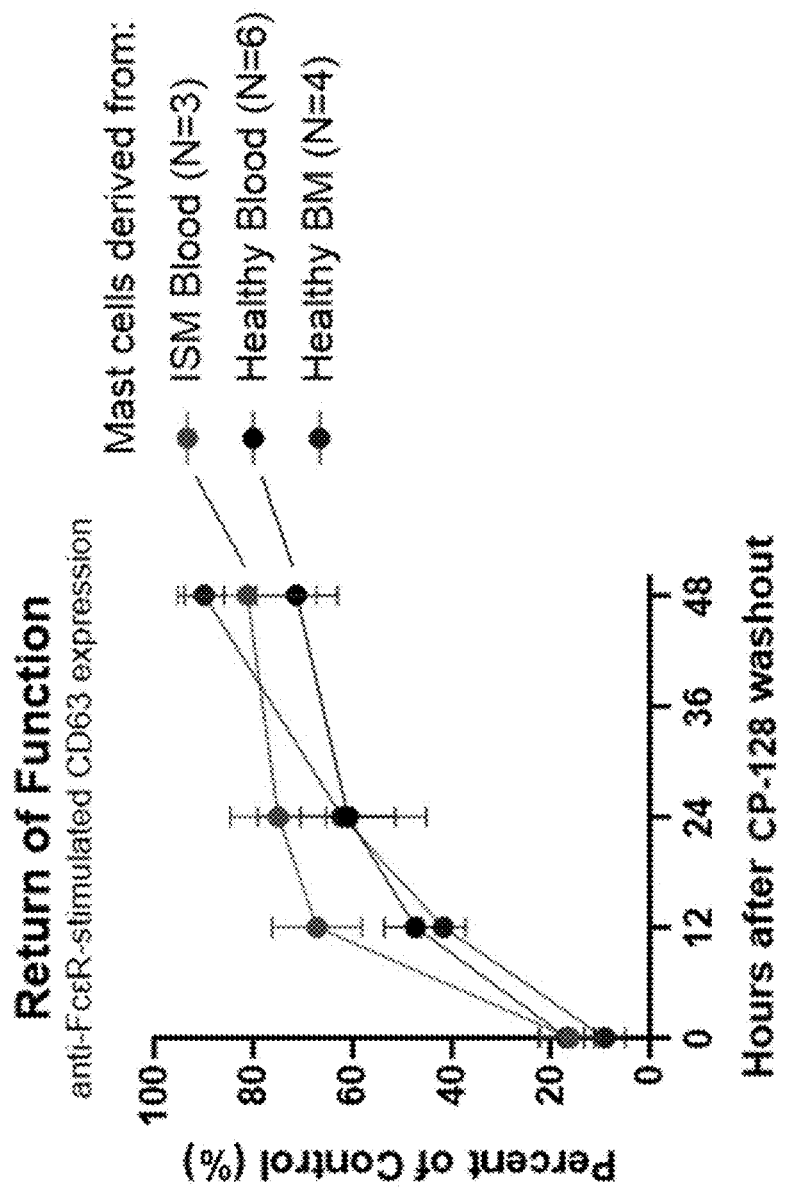
FIG. 18D shows the return of function after Compound-128 washout in mast cells derived from ISM patient blood, healthy donor blood, and healthy donor bone marrow. The data demonstrate that mast cells derived from ISM patients exhibit a faster return of function, suggesting a higher rate of BTK resynthesis.
Figure 19:
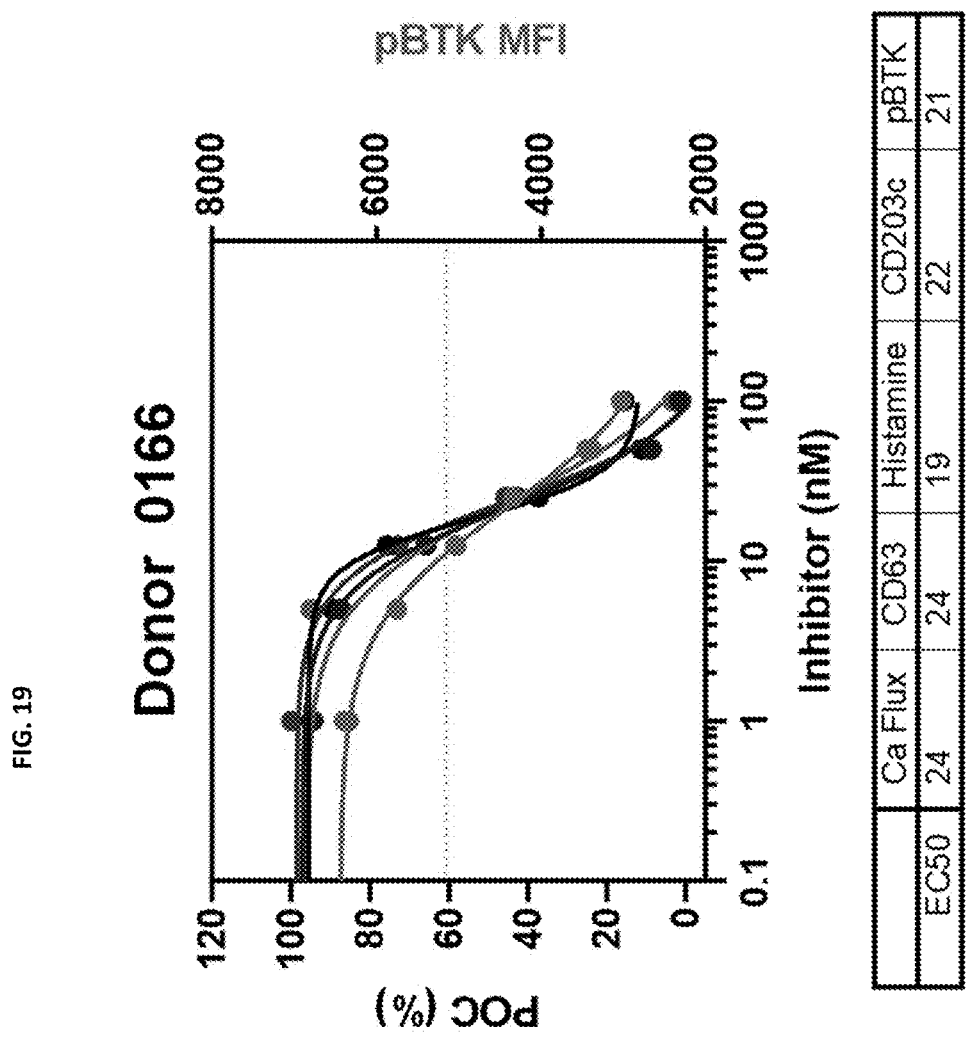
FIG. 19 shows that Compound 128 has high potency in inhibiting BTK phosphorylation in mast cells, correlating with the inhibition of downstream calcium signaling and markers of degranulation (CD63, CD203c, and histamine release).
Figure 20:
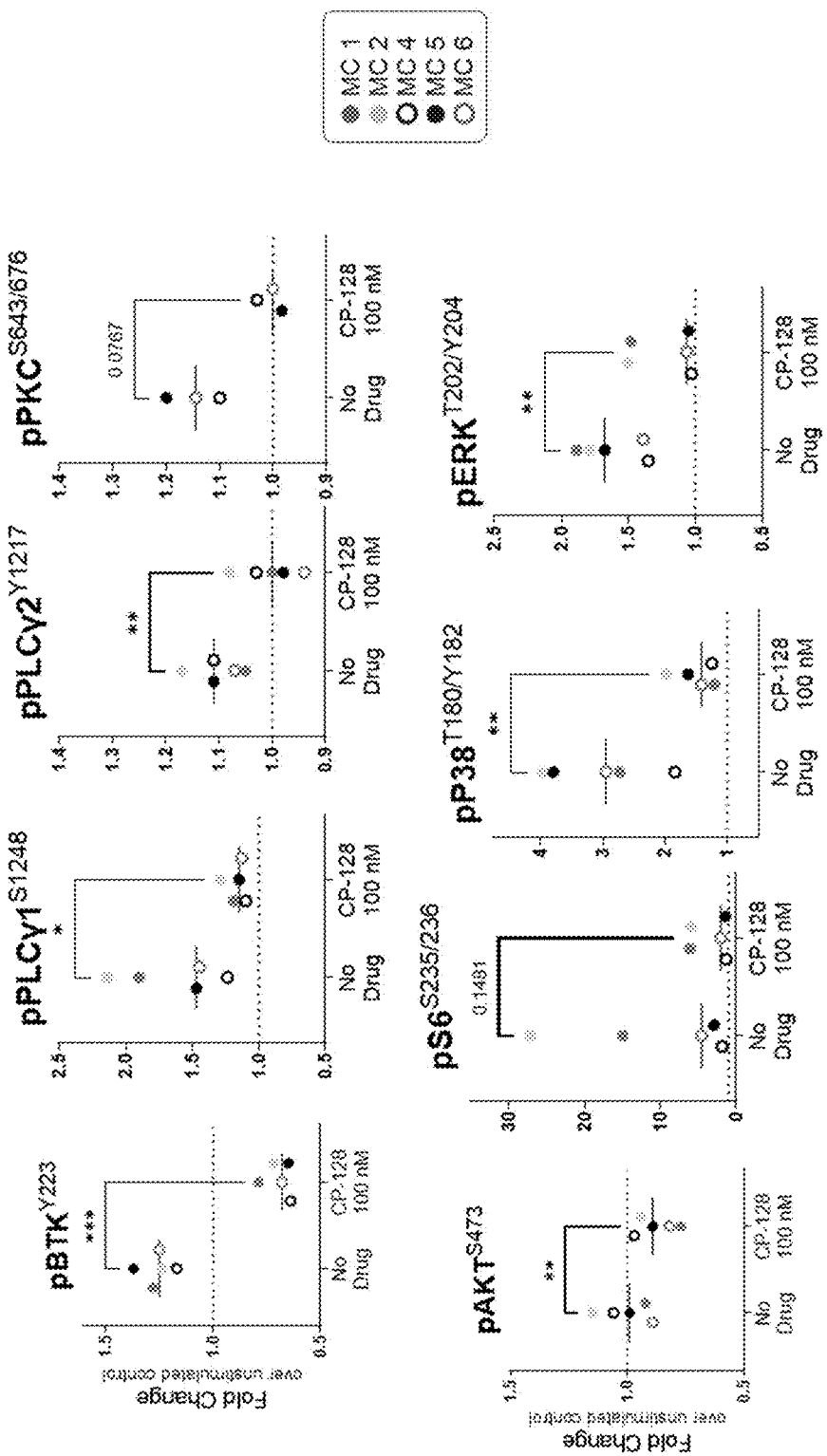
FIG. 20 shows that mast cells stimulated with an antigen activate multiple downstream signaling proteins, which can be inhibited by Compound 128.
Figure 21:
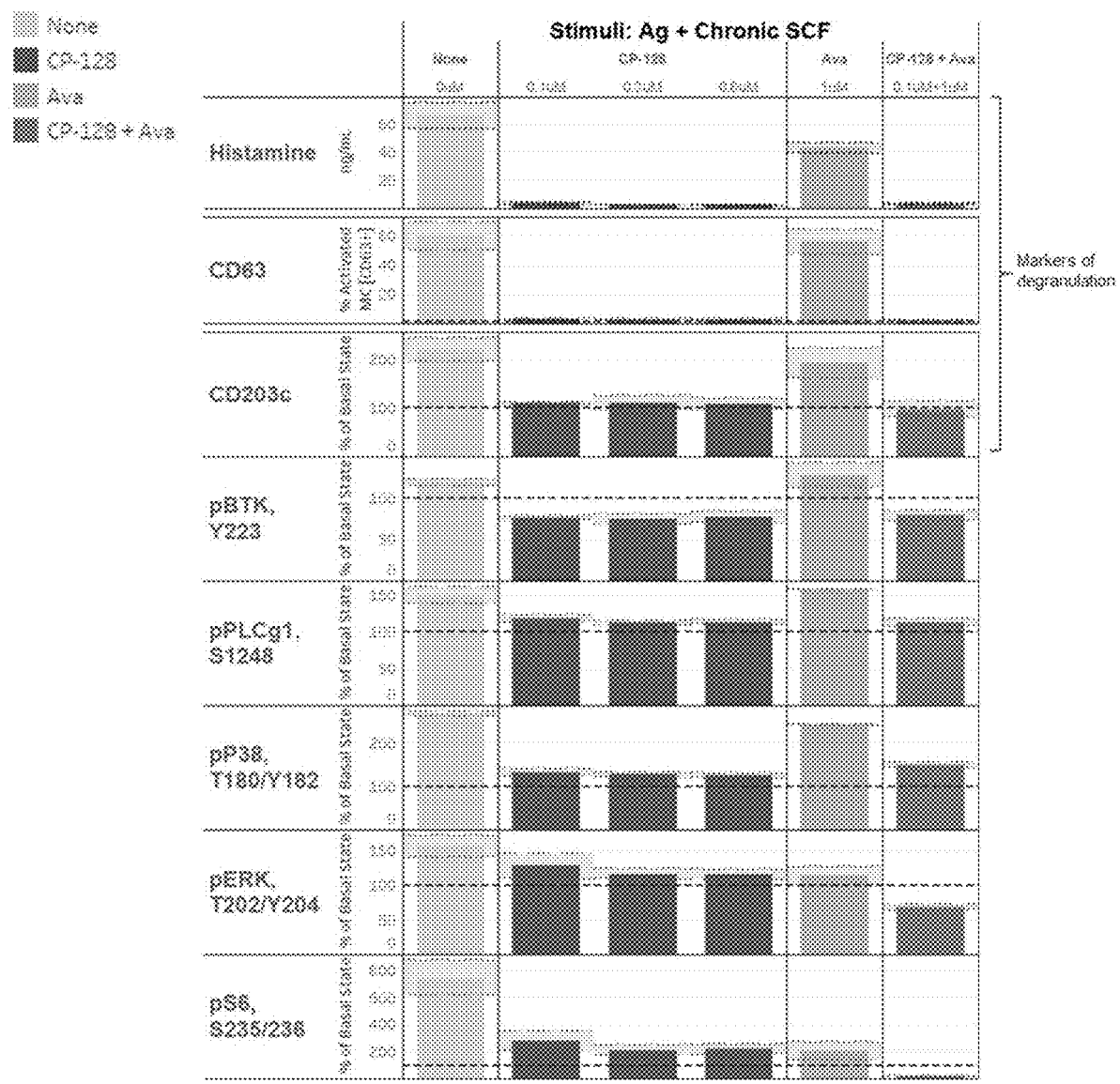
FIG. 21 shows the effects of treatment of mast cells (MCs) with concentrations of Compound 128, avapritinib (Ava), or a combination of Compound 128 and Ava compared to basal levels (dashed lines). Histamine release, CD63 expression, CD203c expression, pBTK (Y223) levels, pP38 (T180/Y182) levels, pPLCg1 (S1248) levels, pERK (T202/Y204) levels, and pS6 (S235/236) levels are shown. Mast cells were grown with continuous (chronic) exposure to SCF and then stimulated with antigen (Ag) for 15 minutes, leading to phosphorylation of multiple kinases, including pBTK, pPLCγ1, pP38, pERK, and pS6 ribosome. This stimulation increases degranulation markers, including CD63, CD203c, and histamine release. However, when mast cells are stimulated in the presence of Compound 128 (0.1-0.6 µM), phosphorylation and degranulation decrease to near basal levels (dashed line). In contrast, the KIT inhibitor avapritinib (1 µM) only partially inhibits activation.
Figure 22:
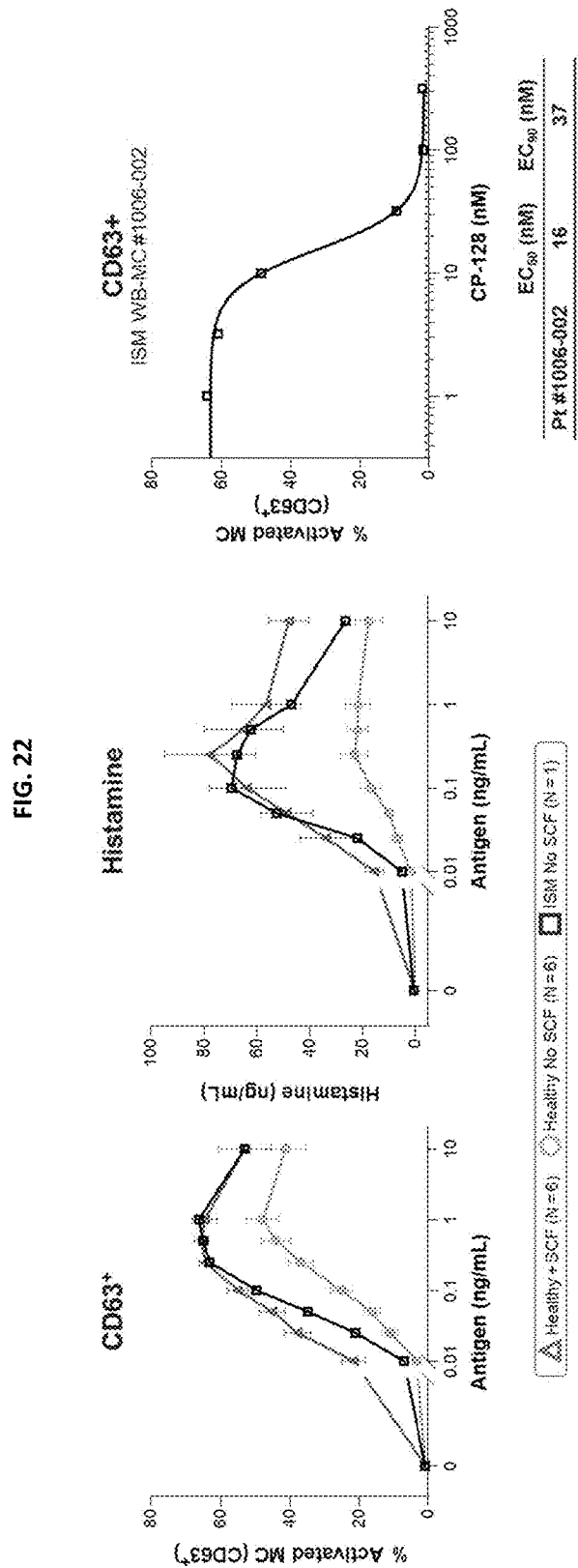
FIG. 22 shows that mast cells grown from CD34+ blood cells from ISM patients were sensitive to antigen stimulation despite the absence of SCF at the time of stimulation, and Compound 128 inhibited the degranulation of these mast cells. The graph demonstrates that the mast cells derived from ISM patients have antigen sensitivity equivalent to healthy mast cells stimulated with stem cell factor and are hypersensitive.

Example 13: Inhibition of MRGPRX2-Mediated Cytokine Production in ISM-Like Mast Cells Through BTK Inhibition Human mast cells were differentiated from bone marrow CD34+ cells from four healthy donors and were cultured in the presence of SCF (100 ng/mL) to mimic mast cells in ISM and treated with Compound 128 for two hours prior to stimulation. Mas-related G protein-coupled receptor (MRGPRX2) agonists, Compound 48/80 (C48/80; a product of N-methyl-p-methoxyphenethylamine with formaldehyde) or Substance P (SP) were used to activate the MRGPRX2 pathway. For pBTK test, cells were stimulated with C48/80 (10 μg/mL) for ten minutes at 37° C. and cells were stained. The median fluorescence intensity of phosphorylated BTK was measured. The fold change over unstimulated control for pBTK was calculated. For cytokine test, cells were stimulated with C48/80 (10 μg/mL) or SP (30 μM) for four hours at 37° C. Supernatant was collected and cytokine levels were measured using the BD Cytometric Bead Array (CBA) human soluble protein master buffer kit (Becton Dickinson) and BD CBA human soluble protein flex sets for IL-8, MCP-1, GM-CSF and IL-13 (Becton Dickinson). Cytokine levels were measured and normalized to percent of control, with 0% representing the level of the unstimulated control. FIG. 15A shows the fold change over unstimulated control for MRGPRX2-induced BTK phosphorylation in three donors with ISM-like mast cell conditions. FIG. 15B shows the percentage of control for MRGPRX2-induced cytokine production in three donors with ISM-like mast cell conditions. FIG. 15C shows the percentage of control for MRGPRX2-induced cytokine production across different agonists and Compound 128 concentrations in one donor with ISM-like mast cell conditions. The results demonstrate that MRGPRX2 activation leads to BTK phosphorylation, which was inhibited by Compound 128 at 0.1 μM. MRGPRX2-mediated cytokine production was partially inhibited by Compound 128 at 0.1 μM. With higher concentrations of Compound 128 at 0.5 and 1 μM, inhibition of cytokine production was increased. Compound 128 fully inhibited SP-mediated cytokine production compared to partial inhibition of C48/80-mediated cytokine production. This data reveals that BTK plays a role downstream of MRGPRX2 activation of ISM-like mast cells and Compound 128 has a functional impact by blocking MRGPRX2-mediated cytokine production.

Example 14: Tryptase Measurement

The measurement of serum tryptase can be followed to the procedure described in the literature (McMurray et al., Standardized indolent systemic mastocytosis evaluations across a health care system: implications for screening accuracy, *Blood* (2024) 144 (4): 408-419). Briefly, the procedure begins with proper patient preparation, avoiding recent physical activity or triggers that could cause mast cell activation. Venous blood samples, preferably drawn when the patient is not experiencing acute symptoms, are collected in serum separator tubes (SSTs) or plain red-top tubes, with approximately 5 mL of blood needed for analysis. After collection, the blood is allowed to clot at room temperature for 30-60 minutes before centrifugation for 10-15 minutes. The serum is then carefully separated from the cells and stored at 2-8° C. for short-term analysis or frozen at −20° C. or lower for long-term storage. The measurement is conducted using immunoassay techniques such as enzyme-linked immunosorbent assay (ELISA) or automated fluoro-immunoassay, adhering strictly to the manufacturer's protocol. Quality control samples and assay calibrators are included to ensure precision and accuracy. Normal baseline tryptase levels are typically <11.5 ng/mL, with levels persistently above 20 ng/mL indicative of systemic mastocytosis when correlated with clinical and histological findings.

Example 15: Bone Marrow Mast Cell Burden Measurement

The measurement of bone marrow mast cell burden can be followed to the procedure described in the literature (Valent et al., Diagnosis and treatment of systemic mastocytosis: state of the art, *Blood,* 129(11), 1420-1427). Briefly, the process begins with a bone marrow biopsy and aspiration, typically obtained from the posterior iliac crest under local anesthesia. The collected samples are prepared by allowing the aspirated material to clot and processing the core biopsy in formalin for histological evaluation. Staining with Giemsa or toluidine blue highlights the characteristic metachromatic granules of mast cells, while immunohistochemistry using antibodies against tryptase and CD117 (c-KIT) further enhances the visualization and specificity of mast cell identification. For quantification, mast cells are counted microscopically to determine the proportion within the marrow, with special attention to morphology. The presence of spindle-shaped mast cells and clusters (>15 cells per aggregate) supports the diagnosis of SM, as these are hallmark features of the disease. Normal bone marrow typically contains less than 1% mast cells, making any significant increase notable. Correlating the bone marrow findings with serum tryptase levels—elevated baseline levels (>20 ng/mL) often accompany SM—enhances diagnostic confidence. Comprehensive reporting of the mast cell burden includes details of cell density, atypical morphology, clustering, flow cytometry results, and genetic testing outcomes. This systematic approach ensures accurate diagnosis, staging, and monitoring, supporting clinical decision-making and patient management.

Example 16: Measurement of KIT D816V Variant Allele Fraction (VAF) in Blood

The measurement of KIT D816V variant allele fraction (VAF) can be followed to the procedure described in the literature (Kristensen et al., Sensitive detection of the KIT D816V mutation in patients with systemic mastocytosis using real-time quantitative PCR, *European Journal of Haematology,* 2011, 86(6), 505-512). Briefly, the process begins with the collection of peripheral blood in EDTA-containing tubes, ensuring the integrity of the sample through prompt storage at 2-8° C. Genomic DNA is then extracted using a standardized kit or automated system, with the DNA quality and concentration assessed spectrophotometrically, ideally achieving an A260/A280 ratio of 1.8-2.0. Targeted amplification of the KIT gene region containing the D816V mutation is performed using allele-specific polymerase chain reaction (PCR) or highly sensitive quantitative PCR (qPCR) methods. Digital PCR (dPCR) may be employed for its superior sensitivity, allowing precise quantification of low-level mutations through sample partitioning. Detection of the mutation is achieved using allele-specific primers in real-time PCR, often with TaqMan probes, or confirmed through sequencing methods such as next-generation sequencing (NGS) for comprehensive mutation profiling. The VAF is calculated as the proportion of mutant allele reads relative to total (mutant plus wild-type) reads, facilitated by bioinformatics analysis when using sequencing approaches. Controls and repeat testing are incorporated to ensure reproducibility, with assay sensitivity tailored to clinical requirements, such as a threshold of 0.1% for dPCR.

The invention claimed is:

1. A method of treating indolent systemic mastocytosis (ISM) in a human subject in need thereof comprising orally administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, wherein the BTK inhibitor inhibits at least 90% of basophil activation following administration as measured by basophil CD63 expression in the human subject, thereby treating ISM in the human subject.

2. The method of claim 1, wherein the peak plasma concentration (Cmax) of the BTK inhibitor in the human subject following administration is at least 125 ng/ml.

3. The method of claim 1, wherein the BTK inhibitor inhibits at least 95% of basophil activation measured by CD63 expression in the human subject.

4. The method of claim 1, wherein the BTK inhibitor inhibits at least 98% of basophil activation measured by CD63 expression in the human subject.

5. The method of claim 1, wherein the BTK inhibitor inhibits about 95% of basophil activation measured by CD63 expression in the human subject.

6. The method of claim 1, wherein the human subject has a KIT D816V mutation.

7. The method of claim 1, wherein the human subject does not have a KIT D816V mutation.

8. The method of claim 1, wherein the BTK inhibitor is administered twice daily at a dose selected from 50 mg, 75 mg, 100 mg, 150 mg, 200 mg, 250 mg, and 300 mg.

9. The method of claim 1, wherein the BTK inhibitor is administered in an amount sufficient to reduce release of histamine and/or cytokines from mast cells in the human subject.

10. The method of claim 1, wherein the BTK inhibitor is administered in an amount sufficient to reduce release of histamine and/or cytokines from basophil cells in the human subject.

11. The method of claim 1, wherein the BTK inhibitor is administered in an amount sufficient to inhibit MRGPRX2-mediated mast cell cytokine production in the human subject.

12. The method of claim 1, wherein the BTK inhibitor is administered in an amount sufficient to reduce release of histamine in the human subject.

13. The method of claim 1, wherein the BTK inhibitor is administered in an amount sufficient to reduce release of leukotrienes in the human subject.

14. The method of claim 1, wherein the BTK inhibitor is administered in an amount sufficient to reduce release of tryptase in the human subject.

15. The method of claim 1, wherein the BTK inhibitor is administered in an amount sufficient to reduce release of prostaglandins in the human subject.

16. The method of claim 1, wherein the BTK inhibitor is administered in an amount sufficient to reduce release of kinins, serotonin, heparin and serine proteases in the human subject.

17. The method of claim 1, wherein the BTK inhibitor is administered in an amount sufficient to reduce IgE-mediated FCεRI activity in the human subject.

18. The method of claim 17, wherein the IgE-mediated FCεRI activity is associated with antigen binding to IgE in the human subject.

19. The method of claim 17, wherein the IgE-mediated FCεRI activity is associated with monomeric IgE binding to FCεRI in the human subject.

20. The method of claim 17, wherein the IgE-mediated FCεRI activity is calcium signaling associated with mast cell degranulation in the human subject.

21. The method of claim 20, wherein the mast cell degranulation is IgE dependent.

22. The method of claim 1, wherein the BTK inhibitor is administered in an amount sufficient to reduce non-IgE-mediated FCεRI activity in the human subject.

23. The method of claim 1, wherein the human subject is ISM treatment naïve.

24. The method of claim 1, wherein the human subject has previously failed treatment of a KIT inhibitor selected from the group consisting of regorafenib, sorafenib, imatinib, ilorasertib, sunitinib, pazopanib, lenvatinib, dasatinib, bezuclastinib, exarafenib, nintedanib, telatinib, avapritinib, TPX-0022, crenolanib, midostaurin, nilotinib, and pharmaceutically acceptable salts thereof.

25. The method of claim 1, wherein administering the BTK inhibitor reduces the frequency of anaphylactic reactions in the human subject.

26. The method of claim 1, wherein administering the BTK inhibitor reduces the severity of anaphylactic reactions in the human subject.

* * * * *